US010472642B2

(12) United States Patent
Le Lay et al.

(10) Patent No.: US 10,472,642 B2
(45) Date of Patent: Nov. 12, 2019

(54) METHOD FOR THE REDUCTION OF TOBACCO-SPECIFIC NITROSAMINES OR THEIR PRECURSORS IN TOBACCO PLANTS

(71) Applicant: BRITISH AMERICAN TOBACCO (INVESTMENTS) LIMITED, London (GB)

(72) Inventors: Pascaline Le Lay, London (GB); Juan Pablo Sanchez Tamburrino, Cambridge (GB)

(73) Assignee: British American Tobacco (Investments) Limited, London (GB)

( * ) Notice: Subject to any disclaimer, the term of this patent is extended or adjusted under 35 U.S.C. 154(b) by 0 days.

(21) Appl. No.: 15/549,077

(22) PCT Filed: Feb. 4, 2016

(86) PCT No.: PCT/GB2016/050260
§ 371 (c)(1),
(2) Date: Aug. 4, 2017

(87) PCT Pub. No.: WO2016/124932
PCT Pub. Date: Aug. 11, 2016

(65) Prior Publication Data
US 2018/0037902 A1 Feb. 8, 2018

(30) Foreign Application Priority Data
Feb. 5, 2015 (GB) .................................. 1501941.7

(51) Int. Cl.
*C12N 15/82* (2006.01)
*C07K 14/415* (2006.01)
*A24B 15/20* (2006.01)
*A24B 3/12* (2006.01)
*A24B 15/10* (2006.01)
*A24B 15/24* (2006.01)

(52) U.S. Cl.
CPC ............ *C12N 15/8243* (2013.01); *A24B 3/12* (2013.01); *A24B 15/10* (2013.01); *A24B 15/20* (2013.01); *A24B 15/245* (2013.01); *C07K 14/415* (2013.01); *C12N 15/8225* (2013.01)

(58) Field of Classification Search
CPC .............. C07K 14/415; C12N 15/8243; C12N 15/8225; A24B 15/20; A24B 3/12; A24B 15/10; A24B 15/245
See application file for complete search history.

(56) References Cited

U.S. PATENT DOCUMENTS

| 2,162,738 A | 6/1939 | McCoy |
| 4,683,202 A | 7/1987 | Mullis |
| 5,565,350 A | 10/1996 | Kmiec |
| 2002/0023281 A1 | 2/2002 | Gorlach et al. |
| 2002/0160378 A1 | 10/2002 | Harper et al. |
| 2004/0144397 A1* | 7/2004 | Conkling ............... A24B 15/10 131/347 |
| 2004/0216190 A1 | 10/2004 | Kovalic |
| 2005/0198711 A1 | 9/2005 | Evans |
| 2005/0204429 A1 | 9/2005 | Penell et al. |
| 2005/0246785 A1 | 11/2005 | Cook et al. |
| 2006/0015970 A1 | 1/2006 | Pennel et al. |
| 2006/0021088 A1 | 1/2006 | Inze et al. |
| 2006/0031960 A1 | 2/2006 | Alexandrov et al. |
| 2006/0048240 A1 | 3/2006 | Alexandrov et al. |
| 2006/0107345 A1 | 5/2006 | Alexandrov et al. |
| 2006/0107346 A1 | 5/2006 | Schneeberger et al. |
| 2006/0112452 A1 | 5/2006 | Keetman et al. |
| 2006/0150283 A1 | 7/2006 | Alexandrov et al. |
| 2006/0218674 A1 | 9/2006 | Sakai et al. |
| 2006/0236427 A1 | 10/2006 | Chiang et al. |
| 2007/0016976 A1 | 1/2007 | Katagiri et al. |
| 2007/0124833 A1 | 5/2007 | Abad et al. |
| 2007/0124834 A1 | 5/2007 | Cook et al. |
| 2007/0214517 A1 | 9/2007 | Alexandrov et al. |
| 2007/0266454 A1 | 11/2007 | Anderson et al. |
| 2009/0019601 A1 | 1/2009 | Kovalic |
| 2009/0075829 A1 | 3/2009 | Bush et al. |
| 2009/0083876 A1 | 3/2009 | Coruzzi et al. |

(Continued)

FOREIGN PATENT DOCUMENTS

| AU | 2005247022 A | 1/2006 |
| AU | 2008200749 A1 | 3/2008 |

(Continued)

OTHER PUBLICATIONS

Shuai, Bin, Cristina G. Reynaga-Pena, and Patricia S. Springer. "The lateral organ boundaries gene defines a novel, plant-specific gene family." Plant physiology 129.2 (2002): 747-761. (Year: 2002).*

Yang, Yi, Xiaobo Yu, and Ping Wu. "Comparison and evolution analysis of two rice subspecies Lateral Organ Boundaries domain gene family and their evolutionary characterization from *Arabidopsis*." Molecular phylogenetics and evolution 39.1 (2006): 248-262. (Year: 2006).*

Rubin, Grit, et al. "Members of the LBD family of transcription factors repress anthocyanin synthesis and affect additional nitrogen responses in *Arabidopsis*." The Plant Cell 21.11 (2009): 3567-3584. (Year: 2009).*

(Continued)

*Primary Examiner* — Weihua Fan
(74) *Attorney, Agent, or Firm* — McKee, Voorhees & Sease, PLC

(57) ABSTRACT

The present invention provides a method for reducing at least one tobacco-specific nitrosamine or a precursor thereof in tobacco comprising modifying the tobacco plant by increasing the activity or expression of a LBD (lateral organ bound domain) nitrogen-responsive transcription factor. The present invention also provides tobacco cells, tobacco plants, tobacco plant propagation materials, harvested leaves, processed tobaccos, or tobacco products obtainable in accordance with the invention.

38 Claims, 10 Drawing Sheets

Specification includes a Sequence Listing.

(56) References Cited

U.S. PATENT DOCUMENTS

| | | | |
|---|---|---|---|
| 2009/0172834 A1 | 7/2009 | Schauwecker et al. | |
| 2009/0178161 A1 | 7/2009 | Arar et al. | |
| 2009/0215647 A1 | 8/2009 | Bush et al. | |
| 2010/0037352 A1 | 2/2010 | Alexandrov et al. | |
| 2010/0037355 A1 | 2/2010 | Alexandrov et al. | |
| 2010/0132071 A1* | 5/2010 | Hatzfeld | C07K 14/415 800/290 |
| 2010/0257621 A1 | 10/2010 | Ketkar et al. | |
| 2010/0269217 A1 | 10/2010 | van der Knaap et al. | |
| 2011/0041219 A1 | 2/2011 | Cook et al. | |
| 2011/0099668 A1 | 4/2011 | Singh et al. | |
| 2011/0113499 A1 | 5/2011 | Taramino et al. | |
| 2011/0265221 A1 | 10/2011 | Abad et al. | |
| 2011/0281765 A1 | 11/2011 | Bush et al. | |
| 2012/0079622 A1 | 3/2012 | Li | |
| 2012/0159672 A1 | 6/2012 | Alexandrov et al. | |
| 2012/0185968 A1 | 7/2012 | Busov et al. | |
| 2012/0210460 A1 | 8/2012 | Crawford et al. | |
| 2013/0096032 A1 | 4/2013 | Bush et al. | |
| 2013/0174483 A1 | 7/2013 | Caspar et al. | |
| 2013/0180173 A1 | 7/2013 | Caspar et al. | |
| 2013/0191936 A1 | 7/2013 | De Block et al. | |
| 2013/0333068 A1 | 12/2013 | Coffin | |
| 2014/0007292 A1 | 1/2014 | Cerf et al. | |
| 2014/0033361 A1 | 1/2014 | Altier et al. | |
| 2014/0090114 A1 | 3/2014 | Kovalic | |
| 2014/0274885 A1 | 9/2014 | Cong et al. | |
| 2014/0275208 A1 | 9/2014 | Hu et al. | |
| 2014/0287922 A1 | 9/2014 | Chame et al. | |

FOREIGN PATENT DOCUMENTS

| | | |
|---|---|---|
| CA | 2523471 A | 5/2006 |
| EP | 0120516 A2 | 2/1984 |
| EP | 0449375 A2 | 10/1991 |
| EP | 1033405 A2 | 9/2000 |
| EP | 1586645 A2 | 10/2005 |
| EP | 2316953 A2 | 5/2011 |
| GB | 2515502 A | 12/2014 |
| KR | 20120081270 A | 7/2012 |
| WO | 9322443 A1 | 11/1993 |
| WO | 9720056 A2 | 6/1997 |
| WO | 2002016655 A2 | 2/2002 |
| WO | 2003000898 A2 | 1/2003 |
| WO | 2004035798 A2 | 4/2004 |
| WO | 2007110314 A2 | 10/2007 |
| WO | 08107509 A1 | 9/2008 |
| WO | 2008137108 A2 | 11/2008 |
| WO | 2009009142 A2 | 1/2009 |
| WO | 200922183 A1 | 2/2009 |
| WO | 2010097623 A1 | 9/2010 |
| WO | 2012038717 A1 | 3/2012 |
| WO | 2012041496 A1 | 4/2012 |
| WO | 2013034459 A1 | 3/2013 |
| WO | 13104026 A1 | 7/2013 |
| WO | 2014096283 A2 | 6/2014 |
| WO | 14150914 A2 | 9/2014 |
| WO | 14201156 A1 | 12/2014 |

OTHER PUBLICATIONS

Li, Hao-Hao, et al. "Cloning and elucidation of the functional role of apple MdLBD13 in anthocyanin biosynthesis and nitrate assimilation." Plant Cell, Tissue and Organ Culture (PCTOC) 130.1 (2017): 47-59. (Year: 2017).*

Iwakawa, Hidekazu, et al. "The Asymmetric LEAVES2 gene of *Arabidopsis thaliana*, required for formation of a symmetric flat leaf lamina, encodes a member of a novel family of proteins characterized by cysteine repeats and a leucine zipper." Plant and Cell Physiology 43.5 (2002): 467-478. (Year: 2002).*

Dewey, Ralph E., and Jiahua Xie. "Molecular genetics of alkaloid biosynthesis in Nicotiana tabacum." Phytochemistry 94 (2013): 10-27 (Year: 2013).*

Altenhoff, Adrian M., and Christophe Dessimoz. "Inferring orthology and paralogy." Evolutionary genomics. Humana Press, Totowa, NJ, 2012. 259-279 (Year: 2012).*

Jensen, Roy A. "Orthologs and paralogs—we need to get it right." Genome biology 2.8 (2001): interactions 1002-1. (Year: 2001).*

Matsumura, Yoko, et al. "Characterization of genes in the Asymmetric LEAVES2/Lateral Organ Boundaries (AS2/LOB) family in *Arabidopsis thaliana*, and functional and molecular comparisons between AS2 and other family members." The Plant Journal 58.3 (2009): 525-537 (Year: 2009).*

Majer, Christine, and Frank Hochholdinger. "Defining the boundaries: structure and function of LOB domain proteins." Trends in plant science 16.1 (2011): 47-52. (Year: 2011).*

Zhu, Lin, et al. "Ectopic expression of LBD15 affects lateral branch development and secondary cell wall synthesis in *Arabidopsis thaliana*." Plant growth regulation 73.2 (2014): 111-120. (Year: 2014).*

Albinsky, Doris, et al. "Metabolonnic screening applied to rice FOX *Arabidopsis* lines leads to the identification of a gene-changing nitrogen metabolism." Molecular plant 3.1 (2010): 125-142 (Year: 2010).*

Christou, P., Genetic engineering of crop legumes and cereals: current status and recent advances, Agro-Food-Industry Hi-Tech March/April, pp. 17-27, Apr. 1994.

Chwojdak, C. A. et al, A collaborative, harmonized LC-MS/MS method for the determination of tobacco specific nitrosamines (TSNA) in tobacco and tobacco related materials. 61st Tobacco Science Research Conference, Charlotte, NC, USA. Sep. 24, 2007.

Clough, S.J. & Bent, A.F., Floral dip: a simplified method for Agrobacterium-mediated transformation of *Arabidopsis thaliana*, The Plant Journal, 16(6) pp. 735-743. 1998.

Cornejo, M. J. et al., Activity of a maize ubiquitin promoter in transgenic rice, Plant Molecular Biology, vol. 23, pp. 567-581 1993.

Foulds, J. et al, Effect of smokeless tobacco (snus) on smoking and public health in Sweden. Tobacco Control, vol. 12, pp. 349-359 2003.

Fraley, R. T. et al, Genetic Transformation in Higher Plants, Critical Review Plant Science, vol. 4, issue 1, pp. 1-46 1986.

Frame, B. R. et al, Production of fertile transgenic maize plants by silicon carbide whisker-mediated transformation, The Plant Journal, vol. 6, pp. 941-948 1994.

Freeling and Walbot (editors), The Maize Handbook, Chapter 116, Springer, N.Y., 1994.

Gan, S. and Amasino, R. M., Making Sense of Senescence, Molecular Genetic Regulation and Manipulation of Leaf Senescence, Plant Physiology, 113: pp. 313-319 1997.

Gatz, C., Novel Inducible/Repressible Gene Expression Systems, Methods in Cellular Biology, vol. 50, pp. 411-424, 1995.

Gepstein, S. et al., Large-scale identification of leaf senescence-associated genes, The Plant Journal, 36, pp. 629-642, 2003.

Higgins, D. G. & Sharp P.M., CLUSTAL: a package for performing multiple sequence alignment on a microcomputer; Gene, vol. 73, No. 1, pp. 237-244, 1988.

Hoekema, A. et al., Non-Oncogenic T-region Derived Plant Vectors in the Agrobacterium Binary System, in: The Binary Plant Vector System Offset-drukkerij Kanters B. B., Amsterdam, Chapter V, pp. 63-71 1985.

Horn, T. et al, Synthesis of olignonucleotides on cellulose. Part II: design and sythetic strategy to the synthesis of 22 oligodeoxynucleotides coding for Gastric Inhibitory Polypeptide (GIP), Nucleic Acids Research, Symposium Series, No. 7, pp. 225-232, 1980.

Horsch, R. B. et al, A Simple and General Method for Transferring Genes into Plants, Science, vol. 227, pp. 1229-1231. 1985.

Horwell, D. C., The 'peptoid' approach to the design of non-peptide, small molecule agonsits and antagonists of neuropeptides, Trends Biotechnology, 13(4), pp. 132-134, 1995.

Hull, R. et al, The sequence of carnation etched ring virus DNA: comparison with cauliflower mosaic virus and retroviruses, The EMBO Journal, 5(12):3083-3090 1986.

Lee, J-M et al, Coresta Congress Kyoto, Paper SS20; See http://www.coresta.org/Past_abstracts/Kyoto2004-SmokeTech.pdf, 2004.

(56) References Cited

OTHER PUBLICATIONS

Liang, S. et al, Application of exogenous substances reduces tobacco-specific nitrosamines content by regulating biosynthesis of nicotine and nitrite in burley tobacco, Acta Physiol. Plant., 35: 3027-3036 2013.
Matthes, H. W. D. et al, Simultaneous rapid chemical synthesis of over one hundred oligonucleotides on a microscale, The EMBO Journal, vol. 3, pp. 801-805 1984.
Meyer, P. et al, The use of African cassava mosaic virus as a vector system for plants, Gene, 110, pp. 213-217 1992.
Morot-Gaudry-Talarmain, Y. et al, Nitrate accumulation and nitric oxide emission in relation to cellular signaling in nitrite reductace antisense tobacco. Planta, 215:708-715, 2002.
Mur, et al, Plant Science, 181, pp. 509-519, 2011.
Odell, J.T. et al, Identification of DNA sequences required for activity of the cauliflower mosaic virus 35S promoter, Nature, vol. 313, pp. 810-812, 1985.
Potrykus, I., Gene Transfer to Plants: Assessment of Published Approaches and Results, Annual Revue Plant Physiology Plant Molecular Biology, vol. 42, pp. 205-225 1991.
Saiki, R. K., et al, Primer-Directed Enzymatic Amplification of DNA with a Thermostable DNA Polymerase, Science, vol. 239, pp. 487-491, 1988.
Shi, H., et al, The relationships between TSNAs and their precursors in burley tobacco from regions and varieties, Journal of Food, Agriculture & Environment, vol. 10 (3&4): 1048-1052 2012.
Silva, et al, Meganucleases and Other Tools for Targeted Genome Engineering: Perspectives and Challenges for Gene Therapy, Current Gene Therapy, 11(1): 11-27 Feb. 2011.
Simon, R. J. et al, Peptoids: A modular approach to drug discovery, Proc. Natl. Acad. Sci. USA, vol. 89, No. 20, pp. 9367-9371 1992.
Tatusova, T. et al, Erratum to BLAST 2 Sequences, a new tool for comparing protein and nucleotide sequences, FEMS Microbiology Letters, 177(1): 187-188 1999.
Tatusova, T. et al, BLAST 2 Sequences, a new tool for for comparing protein and nucleotide sequences, FEMS Microbiology Letters, 174(2): 247-250 1999.
Wagner, K. A. et al, Development of a Quantitative Method for the Analysis of Tobacco Specific Nitrosamines in Mainstream Cigarette Smoke Using Isotope Dilution Liquid Chromatography/Electrospray Ionization Tandem Mass Spectrometry, Anal. Chem. 77: 1001-1006, 2005.
Warner, Simon A. et al, Isolation of an asparagus intracellular PR gene (AoPR1) wound-responsive promoter by the inverse polymerase chain reaction and its characterization in transgenic tobacco. The Plant Journal 3(2) pp. 191-201 1993.
Wu, Weijja, et al, Simultaneous Determination of Five Tobacco Specific Nitrosamines in Mainstream Cigarette Smoke by Isotope Dilution Liquid Chromatography/Electrospray Ionization Tandem Mass Spectrometry, Anal. Chem., 75: 4827-4832, 2003.
Zhang, Wanggen, et al, Analysis of rice Act1 5' Region Activity in Transgenic Rice Plants, The Plant Cell, vol. 3, pp. 1155-1165, 1991.
"SPXFLOW", http://spxflow.com/en/bran-luebbe/search-results, Bran + Luebbe Apr. 8, 2017.
Seebold, Kenneth W., et al., "2013-2014 Kentucky & Tennessee Tobacco Production Guide", University of Kentucky, Agriculture and Natural Resources Publications, pp. 44-51 2013.
Bran + Luebbe Analytics, SPX Prcoess Equipment, Auto Analyzer 3, pp. 1-8 2013.
British American Tobacco (Investments) Limited, Application No. PCT/GB2016/050260, "The International Search Report and The Written Opinion of the International Searching Authority", 13 pages, dated Feb. 4, 2016.
Rubin, G., Members of the LBD Family of Transcription Factors Repress Anthocyanin Synthesis and Affect Additional Nitrogen Responses in *Arabidopsis*, Plant Cell, vol. 21, pp. 3567-3584. Electronic Publication Nov. 20, 2009.
Albinsky, D., Metabolomic Screening Applied to Rice FOX *Arabidopsis* Lines Leads to the Identification of a Gene-Changing Nitrogen Metabolism, Molecular plant, (Jan. 2010) vol. 3, No. 1, pp. 125-142. Electronic Publication Aug. 26, 2009.
Djennane, S. et al, Glasshouse behaviour of eight transgenic potato clones with a modified mitrate redutase expression under two fertilization regimes, Journal of Experimental Botany, vol. 53, No. 371, pp. 1037-1045 May 31, 2002.
Lillo, C. et al, Mechanism and importance of post-translational regulation of nitrate reductase, Journal of Experimental Botany, vol. 55, No. 401, pp. 1275-1282 Jun. 30, 2004.
Gojon, A. et al, Effects of genetic modification of nitrate reductase expression on 15NO3—uptake and reduction in Nicotiana plants, Plant, Cell and Environment, vol. 21, pp. 43-53 1998.
Medici, A. et al, The Primary Nitrate Response: a multifaceted signalling pathway, Journal of Experimental Botany, vol. 65, No. 19, pp. 5567-5576 Oct. 31, 2014.
Lewis, M. W. et al, Gene regulatory interactions at lateral organ boundaries in maize, The Company of Biologists Ltd/Development (Cambridge, England), vol. 141, No. 23, pp. 4590-4597. Electronic Publication Date: Oct. 30, 2014, Dec. 31, 2014.
Zhang Yue-Min, Genomewide analysis of Lateral Organ Boundaries Domain gene family in *Zea mays*, Journal of Genetics, vol. 93, No. 1, pp. 79-91, Apr. 2014.
Bargmann Bastiaan, O. R., An Undergraduate Study of Two Transcription Factors That Promote Lateral Root Formation, Biochemistry and Molecular Biology Education : a bimonthly publication of the International Union of Biochemistry and Molecular Biology, (May-Jun. 2014) vol. 42, No. 3, pp. 237-245. Electronic Publication Date: Feb. 24, 2014.
Lee Han Woo, GIP1 may act as a coactivator that enhances transcriptional activity of LBD18 in *Arabidopsis*, Journal of Plant Physiology, (Mar. 1, 2014) vol. 171, No. 5, pp. 14-18 Electronic Publication Date: Dec. 11, 2013.
Ge Liangfa, Regulation of Compound Leaf Development by PHANTASTICA in Medicago truncatula, Plant Physiology, (Jan. 2014) vol. 164, No. 1, pp. 216-228. Electronic Publication Date: Nov. 11, 2013.
Thirunavukkarasu, Nepolean, et al, Genome-Wide Expression of Transcriptomes and Their Co-Expression Pattern in Subtropical Maize (*Zea mays* L.) Under Waterlogging Stress, PlOS One, (2013) vol. 8, No. 8, pp. e70433. Electronic Publication Date: Aug. 6, 2013.
Wang, Xiaofei, et al, A Genome-Wide Analysis of the LBD (Lateral Organ Boundaries Domain) Gene Family in Malus Domestica with a Functional Characterization of MdLBD11, PlOS One, (2013) vol. 8, No. 2, pp. e57044. Electronic Publication Date: Feb. 28, 2013.
Lee Han Woo, The Conserved Proline Residue in the LOB Domain of LBD18 is Critical for DNA-Binding and Biological Function, Molecular Plant, (Sep. 2013) vol. 6, No. 5, pp. 1722-1725. Electronic Publication Date: Feb. 21, 2013.
Kim, Jungmook and Lee, Han Woo, Direct activation of EXPANSIN14 by LBD18 in the gene regulatory network of lateral root formation in *Arabidopsis*, Plant Signaling & Behavior, (Feb. 2013) vol. 8, No. 2, pp. e22979. Electronic Publication Date: Jan. 8, 2013.
Bell, E. M. et al, *Arabidopsis* Lateral Organ Boundaries negatively regulates brassinosteroid accumulation to limit growth in organ boundaries, Proceedings of the National Academy of Sciences of the United States of America, (Dec. 18, 2012) vol. 109, No. 51, pp. 21146-21151. Electronic Publication Date: Dec. 4, 2012.
Coudert, Y. et al, ASL/LBD Phylogeny Suggests that Genetic Mechanisms of Root Initiation Downstream of Auxin are Distinct in Lycophytes and Euphyllophytes, Society for Molecular Biology and Evolution, (Mar. 2013) vol. 30, No. 3, pp. 569-572. Electronic Publication Date: Oct. 30, 2012.
Mangeon, A., Functional divergence in the *Arabidopsis* LOB-domain gene family, Plant Signaling & Behavior, (Dec. 2012) vol. 7, No. 12, pp. 1544-1547. Electronic Publication Date: Oct. 16, 2012.
Zhou, Li-Li, Regulation of anthocyanin biosynthesis by nitrogen in TTG1-GL3/TT8-PAP1-programmed red cells of *Arabidopsis thaliana*, Planta, (Sep. 2012) vol. 236, No. 3, pp. 825-837. Electronic Publication Date: Jun. 6, 2012.
Majer, C., Molecular interactions of Rootless Concerning Crown and Seminal Roots, a LOB domain protein regulating shoot-borne root initiation in maize (*Zea mays* L.), Philosophical Transactions of

(56) References Cited

OTHER PUBLICATIONS

The Royal Society of London. Series B, Biological Sciences, vol. 367, No. 1595, pp. 1542-1551 Jun. 5, 2012.
Bai, Tuanhui, et al, Fine genetic mapping of the Co locus controlling columnar growth habit in apple, Molecular Genetics and Genomics : MGG, (May 2012) vol. 287, No. 5, pp. 437-450. Electronic Publication Date: Apr. 17, 2012.
Castaings, L., et al, "Nitrogen signalling in *Arabidopsis*: how to obtain insights into a complex signalling network", Journal of Experimental Botany, Feb. 2011, vol. 62, No. 4, pp. 1391-1397. Published electronically Nov. 30, 2010.
Majer, C., Defining the boundaries: structure and function of LOB domain proteins, Trends in Plant Science, (Jan. 2011) vol. 16, No. 1, pp. 47-52. Electronic Publication Date: Oct. 18, 2010.
Yordanov, Y. S. et al, Members of the Lateral Organ Boundaries Domain Transcription Factor Family Are Involved in the Regulation of Secondary Growth in Populus, The Plant Cell, (Nov. 2010) vol. 22, No. 11, pp. 3662-3677. Electronic Publication Date: Nov. 19, 2010.
Oh Sung Aeong,The Sidecar Pollen gene encodes a microspore-specific LOB/AS2 domain protein required for the correct timing and orientation of asymmetric cell division, The Plant Journal (Dec. 2010) vol. 64, No. 5, pp. 839-850. Electronic Publication Date: Oct. 26, 2010.
Hochholdinger, F. et al, Conserved and diverse mechanisms in root development, Current opinion in Plant Biology, (Feb. 2008) vol. 11, No. 1, pp. 70-74. Electronic Publication Date: Nov. 19, 2007.
Husbands, A. et al, Lateral Organ Boundaries defines a new family of DNA-binding transcription factors and can interact with specific bHLH proteins, Nucleic Acids Research, (2007) vol. 35, No. 19, pp. 6663-6671. Electronic Publication Date: Oct. 2, 2007.
Taramino, G. et al, The maize (*Zea mays* L.) RTCS gene encodes a LOB domain protein that is a key regulator of embryonic seminal and post-embryonic shoot-borne root initiation, The Plant Journal, (May 2007) vol. 50, No. 4, pp. 649-659. Electronic Publication Date: Apr. 8, 2007.
Evans, M. M. S., The indeterminate gametophyte1 Gene of Maize Encodes a LOB Domain Protein Required for Embryo Sac and Leaf Development, The Plant Cell, (Jan. 2007) vol. 19, No. 1, pp. 46-62. Electronic Publication Date: Jan. 3, 2007.
Jiang-Hong, Luo, Isolation and Expression Patterns of Lateral Organ Boundaries-like Genes in Lotus Japonicus, Journal of Plant Physiology and Molecular Biology, vol. 32, No. 2, pp. 202-208 Apr. 2006.
Yang, Yi et al, Comparison and evolution analysis of two rice subspecies Lateral Organ Boundaries domain gene family and their evolutionary characterization from *Arabidopsis*, Molecular Phylogenetics and Evolution, (Apr. 2006) vol. 39, No. 1, pp. 248-262. Electronic Publication Date: Nov. 14, 2005.
Liu, Hongjia et al, ARL1, a LOB-domain protein required for adventitious root formation in rice, The Plant Journal, vol. 43, No. 1, pp. 47-56 Jul. 2005.
Inukai, Yoshiaki et al, Crown rootless1, Which is Essential for Crown Root Formation in Rice, Is a Target of an Auxin Response Factor in Auxin Signaling, The Plant Cell, (May 2005) vol. 17, No. 5, pp. 1387-1396. Electronic Publication Date: Apr. 13, 2005.
Weir, I et al, CUPULIFORMIS establishes lateral organ boundaries in Antirrhinum, Development (Cambridge, England), vol. 131, No. 4, pp. 915-922 Feb. 2004.
Shuai, Bin et al., The Lateral Organ Boundaries Gene Defines a Novel, Plant-Specific Gene Family, Plant Physiology, vol. 129, No. 2, pp. 747-761 Jun. 2002.
Byrne, M. E., Asymmetric LEAVES1 reveals knox gene redundancy in *Arabidopsis*, Development (Cambridge, England), vol. 129, No. 8, pp. 1957-1965 Apr. 2002.
Postma-Haarsma, A. D. et al, Developmental regulation and downstream effects of the knox class homeobox genes Oskn2 and Oskn3 from rice, Plant Molecular Biology, vol. 48, No. 4, pp. 423-441 Mar. 2002.
Altschul, S. F. et al, Basic Local Alignment Search Tool, J. Mol. Biol., vol. 215, pp. 403-410 1990.
An, G. et al, Binary Vectors, Plant Molecular Biology Manual, A3, pp. 1-19 1988.
An, G. et al, New cloning vehicles for transformation of higher plants, The EMBO Journal., vol. 4, No. 2, pp. 277-284 1985.
An, G. et al, Transformation of Tobacco, Tomato, Potato, and *Arabidopsis thaliana* Using a Binary Ti Vector System, Plant Physiol., vol. 81, pp. 301-305 1986.
Ausubel et al, Short Protocols in Molecular Biology, 4th Edition, Chapter 18 1999.
Ausubel et al, Short Protocols in Molecular Biology, 4th Edition, pp. 7-58- to 7-60 1999.
Benfey, P.N., and Chua, N-H., Regulated Genes in Transgenic Plants, Science, vol. 244, pp. 174-181 1989.
Beaucage, S. L. et al, Deoxynucleoside Phosphoramidites—A New Class of Key Intermediates for Deoxypolynucleotide Synthesesis, Tetrahedron Letters, vol. 22, No. 20, pp. 1859-1862 1981.
Buchman and Berg, Molecular and Cellular Biology, vol. 8, No. 10, pp. 4395-4405 Oct. 1988.
Butcher, D. N. et al, The role of tissue culture in the study of crown-gall tumorigenesis, Tissue Culture Methods for Plant Pathologists, eds.: D. S. Ingrams and J. P. Helgeson, pp. 203-208 1980.
Callis, J. et al, Introns increase gene expression in cultural maize cells, Genes and Development, vol. 1, pp. 1183-1200 1987.
Caruthers, M. H. et al, New chemical methods for synthesizing polynucleotides, Nucleic Acids Research Symposium Series, No. 7, pp. 215-223 1980.

\* cited by examiner

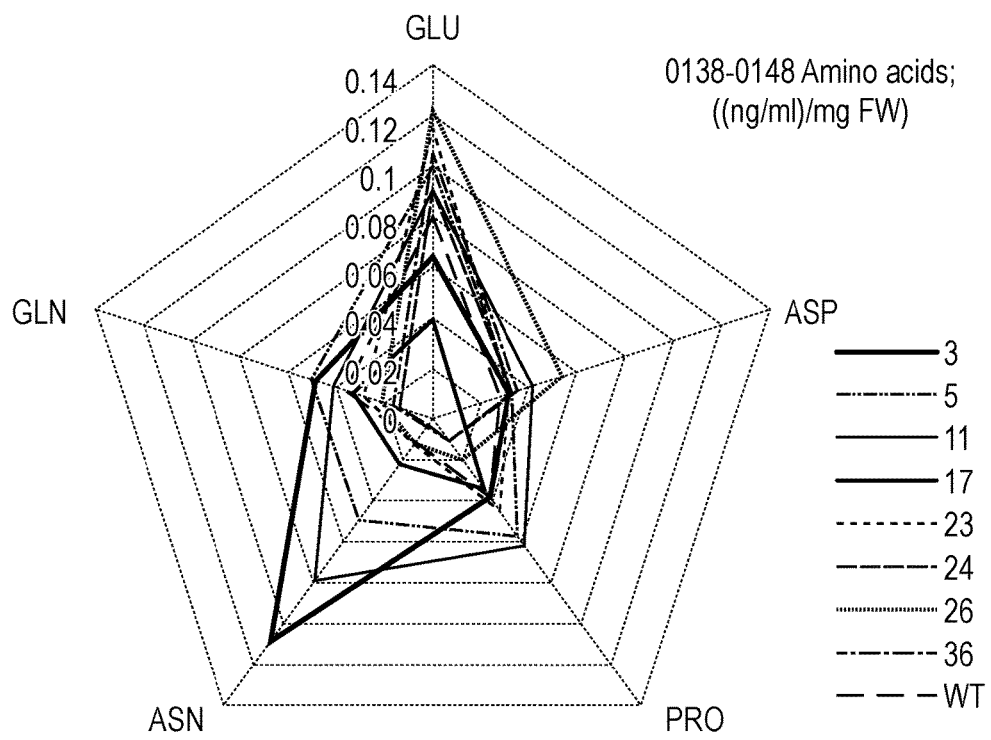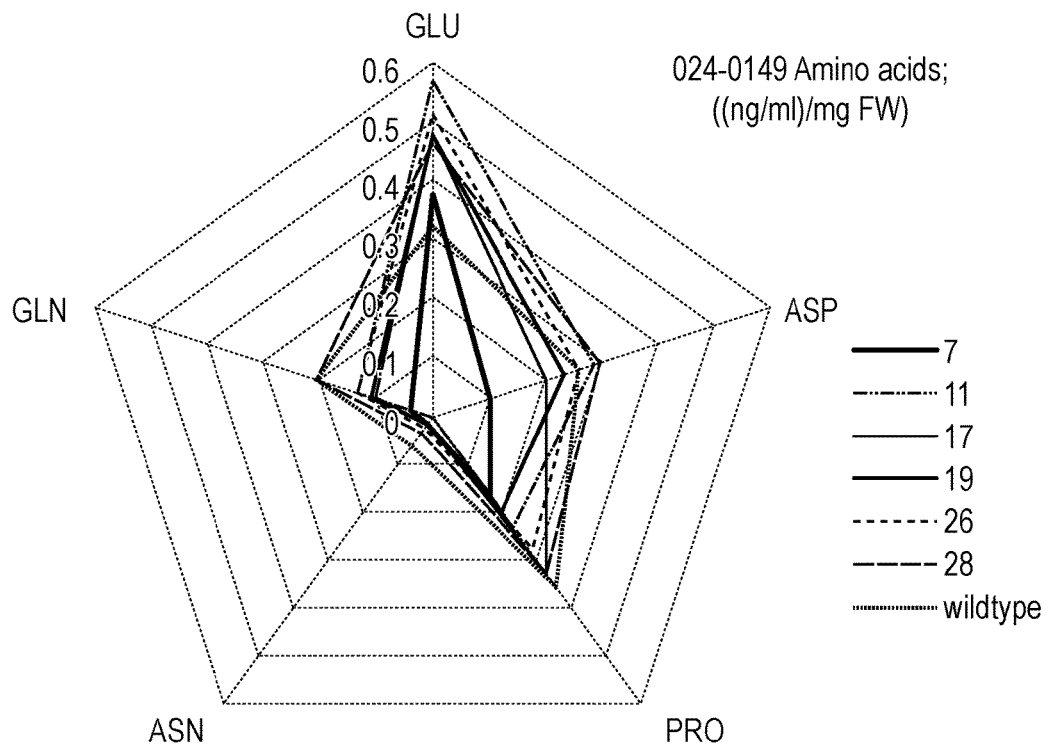
FIG. 2 (continued)

>SEQ_NO_1: AtLBD37 (At5g67420.1) CDS
Atgagctgcaatggttgccgtgttctccggaaaggttgcagcgagaattgtatcctccggcc
atgtattcaatggattgaaaccgccgatgctcaaggccacgccaccgtcttcgtcgctaaat
tcttcggccgtgctggtctcatgtcctttatctccgctgttccggattctcaacgtcctgct
ttgtttcagtcgttgctctacgaagcttgtggaagaactgtcaatccagttaacggagcaat
cggaatgttatggactggaaactggaatatctgtcaagcggctgttgaaacagtgcttcgcg
gcggttctttaagaccgatcccggagcttctcactcacggcggcggtttcgctggcttcct
tcgcctacatctgaagaagcatctgagatctgcaccgaaatgttgaatctccagcaaaatga
ttccaccgatcgtaacatctatcatcattcacgattctcaagctctagatctagatctacta
tggattcttcttctccgacgaaacgtaagagattatcatcggaagaccaaccatcttcggag
cttgatctatctctcatccctaattttcccattaagcaagcaaccttcttctacacggcg
gcgatcagtaacaccgtcgatgaactcagaggactccgggacgacgacgactacgacggcgt
ttgtgacaagggtgatgtgtacggtaacggaggaggagaaacgaccaagttgcttaaccttt
tttgtttaa >SEQ_NO_2: AtLBD37 (At5g67420.1) Protein
MSCNGCRVLRKGCSENCILRPCIQWIETADAQGHATVFVAKFFGRAGLMSFISAVPDSQRPA
LFQSLLYEACGRTVNPVNGAIGMLWTGNWNICQAAVETVLRGGSLRPIPELLTHGGGFAGFP
SPTSEEASEICTEMLNLQQNDSTDRNIYHHSRFSSSRSRSTMDSSSPTKRKRLSSEDQPSSE
LDLSLIPNFPIKQATPSSTRRRSVTPSMNSEDSGTTTTTTAFCDKGDVYGNGGGETTKLLNL
FV*

>SEQ_NO_3: AtLBD38 (At3g49940.1) CDS
atgagttgcaatggttgtcgagttctacgaaaaggttgcagtgagaattgcatcctccgtcc
atgtattcaatggatcgaatcacctgaagctcaaggccacgccaccgtcttcgtcgctaagt
tcttcggccgtgccggtttaatgtctttcatctccgccgtaccggaatctcaatgccctgct
ttgtttcagtctttgctatacgaagcttgtgggagaactgtgaatccggtaacggagccgt
cggattgttgtggacggggaattggaatgtttgtcaagcggcggttgagacggtgcttcgtg
gtggttctttaaaaccaataccggagcttcttaacggcggtggattcgccgggtttccgtct
cctacttccgacgaagcttcggagatctgtacggaaatgttgaatctacgaaagctgatga
ttccggtgatcggaacatttatcatcactgccgattctcaagctctagatctagatcaagat
caacagcttctccgccgaaacggaaacgattatcgtcggaacaacaaccttcgtcggagctt
gatctctcttattcctatttatccgattaaaaccttgccgtttaaggaagatacaccgtc
gatgtactcggaggagtctgttaccacggtttcgtttcaaaacaacaacgccggtgatcggt
acgtacgctgcggcggaggaggaggaggagcaacgacaaagttgctcaatctcttcgcttga >SEQ_NO_4: AtLBD38 (At3g49940.1) Protein
MSCNGCRVLRKGCSENCILRPCIQWIESPEAQGHATVFVAKFFGRAGLMSFISAVPESQCPA
LFQSLLYEACGRTVNPVNGAVGLLWTGNWNVCQAAVETVLRGGSLKPIPELLNGGGFAGFPS
PTSDEASEICTEMLNLRKADDSGDRNIYHHCRFSSSRSRSRSTASPPKRKRLSSEQQPSSEL
DLSLIPIYPIKTLPFKEDTPSMYSEESVTTVSFQNNNAGDRYVRCGGGGGATTKLLNLFA*

>SEQ_NO_5: AtLBD39 (At4g37540.1) CDS
Atgagttgcaatggatgtagagttcttcgaaaaggttgcagtgaaacatgcatccttcgtcc
ttgccttcaatggatcgaatccgccgagtcacaaggccacgccaccgtcttcgtcgctaaat
tctttggtcgtgctggtctcatgtctttcatctcctccgtacctgaactccaacgtcctgct

FIG. 6

```
ttgtttcagtcgttgttgtttgaagcgtgtgggagaacggtgaatccggttaacggagcggt
tggtatgttgtggaccaggaactggcacgtatgccaagcggcggttgagactgttcttcgcg
gcggaactttacgaccgatatcagatcttcttgaatctccgtcgttgatgatctcctgtgat
gagtcttcagagatttggcatcaagacgtttcaagaaaccaaacccaccattgtcgcttctc
cacctccagatccacgacggagatgaaagactctctggttaaccgaaaacgattgaagtccg
attcggatcttgatctccaagtgaaccacggtttaaccctaaccgctccggctgtaccggtt
cctttcttcctccgtcgtcgttttgtaaggtggttaagggtgatcgtccgggaagtccatc
ggaggaatctgtaacgacgtcgtgttgggaaaatgggatgagaggagataataaacaaaaaa
gaaacaaggagagaaaaagttattgaacctttttgtttaa >SEQ_NO_6: AtLBD39 (At4g37540.1) Protein
MSCNGCRVLRKGCSETCILRPCLQWIESAESQGHATVFVAKFFGRAGLMSFISSVPELQRPA
LFQSLLFEACGRTVNPVNGAVGMLWTRNWHVCQAAVETVLRGGTLRPISDLLESPSLMISCD
ESSEIWHQDVSRNQTHHCRFSTSRSTTEMKDSLVNRKRLKSDSDLDLQVNHGLTLTAPAVPV
PFLPPSSFCKVVKGDRPGSPSEESVTTSCWENGMRGDNKQKRNKGEKKLLNLFV*
```

```
                66                                                                                       130
AtLBD37*   (66) SLLYEACGRTVNPVNGAIGMLWTGNWNICQAAVETVLRGGSTLRPIPELLITHGGGFAGFPSPTSEE------
SlLBD37*   (66) SLLYEAAGRTVNPVNGAVGLLMTGNWHCQAAVETVLRGGATLRPISEFLG----------ASVEID------
OblBD37*   (66) SLLYEACGRTINPVSGAIGMLWTGNWDICQAAADAVLRGDSLSALSAMPA----------AFT---------
BrLBD37*   (66) SLLYEACGRTVNPVNGAIGMLWTGNWKICQAAVETVLRGGSTLRPIPELLITHGG------GFPSATSEE---
AtLBD38*   (66) SLLYEACGRTVNPVNGVGLLMTGNWNVCQAAVETVLRGGSTKPIPELLNGGG-----FAGFPSTSDE------
SlLBD38*   (66) SLLFEACGRTVNPVTGAVGLLSTGNWHVCQKAVQTVLAGNTRPVLAGILT----------PPYFD-------
BrLBD38*   (49) SLLYEACGRTVNPVNGAVGLLWTGNWSICQAAVETVLRGGSTRPMPELITRDGFGFPSTSDE----------
AtLBD39*   (66) SLLYEACGRTVNPVNGAVGMLWTRNWHVCQAAVETVLRGGTILRPISDLIE---------SPS---------
BrLBD39*   (49) SLLYEACGRTVNPVNGAVGLLWTGNWSICQAAVETVLRGGSTRPMPELLTRDGGFGFPSTTSDE---------
Consensus  (66) SLLYEACGRTVNPVNGAVGLLMTGNW VCQAAVETVLRGGSLRPIPELL        G   GFPS TSDE 131                                                                                     195
AtLBD37*  (131) ASEICTEMLNLQQND-STDRNIYHHSRFSSSRSRSTMDSSIPTKKRLSSEDQPSSELD--LSLI---------
SlLBD37*  (122) EVSDCTDVFKLQDPSLNMRPKMQKRRRSPEETSMLDLSLTPGFNQKVYN--------S--------------
OblBD37*  (119) DRDMAGLYCNVGGASSSSSPAAENSSASAPGGPRRKRARNNGAGER--------------------------
BrLBD37*  (128) ASEICTEMLKLQQNDGSSDRNIYHHSRFSSSRSRSTLDSS-PRKRK-----LE--ISLN-------------
AtLBD38*  (130) ASEICTEMLNLRKADDSGDRNIYHHCRFSSSRS-RSRSTASPPKRKRLSSEQQPSSELD--LSLI--------
SlLBD38*  (122) NSFRCGGAWDMPNQFCN----KSDSMFIDGSEQIEGMEWISS-SEKR--------------------------
BrLBD38*  (114) ASEICTEMLNDCGDR------SAYHHCRFSSSR----TSRPTASPPNRK-----------R-----------
AtLBD39*  (119) LMISCDESSETWHQDVSS-RNQTHHCRFSTSRSTTEMKDSLVNRKRLKSDSDLDLQVNHGLTLTA--------
BrLBD39*  (114) ASEICTEMLNDCGDR------SAYHHCRFSSSR----TSRPTASPPNRK-----------R-----------
Consensus (131) ASEICTEMLNL      S     YHH RFSSSRS TSM  TASP  RK
```

FIG. 7 (continued)

```
                 196                                                            259
AtLBD37* (193) PNFEIKQATPS--STRRRSVTPSMNSEDSGTTTTTAFCD---KGDVYGNGGETTKLLNLFV-
SlLBD37* (172) HPLPEN------HRRPGTPSMNSEES---GTTTCFES---SAVIGDHQGKEPKLLSLFN-
ObLBD37* (165) GH----------QQQIAGGAGASDEHSTTCEEASGDADAGAPTLLNLFS-
BrLBD37* (179) PSLPMK-AVPS--STRQRSRTPSMNSEES--VTTTTFWDNFASGAQHGNGGETSRLLNLFV-
AtLBD38* (192) PIYPIKTLP----FKEDTPSMYSEESVTTVSFQNNAGDRYVRCGGGGATTKLLNLFA-
SlLBD38* (163) WN----------TSSCFGSETELSDVSLGLDSGYGYAECVK---GEEPKLLNLFV-
BrLBD38* (154) LASEQQ-------QR---------------------------------
AtLBD39* (182) RAVPVFLPPSSFCKVVKGDRPGSPSEES---VTTSCWENGMRGDNKQKRNKGEKKLLNLFV-
BrLBD39* (154) LASEQQ-------QR---------------------------------
Consensus(196)  P            R   TPS  SEES     TT                G  G     KLLNLF Overall consensus positions: 66.4%
Overall identity positions:  17.0%
```

FIG. 7 (continued)

SEQUENCE LISTING

```
<160> NUMBER OF SEQ ID NOS: 27

<210> SEQ ID NO 1
<211> LENGTH: 753
<212> TYPE: DNA
<213> ORGANISM: Arabidopsis thaliana

<400> SEQUENCE: 1
atgagctgca atggttgccg tgttctccgg aaaggttgca gcgagaattg tatcctccgg      60
ccatgtattc aatggattga aaccgccgat gctcaaggcc acgccaccgt cttcgtcgct     120
aaattcttcg gccgtgctgg tctcatgtcc tttatctccg ctgttccgga ttctcaacgt     180
cctgctttgt ttcagtcgtt gctctacgaa gcttgtggaa gaactgtcaa tccagttaac     240
ggagcaatcg gaatgttatg gactggaaac tggaatatct gtcaagcggc tgttgaaaca     300
gtgcttcgcg gcggttcttt aagaccgatc ccggagcttc tcactcacgg cggcggtttc     360
gctggctttc cttcgcctac atctgaagaa gcatctgaga tctgcaccga aatgttgaat     420
ctccagcaaa atgattccac cgatcgtaac atctatcatc attcacgatt ctcaagctct     480
agatctagat ctactatgga ttcttcttct ccgacgaaac gtaagagatt atcatcggaa     540
gaccaaccat cttcggagct tgatctatct ctcatcccta attttcccat taagcaagca     600
acaccttctt ctacacggcg gcgatcagta acaccgtcga tgaactcaga ggactccggg     660
acgacgacga ctacgacggc gttttgtgac aagggtgatg tgtacggtaa cggaggagga     720
gaaacgacca agttgcttaa cctttttgtt taa                                  753

<210> SEQ ID NO 2
<211> LENGTH: 250
<212> TYPE: PRT
<213> ORGANISM: Arabidopsis thaliana

<400> SEQUENCE: 2

Met Ser Cys Asn Gly Cys Arg Val Leu Arg Lys Gly Cys Ser Glu Asn
1               5                   10                  15

Cys Ile Leu Arg Pro Cys Ile Gln Trp Ile Glu Thr Ala Asp Ala Gln
            20                  25                  30

Gly His Ala Thr Val Phe Val Ala Lys Phe Phe Gly Arg Ala Gly Leu
        35                  40                  45

Met Ser Phe Ile Ser Ala Val Pro Asp Ser Gln Arg Pro Ala Leu Phe
    50                  55                  60
```

```
Gln Ser Leu Leu Tyr Glu Ala Cys Gly Arg Thr Val Asn Pro Val Asn
 65                  70                  75                  80

Gly Ala Ile Gly Met Leu Trp Thr Gly Asn Trp Asn Ile Cys Gln Ala
                 85                  90                  95

Ala Val Glu Thr Val Leu Arg Gly Gly Ser Leu Arg Pro Ile Pro Glu
            100                 105                 110

Leu Leu Thr His Gly Gly Gly Phe Ala Gly Phe Pro Ser Pro Thr Ser
        115                 120                 125

Glu Glu Ala Ser Glu Ile Cys Thr Glu Met Leu Asn Leu Gln Gln Asn
130                 135                 140

Asp Ser Thr Asp Arg Asn Ile Tyr His His Ser Arg Phe Ser Ser Ser
145                 150                 155                 160

Arg Ser Arg Ser Thr Met Asp Ser Ser Ser Pro Thr Lys Arg Lys Arg
                165                 170                 175

Leu Ser Ser Glu Asp Gln Pro Ser Ser Glu Leu Asp Leu Ser Leu Ile
            180                 185                 190

Pro Asn Phe Pro Ile Lys Gln Ala Thr Pro Ser Ser Thr Arg Arg Arg
        195                 200                 205

Ser Val Thr Pro Ser Met Asn Ser Glu Asp Ser Gly Thr Thr Thr Thr
210                 215                 220

Thr Thr Ala Phe Cys Asp Lys Gly Asp Val Tyr Gly Asn Gly Gly Gly
225                 230                 235                 240

Glu Thr Thr Lys Leu Leu Asn Leu Phe Val
                245                 250

<210> SEQ ID NO 3
<211> LENGTH: 744
<212> TYPE: DNA
<213> ORGANISM: Arabidopsis thaliana

<400> SEQUENCE: 3
atgagttgca atggttgtcg agttctacga aaaggttgca gtgagaattg catcctccgt    60
ccatgtattc aatggatcga atcacctgaa gctcaaggcc acgccaccgt cttcgtcgct   120
aagttcttcg gccgtgccgg tttaatgtct tcatctccg ccgtaccgga atctcaatgc    180
cctgctttgt ttcagtcttt gctatacgaa gcttgtggga gaactgtgaa tccggtgaac   240
ggagccgtcg gattgttgtg gacggggaat tggaatgttt gtcaagcggc ggttgagacg   300
gtgcttcgtg gtggttcttt aaaaccaata ccggagcttc ttaacggcgg tggattcgcc   360
gggtttccgt ctcctacttc cgacgaagct tcggagatct gtacggaaat gttgaatcta   420
cgaaaagctg atgattccgg tgatcggaac atttatcatc actgccgatt ctcaagctct   480
agatctagat caagatcaac agcttctccg ccgaaacgga aacgattatc gtcggaacaa   540
caaccttcgt cggagcttga tctctctctt attcctattt atccgattaa accttgccg    600 tttaaggaag atacaccgtc gatgtactcg gaggagtctg ttaccacggt ttcgtttcaa   660
aacaacaacg ccggtgatcg gtacgtacgc tgcggcggag gaggaggagg agcaacgaca   720
aagttgctca atctcttcgc ttga                                          744

<210> SEQ ID NO 4
<211> LENGTH: 247
<212> TYPE: PRT
<213> ORGANISM: Arabidopsis thaliana

<400> SEQUENCE: 4
```

| Met | Ser | Cys | Asn | Gly | Cys | Arg | Val | Leu | Arg | Lys | Gly | Cys | Ser | Glu | Asn |
|---|---|---|---|---|---|---|---|---|---|---|---|---|---|---|---|
| 1 | | | | 5 | | | | | 10 | | | | | 15 | |

Cys Ile Leu Arg Pro Cys Ile Gln Trp Ile Glu Ser Pro Glu Ala Gln
             20                   25                   30

Gly His Ala Thr Val Phe Val Ala Lys Phe Phe Gly Arg Ala Gly Leu
           35                   40                   45

Met Ser Phe Ile Ser Ala Val Pro Glu Ser Gln Cys Pro Ala Leu Phe
   50                   55                   60

Gln Ser Leu Leu Tyr Glu Ala Cys Gly Arg Thr Val Asn Pro Val Asn
65                 70                   75               80

Gly Ala Val Gly Leu Leu Trp Thr Gly Asn Trp Asn Val Cys Gln Ala
               85                   90               95

Ala Val Glu Thr Val Leu Arg Gly Gly Ser Leu Lys Pro Ile Pro Glu
         100                  105                110

Leu Leu Asn Gly Gly Phe Ala Gly Phe Pro Ser Pro Thr Ser Asp
          115                 120              125

Glu Ala Ser Glu Ile Cys Thr Glu Met Leu Asn Leu Arg Lys Ala Asp
     130                 135                140

Asp Ser Gly Asp Arg Asn Ile Tyr His His Cys Arg Phe Ser Ser Ser
145                150                 155            160

Arg Ser Arg Ser Arg Ser Thr Ala Ser Pro Pro Lys Arg Lys Arg Leu
         165                  170               175

Ser Ser Glu Gln Gln Pro Ser Ser Glu Leu Asp Leu Ser Leu Ile Pro
         180                  185              190

Ile Tyr Pro Ile Lys Thr Leu Pro Phe Lys Glu Asp Thr Pro Ser Met
         195                  200              205

Tyr Ser Glu Glu Ser Val Thr Thr Val Ser Phe Gln Asn Asn Asn Ala
     210                 215                220

Gly Asp Arg Tyr Val Arg Cys Gly Gly Gly Gly Gly Ala Thr Thr
225                230                 235            240

Lys Leu Leu Asn Leu Phe Ala
         245

```
<210> SEQ ID NO 5
<211> LENGTH: 723
<212> TYPE: DNA
<213> ORGANISM: Arabidopsis thaliana

<400> SEQUENCE: 5
atgagttgca atggatgtag agttcttcga aaaggttgca gtgaaacatg catccttcgt        60
ccttgccttc aatggatcga atccgccgag tcacaaggcc acgccaccgt cttcgtcgct       120
aaattctttg gtcgtgctgg tctcatgtct ttcatctcct ccgtacctga actccaacgt       180
cctgctttgt ttcagtcgtt gttgtttgaa gcgtgtggga gaacggtgaa tccggttaac       240
ggagcggttg gtatgttgtg gaccaggaac tggcacgtat gccaagcggc ggttgagact       300
gttcttcgcg gcggaacttt acgaccgata tcagatcttc ttgaatctcc gtcgttgatg       360
atctcctgtg atgagtcttc agagatttgg catcaagacg tttcaagaaa ccaaacccac       420
cattgtcgct tctccacctc cagatccacg acggagatga agactctct ggttaaccga       480 aaacgattga agtccgattc ggatcttgat ctccaagtga ccacggtttt aaccctaacc       540
gctccggctg taccggttcc tttcttcct ccgtcgtcgt tttgtaaggt ggttaagggt       600
gatcgtccgg gaagtccatc ggaggaatct gtaacgacgt cgtgtgggga aaatgggatg       660
agaggagata ataaacaaaa agaaacaaa ggagagaaaa agttattgaa ccttttttgtt       720
``` taa                                                                            723

<210> SEQ ID NO 6
<211> LENGTH: 240
<212> TYPE: PRT
<213> ORGANISM: Arabidopsis thaliana

<400> SEQUENCE: 6

Met Ser Cys Asn Gly Cys Arg Val Leu Arg Lys Gly Cys Ser Glu Thr
1               5                   10                  15

Cys Ile Leu Arg Pro Cys Leu Gln Trp Ile Glu Ser Ala Glu Ser Gln
            20                  25                  30

Gly His Ala Thr Val Phe Val Ala Lys Phe Phe Gly Arg Ala Gly Leu
        35                  40                  45

Met Ser Phe Ile Ser Ser Val Pro Glu Leu Gln Arg Pro Ala Leu Phe
    50                  55                  60

Gln Ser Leu Leu Phe Glu Ala Cys Gly Arg Thr Val Asn Pro Val Asn
65                  70                  75                  80

Gly Ala Val Gly Met Leu Trp Thr Arg Asn Trp His Val Cys Gln Ala
                85                  90                  95

Ala Val Glu Thr Val Leu Arg Gly Gly Thr Leu Arg Pro Ile Ser Asp
            100                 105                 110

Leu Leu Glu Ser Pro Ser Leu Met Ile Ser Cys Asp Glu Ser Ser Glu
        115                 120                 125

Ile Trp His Gln Asp Val Ser Arg Asn Gln Thr His His Cys Arg Phe
    130                 135                 140

Ser Thr Ser Arg Ser Thr Thr Glu Met Lys Asp Ser Leu Val Asn Arg
145                 150                 155                 160

Lys Arg Leu Lys Ser Asp Ser Asp Leu Asp Leu Gln Val Asn His Gly
                165                 170                 175

Leu Thr Leu Thr Ala Pro Ala Val Pro Val Pro Phe Leu Pro Pro Ser
            180                 185                 190

Ser Phe Cys Lys Val Val Lys Gly Asp Arg Pro Gly Ser Pro Ser Glu
        195                 200                 205

Glu Ser Val Thr Thr Ser Cys Trp Glu Asn Gly Met Arg Gly Asp Asn
    210                 215                 220

Lys Gln Lys Arg Asn Lys Gly Glu Lys Lys Leu Leu Asn Leu Phe Val
225                 230                 235                 240

<210> SEQ ID NO 7
<211> LENGTH: 14
<212> TYPE: PRT
<213> ORGANISM: Artificial Sequence
<220> FEATURE:
<223> OTHER INFORMATION: Sequence motif
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid

<400> SEQUENCE: 7

Met Ser Cys Asn Gly Cys Arg Xaa Leu Arg Lys Gly Cys Xaa
1               5                   10

<210> SEQ ID NO 8

```
<211> LENGTH: 14
<212> TYPE: PRT
<213> ORGANISM: Artificial Sequence
<220> FEATURE:
<223> OTHER INFORMATION: Sequence motif
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid

<400> SEQUENCE: 8

Gln Xaa Xaa Ala Thr Xaa Phe Xaa Ala Lys Phe Xaa Gly Arg
1               5                   10

<210> SEQ ID NO 9
<211> LENGTH: 10
<212> TYPE: PRT
<213> ORGANISM: Artificial Sequence
<220> FEATURE:
<223> OTHER INFORMATION: Sequence motif
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid

<400> SEQUENCE: 9

Phe Xaa Ser Leu Leu Xaa Glu Ala Xaa Gly
1               5                   10

<210> SEQ ID NO 10
<211> LENGTH: 15
<212> TYPE: PRT
<213> ORGANISM: Artificial Sequence
<220> FEATURE:
<223> OTHER INFORMATION: C motif
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(10)
<223> OTHER INFORMATION: Xaa can be any naturally occurring amino acid
<220> FEATURE:
<221> NAME/KEY: misc_feature
<222> LOCATION: (12)..(14)
<223> OTHER INFORMATION: Xaa can be any naturally occurring amino acid

<400> SEQUENCE: 10

Cys Xaa Xaa Cys Xaa Xaa Xaa Xaa Xaa Xaa Cys Xaa Xaa Xaa Cys
1               5                   10                  15

<210> SEQ ID NO 11
```

```
<211> LENGTH: 250
<212> TYPE: PRT
<213> ORGANISM: Arabidopsis thaliana

<400> SEQUENCE: 11
```

| | | | | | | | | | | | | | | | |
|---|---|---|---|---|---|---|---|---|---|---|---|---|---|---|---|
| Met | Ser | Cys | Asn | Gly | Cys | Arg | Val | Leu | Arg | Lys | Gly | Cys | Ser | Glu | Asn |
| 1 | | | | 5 | | | | | 10 | | | | | 15 | |
| Cys | Ile | Leu | Arg | Pro | Cys | Ile | Gln | Trp | Ile | Glu | Thr | Ala | Asp | Ala | Gln |
| | | | 20 | | | | | 25 | | | | | 30 | | |
| Gly | His | Ala | Thr | Val | Phe | Val | Ala | Lys | Phe | Phe | Gly | Arg | Ala | Gly | Leu |
| | | 35 | | | | | 40 | | | | | 45 | | | |
| Met | Ser | Phe | Ile | Ser | Ala | Val | Pro | Asp | Ser | Gln | Arg | Pro | Ala | Leu | Phe |
| 50 | | | | | 55 | | | | | 60 | | | | | |
| Gln | Ser | Leu | Leu | Tyr | Glu | Ala | Cys | Gly | Arg | Thr | Val | Asn | Pro | Val | Asn |
| 65 | | | | | 70 | | | | | 75 | | | | | 80 |
| Gly | Ala | Ile | Gly | Met | Leu | Trp | Thr | Gly | Asn | Trp | Asn | Ile | Cys | Gln | Ala |
| | | | | 85 | | | | | 90 | | | | | 95 | |
| Ala | Val | Glu | Thr | Val | Leu | Arg | Gly | Gly | Ser | Leu | Arg | Pro | Ile | Pro | Glu |
| | | | 100 | | | | | 105 | | | | | 110 | | |
| Leu | Leu | Thr | His | Gly | Gly | Phe | Ala | Gly | Phe | Pro | Ser | Pro | Thr | Ser | |
| | | 115 | | | | | 120 | | | | | 125 | | | |
| Glu | Glu | Ala | Ser | Glu | Ile | Cys | Thr | Glu | Met | Leu | Asn | Leu | Gln | Gln | Asn |
| | | 130 | | | | | 135 | | | | | 140 | | | |
| Asp | Ser | Thr | Asp | Arg | Asn | Ile | Tyr | His | His | Ser | Arg | Phe | Ser | Ser | Ser |
| 145 | | | | | 150 | | | | | 155 | | | | | 160 |
| Arg | Ser | Arg | Ser | Thr | Met | Asp | Ser | Ser | Ser | Pro | Thr | Lys | Arg | Lys | Arg |
| | | | | 165 | | | | | 170 | | | | | 175 | |
| Leu | Ser | Ser | Glu | Asp | Gln | Pro | Ser | Ser | Glu | Leu | Asp | Leu | Ser | Leu | Ile |
| | | | 180 | | | | | 185 | | | | | 190 | | |
| Pro | Asn | Phe | Pro | Ile | Lys | Gln | Ala | Thr | Pro | Ser | Ser | Thr | Arg | Arg | Arg |
| | | | 195 | | | | | 200 | | | | | 205 | | |
| Ser | Val | Thr | Pro | Ser | Met | Asn | Ser | Glu | Asp | Ser | Gly | Thr | Thr | Thr | Thr |
| | 210 | | | | | 215 | | | | | 220 | | | | |
| Thr | Thr | Ala | Phe | Cys | Asp | Lys | Gly | Asp | Val | Tyr | Gly | Asn | Gly | Gly | Gly |
| 225 | | | | | 230 | | | | | 235 | | | | | 240 |
| Glu | Thr | Thr | Lys | Leu | Leu | Asn | Leu | Phe | Val | | | | | | |
| | | | | 245 | | | | | 250 | | | | | | |

```
<210> SEQ ID NO 12
<211> LENGTH: 217
<212> TYPE: PRT
<213> ORGANISM: Solanum lycopersicum

<400> SEQUENCE: 12
```

| | | | | | | | | | | | | | | | |
|---|---|---|---|---|---|---|---|---|---|---|---|---|---|---|---|
| Met | Ser | Cys | Asn | Gly | Cys | Arg | Val | Leu | Arg | Lys | Gly | Cys | Ser | Asp | Asn |
| 1 | | | | 5 | | | | | 10 | | | | | 15 | |
| Cys | Ile | Leu | Arg | Pro | Cys | Leu | Gln | Trp | Ile | Glu | Thr | Pro | Glu | Ala | Gln |
| | | | 20 | | | | | 25 | | | | | 30 | | |
| Gly | His | Ala | Thr | Val | Phe | Val | Ala | Lys | Phe | Phe | Gly | Arg | Ala | Gly | Leu |
| | | 35 | | | | | 40 | | | | | 45 | | | |
| Met | Ser | Phe | Ile | Ser | Ala | Val | Pro | Glu | Asn | Gln | Arg | Pro | Ala | Leu | Phe |
| 50 | | | | | 55 | | | | | 60 | | | | | |
| Gln | Ser | Leu | Leu | Tyr | Glu | Ala | Ala | Gly | Arg | Thr | Val | Asn | Pro | Val | Asn |
| 65 | | | | | 70 | | | | | 75 | | | | | 80 |
| Gly | Ala | Val | Gly | Leu | Leu | Trp | Thr | Gly | Asn | Trp | His | Val | Cys | Gln | Ala |
| | | | | 85 | | | | | 90 | | | | | 95 | |

```
Ala Val Glu Thr Val Leu Arg Gly Gly Ala Leu Arg Pro Ile Ser Glu
            100                 105                 110

Phe Leu Gly Ala Ser Val Glu Ile Asp Glu Val Ser Asp Cys Thr Asp
            115                 120                 125

Val Phe Lys Leu Gln Asp Pro Ser Leu Asn Met Arg Pro Lys Met Gln
130                 135                 140

Lys Arg Arg Arg Ser Pro Glu Glu Thr Ser Met Leu Asp Leu Ser Leu
145                 150                 155                 160

Thr Pro Gly Phe Asn Gln Lys Val Tyr Asn Ser His Pro Leu Pro Glu
                165                 170                 175

His Arg Arg Pro Gly Thr Pro Ser Met Asn Ser Glu Glu Ser Gly Thr
            180                 185                 190

Thr Thr Cys Phe Glu Ser Ser Ala Val Ile Gly Asp His Gln Gly Lys
            195                 200                 205

Glu Pro Lys Leu Leu Ser Leu Phe Asn
        210                 215

<210> SEQ ID NO 13
<211> LENGTH: 205
<212> TYPE: PRT
<213> ORGANISM: Oryza brachyantha

<400> SEQUENCE: 13

Met Ser Cys Asn Gly Cys Arg Val Leu Arg Lys Gly Cys Ser Asp Ala
1               5                   10                  15

Cys Val Leu Arg Pro Ser Ile Glu Trp Ile Asp Gly Ala Gln Pro Gln
            20                  25                  30

Ala Asn Ala Thr Val Phe Val Ala Lys Phe Phe Gly Arg Ala Gly Leu
        35                  40                  45

Val Ala Ser Leu Ala Ala Val Pro Leu His His Arg Pro Ala Leu Phe
    50                  55                  60

Gln Ser Leu Leu Tyr Glu Ala Cys Gly Arg Thr Ile Asn Pro Val Ser
65                  70                  75                  80

Gly Ala Ile Gly Leu Met Trp Thr Gly Asn Trp Asp Leu Cys Gln Ala
                85                  90                  95

Ala Ala Asp Ala Val Leu Arg Gly Asp Ser Leu Ser Ala Leu Ser Ala
            100                 105                 110

Val Pro Ala Ala Phe Thr Asp Arg Asp Met Ala Gly Leu Tyr Gly Asn
        115                 120                 125

Val Gly Gly Ala Ser Ser Ser Ser Pro Ala Ala Glu Asn Ser Ser
    130                 135                 140

Ala Ser Ala Pro Gly Gly Pro Arg Arg Lys Arg Ala Arg Asn Gly
145                 150                 155                 160

Ala Gly Glu Arg Gly His Gln Gln Gln Leu Ala Ala Gly Gly Ala Gly
                165                 170                 175

Ala Ser Asp Glu His Ser Thr Thr Thr Cys Glu Glu Ala Ser Gly Asp
            180                 185                 190

Ala Asp Ala Gly Ala Pro Thr Leu Leu Asn Leu Phe Ser
        195                 200                 205

<210> SEQ ID NO 14
<211> LENGTH: 236
<212> TYPE: PRT
<213> ORGANISM: Brassica rapa

<400> SEQUENCE: 14
```

Met Ser Cys Asn Gly Cys Arg Val Leu Arg Lys Gly Cys Ser Glu Asn
1               5                   10                  15

Cys Ile Leu Arg Pro Cys Ile Gln Trp Ile Glu Thr Ala Asp Ala Gln
            20                  25                  30

Gly His Ala Thr Val Phe Val Ala Lys Phe Phe Gly Arg Ala Gly Leu
        35                  40                  45

Met Ser Phe Ile Ser Ala Val Pro Glu Ser Gln Arg Pro Ala Leu Phe
50                  55                  60

Gln Ser Leu Leu Tyr Glu Ala Cys Gly Arg Thr Val Asn Pro Val Asn
65                  70                  75                  80

Gly Ala Ile Gly Met Leu Trp Thr Gly Asn Trp Lys Val Cys Gln Ala
                85                  90                  95

Ala Val Glu Thr Val Leu Arg Gly Gly Ser Leu Arg Pro Ile Pro Glu
            100                 105                 110

Leu Leu Thr His Gly Gly Gly Phe Pro Ser Ala Thr Ser Glu Glu Ala
            115                 120                 125

Ser Glu Ile Cys Thr Glu Met Leu Lys Leu Gln Gln Asn Asp Gly Ser
        130                 135                 140

Ser Asp Arg Asn Ile Tyr His His Ser Arg Phe Ser Ser Ser Arg Ser
145                 150                 155                 160

Arg Ser Thr Leu Asp Ser Ser Pro Arg Lys Arg Lys Leu Glu Ile Ser
                165                 170                 175

Leu Asn Pro Ser Leu Pro Met Lys Ala Val Pro Ser Ser Thr Arg Gln
            180                 185                 190

Arg Ser Arg Thr Pro Ser Met Asn Ser Glu Glu Ser Val Thr Thr Thr
        195                 200                 205

Thr Thr Phe Trp Asp Asn Phe Ala Ser Gly Ala Gln His Gly Asn Gly
    210                 215                 220

Gly Gly Glu Thr Ser Arg Leu Leu Asn Leu Phe Val
225                 230                 235

<210> SEQ ID NO 15
<211> LENGTH: 247
<212> TYPE: PRT
<213> ORGANISM: Arabidopsis thaliana

<400> SEQUENCE: 15

Met Ser Cys Asn Gly Cys Arg Val Leu Arg Lys Gly Cys Ser Glu Asn
1               5                   10                  15

Cys Ile Leu Arg Pro Cys Ile Gln Trp Ile Glu Ser Pro Glu Ala Gln
            20                  25                  30

Gly His Ala Thr Val Phe Val Ala Lys Phe Phe Gly Arg Ala Gly Leu
        35                  40                  45

Met Ser Phe Ile Ser Ala Val Pro Glu Ser Gln Cys Pro Ala Leu Phe
50                  55                  60

Gln Ser Leu Leu Tyr Glu Ala Cys Gly Arg Thr Val Asn Pro Val Asn
65                  70                  75                  80

Gly Ala Val Gly Leu Leu Trp Thr Gly Asn Trp Asn Val Cys Gln Ala
                85                  90                  95

Ala Val Glu Thr Val Leu Arg Gly Gly Ser Leu Lys Pro Ile Pro Glu
            100                 105                 110

Leu Leu Asn Gly Gly Phe Ala Gly Phe Pro Ser Pro Thr Ser Asp
            115                 120                 125

Glu Ala Ser Glu Ile Cys Thr Glu Met Leu Asn Leu Arg Lys Ala Asp

```
                130             135             140
Asp Ser Gly Asp Arg Asn Ile Tyr His His Cys Arg Phe Ser Ser Ser
145                 150                 155                 160

Arg Ser Arg Ser Arg Ser Thr Ala Ser Pro Pro Lys Arg Lys Arg Leu
                165                 170                 175

Ser Ser Glu Gln Gln Pro Ser Ser Glu Leu Asp Leu Ser Leu Ile Pro
            180                 185                 190

Ile Tyr Pro Ile Lys Thr Leu Pro Phe Lys Glu Asp Thr Pro Ser Met
        195                 200                 205

Tyr Ser Glu Glu Ser Val Thr Thr Val Ser Phe Gln Asn Asn Asn Ala
    210                 215                 220

Gly Asp Arg Tyr Val Arg Cys Gly Gly Gly Gly Gly Ala Thr Thr
225                 230                 235                 240

Lys Leu Leu Asn Leu Phe Ala
                245

<210> SEQ ID NO 16
<211> LENGTH: 204
<212> TYPE: PRT
<213> ORGANISM: Solanum lycopersicum

<400> SEQUENCE: 16

Met Ser Cys Asn Gly Cys Arg Val Leu Arg Arg Cys Ser Asp Asn
1               5                   10                  15

Cys Thr Leu Arg Thr Cys Leu Asp Gly Ile Asp Asp Pro Gln Ala Gln
                20                  25                  30

Gly Asn Ala Thr Leu Phe Val Ser Lys Phe Phe Gly Arg Ser Asp Leu
            35                  40                  45

Met Ser Leu Ile Ala Ala Val Pro Gln Asn Arg Arg Pro Ala Leu Phe
    50                  55                  60

Lys Ser Leu Leu Phe Glu Ala Cys Gly Arg Thr Val Asn Pro Val Thr
65                  70                  75                  80

Gly Ala Val Gly Leu Leu Ser Thr Gly Asn Trp His Val Cys Gln Lys
                85                  90                  95

Ala Val Gln Thr Val Leu Ala Gly Gly Asn Leu Arg Pro Val Leu Ala
                100                 105                 110

Gly Ile Leu Thr Pro Pro Tyr Phe Asp Asn Ser Phe Arg Cys Gly Gly
            115                 120                 125

Ala Trp Asp Met Pro Asn Gln Phe Cys Asn Lys Ser Asp Ser Met Phe
    130                 135                 140

Ile Asp Gly Ser Glu Gln Ile Glu Gly Met Glu Trp Ile Ser Ser Glu
145                 150                 155                 160

Lys Arg Trp Asn Thr Ser Ser Cys Phe Gly Ser Glu Thr Glu Leu Ser
                165                 170                 175

Asp Val Ser Leu Gly Leu Asp Ser Gly Tyr Gly Tyr Ala Glu Cys Val
            180                 185                 190

Lys Gly Glu Glu Pro Lys Leu Leu Asn Leu Phe Val
        195                 200

<210> SEQ ID NO 17
<211> LENGTH: 161
<212> TYPE: PRT
<213> ORGANISM: Brassica rapa

<400> SEQUENCE: 17

Ile Leu Arg Pro Cys Ile Gln Trp Ile Glu Ser Ala Glu Ala Gln Gly
```

-continued

```
1               5                   10                  15
His Ala Thr Val Phe Val Ala Lys Phe Phe Gly Arg Ala Gly Leu Met
                20                  25                  30

Ser Phe Ile Ser Ser Val Pro Glu Ser Gln Ser Pro Ala Leu Phe Gln
                35                  40                  45

Ser Leu Leu Tyr Glu Ala Cys Gly Arg Thr Val Asn Pro Val Asn Gly
                50                  55                  60

Ala Val Gly Leu Leu Trp Thr Gly Asn Trp Ser Ile Cys Gln Ala Ala
65                  70                  75                  80

Val Glu Thr Val Leu Arg Gly Gly Ser Leu Arg Pro Met Pro Glu Leu
                85                  90                  95

Leu Thr Arg Asp Gly Gly Phe Gly Gly Phe Pro Ser Thr Thr Ser Asp
                100                 105                 110

Glu Ala Ser Glu Ile Cys Thr Glu Met Leu Asn Asp Cys Gly Asp Arg
                115                 120                 125

Ser Ala Tyr His His Cys Arg Phe Ser Ser Arg Thr Ser Arg Pro
                130                 135                 140

Thr Ala Ser Pro Pro Asn Arg Lys Arg Leu Ala Ser Glu Gln Gln Gln
145                 150                 155                 160

Arg
```

<210> SEQ ID NO 18
<211> LENGTH: 240
<212> TYPE: PRT
<213> ORGANISM: Arabidopsis thaliana

<400> SEQUENCE: 18

```
Met Ser Cys Asn Gly Cys Arg Val Leu Arg Lys Gly Cys Ser Glu Thr
1               5                   10                  15

Cys Ile Leu Arg Pro Cys Leu Gln Trp Ile Glu Ser Ala Glu Ser Gln
                20                  25                  30

Gly His Ala Thr Val Phe Val Ala Lys Phe Phe Gly Arg Ala Gly Leu
                35                  40                  45

Met Ser Phe Ile Ser Ser Val Pro Glu Leu Gln Arg Pro Ala Leu Phe
                50                  55                  60

Gln Ser Leu Leu Phe Glu Ala Cys Gly Arg Thr Val Asn Pro Val Asn
65                  70                  75                  80

Gly Ala Val Gly Met Leu Trp Thr Arg Asn Trp His Val Cys Gln Ala
                85                  90                  95

Ala Val Glu Thr Val Leu Arg Gly Gly Thr Leu Arg Pro Ile Ser Asp
                100                 105                 110

Leu Leu Glu Ser Pro Ser Leu Met Ile Ser Cys Asp Glu Ser Ser Glu
                115                 120                 125

Ile Trp His Gln Asp Val Ser Arg Asn Gln Thr His His Cys Arg Phe
                130                 135                 140

Ser Thr Ser Arg Ser Thr Thr Glu Met Lys Asp Ser Leu Val Asn Arg
145                 150                 155                 160

Lys Arg Leu Lys Ser Asp Ser Asp Leu Asp Leu Gln Val Asn His Gly
                165                 170                 175

Leu Thr Leu Thr Ala Pro Ala Val Pro Val Pro Phe Leu Pro Pro Ser
                180                 185                 190

Ser Phe Cys Lys Val Val Lys Gly Asp Arg Pro Gly Ser Pro Ser Glu
                195                 200                 205

Glu Ser Val Thr Thr Ser Cys Trp Glu Asn Gly Met Arg Gly Asp Asn
```

```
                210               215                 220
Lys Gln Lys Arg Asn Lys Gly Glu Lys Leu Leu Asn Leu Phe Val
225                 230                 235                 240
```

```
<210> SEQ ID NO 19
<211> LENGTH: 161
<212> TYPE: PRT
<213> ORGANISM: Brassica rapa

<400> SEQUENCE: 19

Ile Leu Arg Pro Cys Ile Gln Trp Ile Glu Ser Ala Glu Ala Gln Gly
1               5                   10                  15

His Ala Thr Val Phe Val Ala Lys Phe Gly Arg Ala Gly Leu Met
            20                  25                  30

Ser Phe Ile Ser Ser Val Pro Glu Ser Gln Ser Pro Ala Leu Phe Gln
        35                  40                  45

Ser Leu Leu Tyr Glu Ala Cys Gly Arg Thr Val Asn Pro Val Asn Gly
    50                  55                  60

Ala Val Gly Leu Leu Trp Thr Gly Asn Trp Ser Ile Cys Gln Ala Ala
65                  70                  75                  80

Val Glu Thr Val Leu Arg Gly Gly Ser Leu Arg Pro Met Pro Glu Leu
                85                  90                  95

Leu Thr Arg Asp Gly Gly Phe Gly Gly Phe Pro Ser Thr Thr Ser Asp
            100                 105                 110

Glu Ala Ser Glu Ile Cys Thr Glu Met Leu Asn Asp Cys Gly Asp Arg
        115                 120                 125

Ser Ala Tyr His His Cys Arg Phe Ser Ser Ser Arg Thr Ser Arg Pro
    130                 135                 140

Thr Ala Ser Pro Pro Asn Arg Lys Arg Leu Ala Ser Glu Gln Gln Gln
145                 150                 155                 160

Arg
```

```
<210> SEQ ID NO 20
<211> LENGTH: 91
<212> TYPE: PRT
<213> ORGANISM: Artificial Sequence
<220> FEATURE:
<223> OTHER INFORMATION: Consensus sequence

<400> SEQUENCE: 20

Met Ser Cys Asn Gly Cys Arg Val Leu Arg Lys Gly Cys Ser Glu Asn
1               5                   10                  15

Cys Ile Leu Arg Pro Cys Ile Gln Trp Ile Glu Ser Ala Glu Ala Gln
            20                  25                  30

Gly His Ala Thr Val Phe Val Ala Lys Phe Phe Gly Arg Ala Gly Leu
        35                  40                  45

Met Ser Phe Ile Ser Ala Val Pro Glu Ser Gln Arg Pro Ala Leu Phe
    50                  55                  60

Gln Ser Leu Leu Tyr Glu Ala Cys Gly Arg Thr Val Asn Pro Val Asn
65                  70                  75                  80

Gly Ala Val Gly Leu Leu Trp Thr Gly Asn Trp
                85                  90
```

```
<210> SEQ ID NO 21
<211> LENGTH: 22
<212> TYPE: PRT
<213> ORGANISM: Artificial Sequence
<220> FEATURE:
```

<223> OTHER INFORMATION: Consensus sequence

<400> SEQUENCE: 21

Val Cys Gln Ala Ala Val Glu Thr Val Leu Arg Gly Gly Ser Leu Arg
1               5                   10                  15

Pro Ile Pro Glu Leu Leu
            20

<210> SEQ ID NO 22
<211> LENGTH: 4
<212> TYPE: PRT
<213> ORGANISM: Artificial Sequence
<220> FEATURE:
<223> OTHER INFORMATION: Consensus sequence

<400> SEQUENCE: 22

Gly Phe Pro Ser
1

<210> SEQ ID NO 23
<211> LENGTH: 15
<212> TYPE: PRT
<213> ORGANISM: Artificial Sequence
<220> FEATURE:
<223> OTHER INFORMATION: Consensus sequence

<400> SEQUENCE: 23

Thr Ser Asp Glu Ala Ser Glu Ile Cys Thr Glu Met Leu Asn Leu
1               5                   10                  15

<210> SEQ ID NO 24
<211> LENGTH: 7
<212> TYPE: PRT
<213> ORGANISM: Artificial Sequence
<220> FEATURE:
<223> OTHER INFORMATION: Consensus sequence

<400> SEQUENCE: 24

Arg Phe Ser Ser Ser Arg Ser
1               5

<210> SEQ ID NO 25
<211> LENGTH: 4
<212> TYPE: PRT
<213> ORGANISM: Artificial Sequence
<220> FEATURE:
<223> OTHER INFORMATION: Consensus sequence

<400> SEQUENCE: 25

Thr Ala Ser Pro
1

<210> SEQ ID NO 26
<211> LENGTH: 4
<212> TYPE: PRT
<213> ORGANISM: Artificial Sequence
<220> FEATURE:
<223> OTHER INFORMATION: Consensus sequence

<400> SEQUENCE: 26

Ser Glu Glu Ser
1

<210> SEQ ID NO 27
<211> LENGTH: 6
<212> TYPE: PRT

```
<213> ORGANISM: Artificial Sequence
<220> FEATURE:
<223> OTHER INFORMATION: Consensus sequence

<400> SEQUENCE: 27

Lys Leu Leu Asn Leu Phe
1               5
```

METHOD FOR THE REDUCTION OF TOBACCO-SPECIFIC NITROSAMINES OR THEIR PRECURSORS IN TOBACCO PLANTS

CROSS-REFERENCE TO RELATED APPLICATIONS

This application is the National Stage of International Application No. PCT/GB2016/050260, filed Feb. 4, 2016, which claims priority to and benefit of Great Britain Patent Application No. 1501941.7, filed Feb. 5, 2015, all of which are herein incorporated by reference in their entirety for all purposes.

FIELD OF THE INVENTION

The present invention relates to the reduction of tobacco-specific nitrosamines or their precursors in tobacco plants. In particular the invention relates to methods and uses of lateral bound domain (LBD) nitrogen-responsive transcription factors and to tobacco plants and their downstream products (e.g. propagation materials, harvested leaf, processed tobacco and tobacco products).

BACKGROUND

Tobacco-specific nitrosamines (TSNA) are formed from nicotine and related compounds by a nitrosation reaction that occurs during the curing and processing of tobacco, as illustrated in FIG. 1. The nitrosating agent in air-cured tobacco is usually nitrite derived from the reduction of leaf nitrate by the action of microbes during curing, and production of nitrosamine has been shown to correlate to high levels of nitrate/nitrite and nitric oxide (Liang S., Yang J., Zhou J., Yu J., Ma Y., Bai R., Xu F., Yang C. Application of exogenous substances reduces tobacco-specific nitrosamines content by regulating biosynthesis of nicotine and nitrite in burley tobacco. Acta Physiol. Plant. (2013) 35: 3027-3036; Shi H., Wang R., Bush L. P., Yang H., Fannin F. F. The relationships between TSNAs and their precursors in burley tobacco from regions and varieties. Journal of Food, Agriculture & Environment (2012) 10 (3&4): 1048-1052). TSNA reduction is a desirable aim for the tobacco industry.

Nitrogen (N) and nitrate ($NO_3^-$) availability regulate many aspects of plant metabolism, growth and development. The plant-specific lateral organ boundaries domain (LBD) gene family is essential to the regulation of plant lateral organ development and is also involved in the regulation of nitrogen metabolism. Three $N/NO_3^-$-induced members of the LBD gene family of transcription factors (LBD37, LBD38 and LBD39) act as negative regulators of anthocyanin biosynthesis in *Arabidopsis thaliana* (Rubin G., Tohge T., Matsuda F., Saito K., Scheible W-R. Members of the LBD Family of transcription factors repress anthocyanin synthesis and affect additional nitrogen responses in *Arabidopsis*. Plant Cell (2009) 21 (11): 3567-3584). It is thought that LBD37-39 signal N availability to the plant system, leading to repression of specific N deficiency responses, such as anthocyanin synthesis. The LBD genes also repress many other known N-responsive genes, including key genes required for $NO_3^-$ uptake and assimilation, resulting in altered $NO_3^-$ content, nitrate reductase activity/activation, protein, amino acid and starch levels, anthocyanin biosynthesis and N-related growth phenotypes (Rubin et al., 2009).

SUMMARY OF THE INVENTION

According to a first aspect the present invention provides a method for reducing at least one tobacco-specific nitrosamine (TSNA) or a precursor thereto in a tobacco plant comprising modifying the plant by increasing the activity or expression of a LBD (lateral organ bound domain) nitrogen-responsive transcription factor in said tobacco plant.

In another aspect there is provided the use of a LBD nitrogen-responsive transcription factor in a tobacco plant for the reduction of at least one TSNA or a precursor thereto.

The present invention provides in a further aspect a method for producing a tobacco plant, a tobacco plant propagation material, a tobacco leaf, a cut harvested tobacco leaf, a processed tobacco leaf or a cut processed tobacco leaf which has a reduction in at least one TSNA or a precursor thereto, the method comprising modifying said tobacco plant to increase the activity or expression of a LBD nitrogen-responsive transcription factor.

In another aspect there is provided a construct or vector comprising a nucleic acid encoding a LBD nitrogen-responsive transcription factor operably linked with a leaf-specific promoter or leaf-preferred promoter. The invention also provides a construct or vector comprising a nucleic acid encoding a LBD nitrogen-responsive transcription factor operably linked with a senescence-specific promoter.

In a further aspect there is provided a tobacco cell:
i) comprising an exogenous LBD nitrogen-responsive transcription factor;
ii) comprising a construct or vector of the invention; and/or
iii) obtainable (e.g obtained) by a method or use of the invention.

The invention provides in another aspect a tobacco plant:
i) which has been modified to achieve a reduction in at least one TSNA or a precursor thereto in comparison to an unmodified plant, wherein the modification is an increase in activity or expression of a LBD nitrogen-responsive transcription factor in said modified plant;
ii) comprising an exogenous LBD nitrogen-responsive transcription factor;
iii) obtainable by a method or use according to the invention;
iv) comprising a construct or vector according to the invention; and/or
v) comprising a cell according to the invention.

In a further aspect there is provided a tobacco plant propagation material (e.g. a plant seed) obtainable from a tobacco plant of the invention.

The invention further provides:
the use of a tobacco cell of the invention for production of a tobacco product;
the use of a tobacco plant of the invention to breed a tobacco plant;
the use of a tobacco plant of the invention for production of a tobacco product;
the use of a tobacco plant of the invention to grow a crop; and
the use of a tobacco plant of the invention to produce a tobacco leaf (e.g. a processed (preferably cured) tobacco leaf).

The invention also provides a harvested leaf of a tobacco plant of the invention or obtainable from a tobacco plant propagated from a propagation material of the invention or obtainable from a tobacco plant obtainable by a use according to the invention.

Furthermore the invention provides a processed tobacco leaf:
i) comprising a tobacco cell of the invention;
ii) obtainable from a tobacco plant obtainable from a use of the invention;

iii) obtainable by processing a tobacco plant of the invention;
iv) obtainable from a tobacco plant propagated from a tobacco plant propagation material according to the present invention; or
v) obtainable by processing a harvested leaf of a tobacco plant of the invention.

The invention further provides a tobacco product prepared from:
i) a tobacco plant according to the present invention or a part thereof;
ii) a tobacco plant or part thereof propagated from a tobacco plant propagation material according to the invention;
iii) a harvested leaf of a tobacco plant according to the invention; or
iv) a processed tobacco leaf according to the invention.

BRIEF DESCRIPTION OF THE DRAWINGS

Embodiments of the invention will now be described, by way of example only, with reference to accompanying drawings, in which:

FIG. 6 shows the nucleotide and amino acid sequences for LBD37 (SEQ ID NOs: 1 and 2), LBD38 (SEQ ID NOs: 3 and 4) and LBD39 (SEQ ID NOs: 5 and 6) from *Arabidopsis thaliana*.

FIG. 7 shows the alignment of *Arabidopsis thaliana* LBD37 (AtLBD37), LBD38 (AtLBD38) and LBD39 (AtLBD39) against orthologous proteins from different plant species (SEQ ID NOs: 11-27).

DETAILED DESCRIPTION

For the first time the present inventors have surprisingly shown that by increasing the activity or expression of a LBD nitrogen-responsive transcription factor in a tobacco plant, at least one tobacco-specific nitrosamine (TSNA) or a precursor thereto can be reduced.

Figure 1:
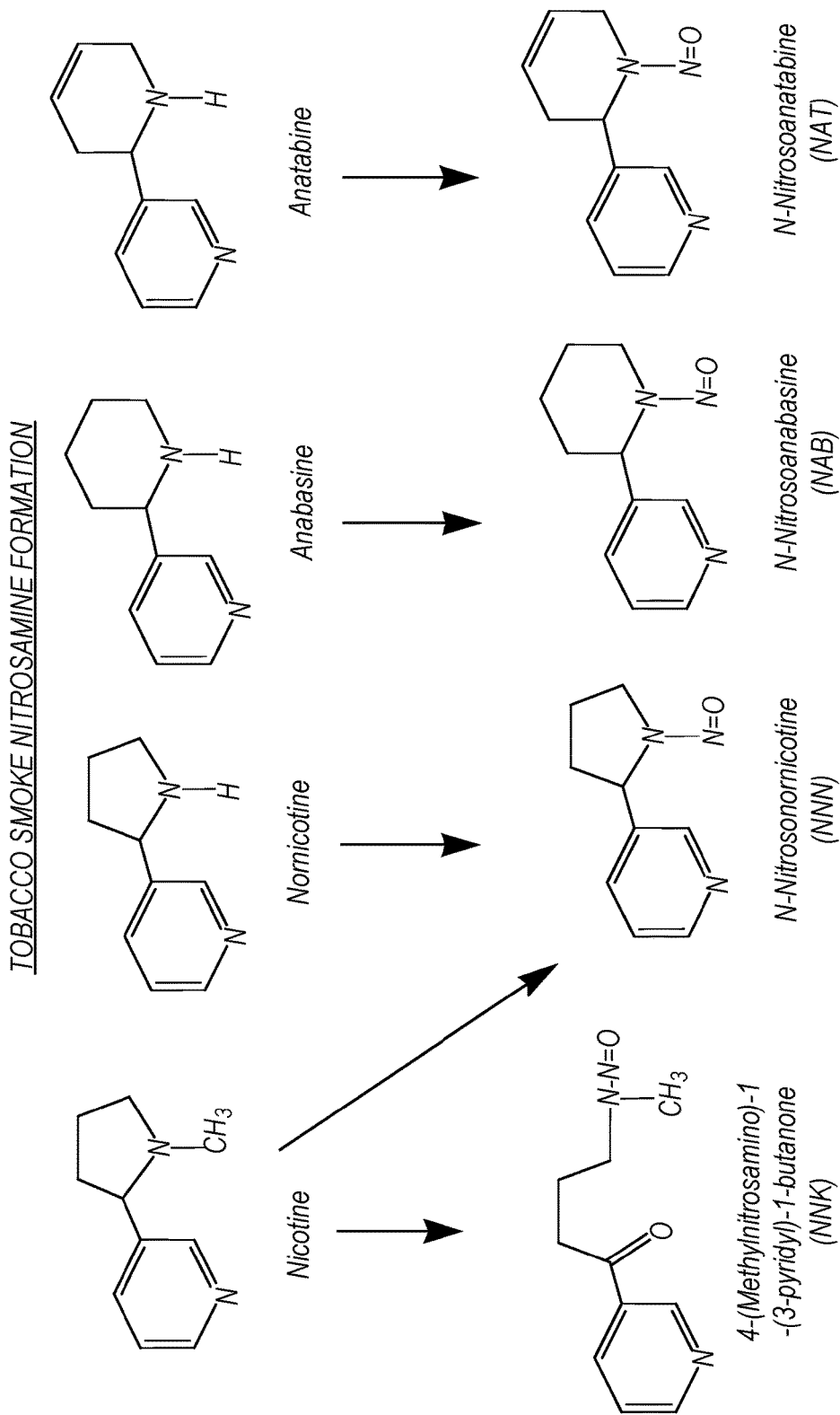
FIG. 1 shows the formation of tobacco-specific nitrosamines (TSNA) from precursors such as nicotine and nornicotine via a nitrosation reaction in tobacco smoke.

It is well known that residual nitrogen in tobacco leaves contributes to the formation of nitrosamines, through a nitrosation reaction as illustrated in FIG. 1. In particular, nitrate and nitrite and nitric oxide (NO) act as precursors to tobacco-specific nitrosamine (TSNA) formation in cured leaf. Without wishing to be bound by theory, the modification of the nitrate assimilation by modulation of LBD gene expression is believed to have the capacity to modulate the production of nitrite and nitric oxide (NO) and therefore the levels of TSNA which form during tobacco leaf curing and processing. Nevertheless, the finding of the present invention is highly unexpected.

The present invention also provides the use of a LBD nitrogen-responsive transcription factor for the reduction of at least one TSNA or a precursor thereto in a tobacco plant.

A reduction of TSNA content or concentration in a tobacco product prepared from a tobacco plant which has increased activity or expression of a LBD nitrogen-responsive transcription factor is a highly advantageous technical effect.

In one embodiment there is provided a method for producing a tobacco plant, a tobacco plant propagation material, a tobacco leaf, a processed tobacco leaf, a cut tobacco leaf or a cut and processed tobacco leaf which has a reduction in at least one TSNA or a precursor thereto, the method comprising modifying said tobacco plant to increase the activity or expression of a LBD nitrogen-responsive transcription factor.

The term "tobacco-specific nitrosamine" or "TSNA" as used herein has its usual meaning in the art, namely a nitrosamine which is found only in tobacco products or other nicotine-containing products. Suitably the at least one tobacco-specific nitrosamine may be 4-(methylnitrosamino)-1-(3-pyridyl)-1-butanone (NNK), N'-nitrosonornicotine (NNN), N'-nitrosoanatabine (NAT) or N-nitrosoanabasine (NAB).

More suitably the at least one tobacco-specific nitrosamine may be NNK or NNN.

The term "precursor thereto" when used in relation to at least one tobacco-specific nitrosamine refers to one or more chemicals or compounds of a tobacco plant that give rise to the formation of a tobacco-specific nitrosamine or are involved in the nitrosation reaction leading to tobacco-specific nitrosamine production. Suitably the term "precursor thereto" may refer to nitrate, nitrite or nitric oxide.

In one embodiment carrying out a method and or use of the invention results in a reduction of at least one TSNA or a precursor thereto in the modified tobacco plant when compared to a tobacco plant which has not been modified to increase the activity or expression of a LBD nitrogen-responsive transcription factor.

The terms "reducing at least one TSNA or precursor thereto" or "reduction of at least one TSNA or precursor thereto" are used herein to mean that the concentration and/or total content of the at least one TSNA or precursor thereto in the product, method or use of the invention is lower in relation to a comparable product, method or use. For example, a comparable tobacco product would be derived from a tobacco plant which had not been modified according to the present invention, but in which all other relevant features were the same (e.g. plant species, growing conditions, method of processing tobacco, etc).

Any method known in the art for determining the concentration and/or levels of at least one TSNA or precursor thereto may be used. In particular a method such as that detailed in Example 4 herein may be used. For example when determining the concentration and/or level of a precursor to a tobacco-specific nitrosamine a method such as one detailed in WO2009/022183, in Morot-Gaudry-Talarmain et al. 2002. Planta, 215:708-715 or in Mur et al Plant Science 181 (2011) 509-519 (which are incorporated herein by reference) may be used.

Suitably the concentration and/or total content of the at least one tobacco-specific nitrosamine or precursor thereto may be reduced by carrying out a method and/or use of the present invention. Suitably the concentration and/or level of the at least one tobacco-specific nitrosamine or precursor thereto may be reduced in a tobacco plant of the invention (e.g. obtainable or obtained by a method and/or use of the invention) when compared to the concentration and/or level of the at least one tobacco-specific nitrosamine(s) or precursor thereto in a tobacco plant which has not been modified to increase activity or expression of a LBD nitrogen-responsive transcription factor.

The concentration and/or total content of the at least one tobacco-specific nitrosamine(s) or precursor thereto may be reduced in a tobacco leaf, harvested leaf, processed tobacco leaf, tobacco product or combinations thereof obtainable or obtained from a tobacco plant of the invention when compared with a tobacco leaf, harvested leaf, processed tobacco leaf, tobacco product or combinations thereof obtainable or obtained from a tobacco plant which has not been modified to increase activity or expression of a LBD nitrogen-responsive transcription factor.

Suitably the concentration and/or total content of the at least one tobacco-specific nitrosamine or precursor thereto may be reduced in a processed tobacco leaf.

Suitably the concentration and/or level of the at least one tobacco-specific nitrosamine or precursor thereto may be reduced in a tobacco product.

In one embodiment the at least one tobacco-specific nitrosamine or precursor thereto may be reduced by at least about 1%, at least about 3%, at least about 5%, at least about 10%, at least about 20%, at least about 30%, at least about 40%, at least about 50%, at least about 60%, at least about 70%, at least about 80% or at least about 90%. In some embodiments the at least one tobacco-specific nitrosamine or precursor thereto may be reduced by between about 5% and about 95%, by between about 10% and about 90%, by between 20% and about 80%, by between 30% and about 70%, or by between about 40% and 60%.

In relation to processed (e.g. cured) tobacco leaf, the at least one tobacco-specific nitrosamine or precursor thereto may be reduced by between about 5000 ng/g and about 50 ng/g, by between about 4000 ng/g and about 100 ng/g, by between about 3000 ng/g and 500 ng/g or by between 2000 ng/g and 1000 ng/g. In some embodiments the at least one tobacco-specific nitrosamine or precursor thereto may be reduced by at least about 5000 ng/g, at least about 4000 ng/g, at least about 3000 ng/g, at least about 2000 ng/g, at least about 1000 ng/g, at least about 500 ng/g, at least about 100 ng/g or at least about 50 ng/g.

LBD Nitrogen-Responsive Transcription Factors

The LBD (lateral organ boundaries domain) genes, also known as ASYMMETRIC LEAVES2 (AS2)-like (ASL), encode a plant-specific family of transcription factors. LBD proteins are defined by a characteristic N-terminal LOB domain which is known to be responsible for DNA binding and protein-protein interactions. The LOB domain comprises a C-motif required for DNA-binding, which contains four perfectly conserved cysteine (C) residues in a $CX_2CX_6CX_3C$ (SEQ ID NO: 10) motif wherein X is a residue that is not conserved. The LOB domain also contains a conserved glycine residue and a C-terminal leucine-zipper-like sequence required for protein-protein interactions (Majer C., Hochholdinger F. Defining the boundaries: structure and function of LOB domain proteins. Trends in Plant Science (2011) 16 (1): 47-52). The founder gene LOB was shown to recognize a 6-bp GCGGCG DNA consensus motif and to activate transcription in yeast (Husbands A., Bell E. M., Shuai B., Smith H. M. S., Springer P. S. Lateral organ boundaries defines a new family of DNA-binding transcription factors and can interact with specific bHLH proteins. Nucleic Acids Research (2007) 35 (19): 6663-6671).

The *Arabidopsis* LBD gene family is composed of 43 members divided in two classes based on amino acid conservation within the LOB domain. Class I consists of LOB and LBD1 to LBD36, and class II consists of LBD37 to LBD43. In *Arabidopsis*, three LBD genes in class II, LBD37 (ASL39), LBD38 (ASL40) and LBD39 (ASL41), are known to be upregulated by nitrogen or nitrate, and act as negative regulators of anthocyanin synthesis. The LBD genes also repress many other known N-responsive genes, including key genes required for $NO_3^-$ uptake and assimilation, resulting in altered $NO_3^-$ content, nitrate reductase activity/activation and other N-related growth phenotypes (Rubin et al., 2009).

The term "lateral organ boundaries domain (LBD) nitrogen-responsive transcription factor" as used herein refers to a protein which contains a LOB domain and which acts as a transcription factor in a manner that can be affected by availability of nitrogen or nitrate.

In one embodiment, the LBD nitrogen-responsive transcription factor polypeptide sequence comprises one or more of the following motifs:

i)
(SEQ ID NO: 10)
$CX_2CX_6CX_3C$ wherein X is any amino acid ii)
(SEQ ID NO: 7)
MSCNGCRXLRKGCX iii)
(SEQ ID NO: 8)
QXXATXFXAKFXGR iv)
(SEQ ID NO: 9)
FXSLLXEAXG In a further embodiment, the LBD nitrogen-responsive transcription factor is LBD37, LBD38 or LBD39.

The term "increasing the activity of a LBD nitrogen-responsive transcription factor" means that the activity of a LBD nitrogen-responsive transcription factor in the plant as a whole is increased in the modified plant when compared to a plant that has not been modified to increase the activity or expression of a LBD nitrogen-responsive transcription factor.

In one embodiment the increase in activity of the LBD nitrogen-responsive transcription factor in the modified plant may be more than about 5% when compared to an unmodified plant. Suitably the increase in LBD nitrogen-responsive transcription factor activity may be more than about 10%, suitably more than about 15%. In some embodiments the increase in LBD nitrogen-responsive transcription factor activity may be more than about 20%, more suitably more than about 30%. In some embodiments increase in LBD nitrogen-responsive transcription factor activity may be more than about 40%, such as about 50%, about 60%, about 70%, about 80%, about 90% or about 100%.

In some embodiments the modification of the plant to increase activity of the LBD nitrogen-responsive transcription factor may be carried out using gene-editing.

Gene-editing may be carried out using any method known in the art. A few non-limiting examples are presented here including use of the CRISPR-Cas9 system. CRISPR/Cas9 genomic editing tools are available commercially such as "Guide-it" from Clontech (Avenue du President Kennedy 78100 Saint-Germain-en-Laye, France). Another method of gene-editing includes the use of TALEN (transcription activator-like effector nuclease) technology with kits available commercially (e.g. from Addgene, 1 Kendall Sq. Ste. B7102, Cambridge, Mass. 02139, USA). A further method comprises the use of Zinc Finger Nucleases such as the CompoZr® Zinc Finger Nuclease Technology available from Sigma-Aldrich. Another method comprises the use of meganucleases (or a further method) described in Silva et al Curr Gene Ther. February 2011; 11(1): 11-27 (the teaching of which is incorporated herein by reference). A yet further method is oligonucleotide-directed mutagenesis (ODM) such as KeyBase® available from Keygene (Agro Business Park 90, 6708 PW Wageningen, The Netherlands).

In one embodiment the LBD nitrogen-responsive transcription factor for use in accordance with the present invention may be endogenous to the tobacco plant.

Reference herein to an "endogenous" gene not only refers to the gene in question as found in a plant in its natural form (i.e., without there being any human intervention), but also refers to that same gene (or a substantially homologous nucleic acid/gene) in an isolated form subsequently (re) introduced into a plant (a transgene). For example, a transgenic plant containing such a transgene may encounter a substantial reduction of the transgene expression and/or substantial reduction of expression of the endogenous gene. The isolated gene may be isolated from an organism or may be manmade, for example by chemical synthesis.

In another embodiment the LBD nitrogen-responsive transcription factor for use in accordance with the present invention may be exogenous to the tobacco plant.

In one embodiment the LBD nitrogen-responsive transcription factor may be obtainable from a plant selected from one or more of the following genera: *Arabidopsis, Brassica, Oryza, Phaseolus, Solanum, Spinacia*.

Suitably the *Arabidopsis* LBD nitrogen-responsive transcription factor may be an *Arabidopsis thaliana* LBD nitrogen-responsive transcription factor.

In one embodiment the LBD nitrogen-responsive transcription factor for use in accordance with the invention may be selected from *Brassica napus*.

In one embodiment the LBD nitrogen-responsive transcription factor for use in accordance with the invention may be selected from *Brassica rapa*.

In one embodiment the LBD nitrogen-responsive transcription factor for use in accordance with the invention may be selected from *Capsicum annuum*.

In one embodiment the LBD nitrogen-responsive transcription factor for use in accordance with the invention may be selected from *Lactuca sativa*.

In one embodiment the LBD nitrogen-responsive transcription factor for use in accordance with the invention may be selected from *Oryza sativa*, suitably *Oryza sativa* subsp. *japonica*.

In one embodiment the LBD nitrogen-responsive transcription factor for use in accordance with the invention may be selected from *Phaseolus vulgaris*.

In one embodiment the LBD nitrogen-responsive transcription factor for use in accordance with the invention may be selected from *Solanum lycopersicum*.

In one embodiment the LBD nitrogen-responsive transcription factor for use in accordance with the invention may be selected from *Solanum tuberosum*.

In one embodiment the LBD nitrogen-responsive transcription factor for use in accordance with the invention may be selected from *Spinacia oleracea*.

In one embodiment, the LBD nitrogen-responsive transcription factor for use in the present invention may be from the family Solanaceae, more preferably of the subfamily Cestoideae, more preferably of the genus *Nicotiana*, and most preferably from *Nicotiana tabacum* or *N. rustica*.

In one embodiment, the LBD nitrogen-responsive transcription factor for use in accordance with the present invention is from the genus *Nicotiana*.

The LBD nitrogen-responsive transcription factor may be from any species of the genus *Nicotiana*, including *N. rustica* and *N. tabacum* (for example, LA B21, LN KY171, TI 1406, Basma, Galpao, Perique, Beinhart 1000-1, and Petico). Other species include *N. acaulis, N. acuminata, N. acuminata* var. *multiflora, N. africana, N. alata, N. amplexicaulis, N. arentsii, N. attenuata, N. benavidesii, N. benthamiana, N. bigelovii, N. bonariensis, N. cavicola, N. clevelandii, N. cordifolia, N. corymbosa, N. debneyi, N. excelsior, N. forgetiana, N. fragrans, N. glauca, N. glutinosa, N. goodspeedii, N. gossei, N. hybrid, N. ingulba, N. kawakamii, N. knightiana, N. langsdorffii, N. linearis, N. longiflora, N. maritima, N. megalosiphon, N. miersii, N. noctiflora, N. nudicaulis, N. obtusifolia, N. occidentalis, N. occidentalis* subsp. *hesperis, N. otophora, N. paniculata, N. pauciflora, N. petunioides, N. plumbaginifolia, N. quadrivalvis, N. raimondii, N. repanda, N. rosulata, N. rosulata* subsp. *ingulba, N. rotundifolia, N. setchellii, N. simulans, N. solanifolia, N. spegazzinii, N. stocktonii, N. suaveolens, N. sylvestris, N. thyrsiflora, N. tomentosa, N. tomentosiformis, N. trigonophylla, N. umbratica, N. undulata, N. velutina, N. wigandioides*, and *N. x sanderae*.

Figure 7:
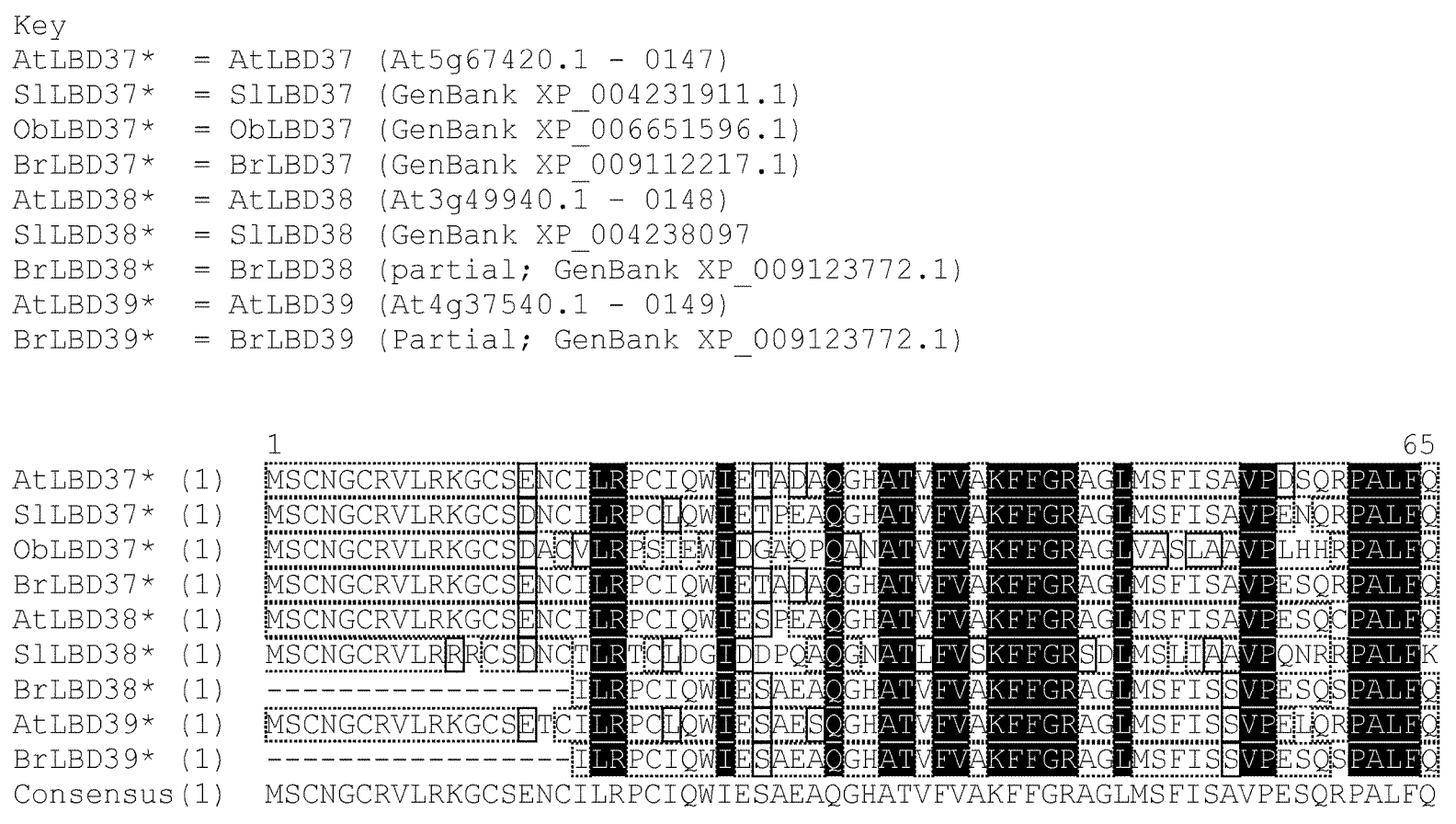

In one embodiment the LBD nitrogen-responsive transcription factor is from class II of the LBD gene family. Suitably the LBD nitrogen-responsive transcription factor is LBD37, LBD38 or LBD39. In one particular embodiment, the LBD37, LBD38 or LBD39 is derived from *Arabidopsis thaliana*. In another embodiment, the LBD37, LBD38 or LBD39 is from another species, suitably one of the proteins listed in FIG. 7 (i.e. SlLBD37, ObLBD37, BrLBD37, SlLBD38, BrLBD38 or BrLBD39).

In another embodiment, the LBD nitrogen-responsive transcription factor polypeptide sequence comprises one or more of the following motifs:

i)
(SEQ ID NO: 10)
$CX_2CX_6CX_3C$ wherein X is any amino acid ii)
(SEQ ID NO: 7)
MSCNGCRXLRKGCX iii)
(SEQ ID NO: 8)
QXXATXFXAKFXGR iv)
(SEQ ID NO: 9)
FXSLLXEAXG In a further embodiment the LBD nitrogen-responsive transcription factor for use in accordance with the present invention may be encoded by a polynucleotide sequence comprising:
i) a polynucleotide sequence shown herein as SEQ ID NO: 1, SEQ ID NO: 3 or SEQ ID NO: 5;

ii) a functional fragment of the polynucleotide sequence shown in i) which functional fragment encodes a functional LBD nitrogen-responsive transcription factor, or iii) a polynucleotide which encodes a polypeptide comprising the amino acid sequence shown herein as SEQ ID NO: 2, SEQ ID NO: 4 or SEQ ID NO: 6; or iv) a polynucleotide sequence which can hybridize to the polynucleotide taught in i), ii) or iii) above under high stringency conditions, or v) a polynucleotide sequence which has at least 70% (preferably 85%, more preferably 90%) identity with the polynucleotide shown in i), ii) or iii) above, or vi) a polynucleotide sequence which differs from a polynucleotide shown in i), ii) or iii) due to degeneracy of the genetic code.

The term "functional fragment" as used herein refers to a portion of a polynucleotide that is capable of encoding a LBD nitrogen-responsive transcription factor that retains its activity. In one embodiment the functional fragment may be a portion of a polynucleotide of the invention comprising at least 50 nucleotides, at least 75 nucleotides, at least 100 nucleotides, at least 150 nucleotides, at least 200 nucleotides, at least 300 nucleotides, at least 400 nucleotides or at least 500 nucleotides of a polynucleotide of the invention.

The term "degeneracy of the genetic code" as used herein refers to the redundancy in codons encoding polypeptide sequences exhibited as the multiplicity of three-codon combinations specifying an amino acid. For example in an mRNA molecule encoding a polypeptide having an isoleucine amino acid, isoleucine can be encoded by AUU, AUC or AUA. This means that a DNA molecule encoding the RNA can have multiple sequences yet the resulting polypeptide will have the same sequence. In other words polymorphic nucleotide sequences can encode the same polypeptide product. This means that one nucleic acid sequence can comprise a sequence with very low sequence identity to a second sequence while encoding the same polypeptide sequence.

In one embodiment the polynucleotide sequence may have at least 80% identity with SEQ ID No. 1, SEQ ID No. 3 or SEQ ID No. 5.

Suitably the polynucleotide sequence may have at least 90% identity with SEQ ID No. 1, SEQ ID No. 3 or SEQ ID No. 5.

Suitably the polynucleotide sequence may have at least 95% identity (more suitably at least 99% identity) with SEQ ID No. 1, SEQ ID No. 3 or SEQ ID No. 5.

More suitably the polynucleotide sequence may have at least 99% identity with SEQ ID No. 1, SEQ ID No. 3 or SEQ ID No. 5.

In another embodiment the LBD nitrogen-responsive transcription factor for use in accordance with the present invention may comprise a polypeptide sequence shown herein as SEQ ID No. 2, SEQ ID No. 4 or SEQ ID No. 6 or a polypeptide sequence which comprises SEQ ID No. 2, SEQ ID No. 4 or SEQ ID No. 6 with a conservative substitution of at least one of the amino acids, or a polypeptide having at least 70% identity with SEQ ID No. 2, SEQ ID No. 4 or SEQ ID No. 6.

Suitably the polypeptide may have at least 80% identity with SEQ ID No. 2, SEQ ID No. 4 or SEQ ID No. 6.

More suitable the polypeptide may have at least 90% identity with SEQ ID No. 2, SEQ ID No. 4 or SEQ ID No. 6. Preferably the polypeptide may have at least 95% identity with SEQ ID No. 2, SEQ ID No. 4 or SEQ ID No. 6.

More preferably the polypeptide may have at least 99% identity with SEQ ID No. 2, SEQ ID No. 4 or SEQ ID No. 6.

Increasing Expression

The method and uses of the present invention comprise an increase in expression of at least one LBD nitrogen-responsive transcription factor. The increase in expression can be achieved by any means known to the person skilled in the art.

The term "increased expression" or "overexpression" as used herein means any form of expression that is additional to the original wild-type expression level.

"Increased expression" means that a plant is increased in the mRNA level or the protein level in comparison with an expression level of a parent plant of the same breed. The expression level is compared to a corresponding part in the parent plant of the same breed cultured under the same condition. A case where the expression level increases at least 1.1 times greater than that of the parent plant is preferably considered as a case where the expression level is increased. Here, it is more preferable that the expression level of the plant has a significant difference of 5% by a t-test compared with that of the parent plant, in order to be considered that there is an increase in the expression level. It is preferable that the expression levels of the plant and the parent plant be measured at the same time by the same method. However, data stored as background data may be also used.

Methods for increasing expression of genes or gene products are well documented in the art and include, for example, overexpression driven by appropriate promoters, the use of transcription enhancers or translation enhancers. Isolated nucleic acids which serve as promoter or enhancer elements may be introduced in an appropriate position (typically upstream) of a non-heterologous form of a polynucleotide so as to upregulate expression of a nucleic acid encoding the polypeptide of interest. For example, endogenous promoters may be altered in vivo by mutation, deletion, and/or substitution (see, U.S. Pat. No. 5,565,350; WO9322443), or isolated promoters may be introduced into a plant cell in the proper orientation and distance from a gene of the present invention so as to control the expression of the gene.

If polypeptide expression is desired, it is generally desirable to include a polyadenylation region at the 3'-end of a polynucleotide coding region. The polyadenylation region can be derived from the natural gene, from a variety of other plant genes, or from T-DNA. The 3$^1$ end sequence to be added may be derived from, for example, the nopaline synthase or octopine synthase genes, or alternatively from another plant gene, or less preferably from any other eukaryotic gene.

An intron sequence may also be added to the 5' untranslated region (UTR) or the coding sequence of the partial coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold (Buchman and Berg (1988) Mol. Cell biol. 8: 4395-4405; Callis et al. (1987) Genes Dev 1:1183-1200). Such intron enhancement of gene expression is typically greatest when placed near the 5' end of the transcription unit. Use of the maize introns Adh1-S intron 1, 2, and 6, the Bronze-1 intron are known in the art. For general information see: The Maize Handbook, Chapter 116, Freeling and Walbot, Eds., Springer, N.Y. (1994).

In one embodiment the increased expression may be achieved by the use of gene-editing or targeted mutagenesis.

Gene-editing may be carried out using any method known in the art. A few non-limiting examples are presented here including use of the CRISPR-Cas9 system. CRISPR/Cas9 genomic editing tools are available commercially such as "Guide-it" from Clontech (Avenue du President Kennedy 78100 Saint-Germain-en-Laye, France). Another method of gene-editing includes the use of TALEN (transcription activator-like effector nuclease) technology with kits available commercially (e.g. from Addgene, 1 Kendall Sq. Ste. B7102, Cambridge, Mass. 02139, USA). A further method comprises the use of Zinc Finger Nucleases such as the CompoZr® Zinc Finger Nuclease Technology available from Sigma-Aldrich. Another method comprises the use of meganucleases (or a further method) described in Silva et al Curr Gene Ther. February 2011; 11(1): 11-27 (the teaching of which is incorporated herein by reference). A yet further method is oligonucleotide-directed mutagenesis (ODM) such as KeyBase® available from Keygene (Agro Business Park 90, 6708 PW Wageningen, The Netherlands).

Suitably, gene-editing may be used to alter the sequence of a LBD nitrogen-responsive transcription factor promoter in vivo.

In another embodiment of the invention, increased expression of a LBD nitrogen-responsive transcription factor may be achieved by expressing within the plant a polynucleotide (e.g. an exogenous polynucleotide) comprising a nucleic acid sequence encoding a LBD nitrogen-responsive transcription factor. In one embodiment, said polynucleotide (e.g. exogenous polynucleotide) comprises a nucleic acid sequence encoding a LBD nitrogen-responsive transcription factor operably linked with a heterologous promoter for directing transcription of said nucleic acid sequence in said plant.

In some embodiments the promoter may be selected from the group consisting of: a constitutive promoter, a senescence-specific promoter, a tissue-specific promoter, a developmentally-regulated promoter and an inducible promoter.

In one embodiment the promoter may be a constitutive promoter.

A constitutive promoter directs the expression of a gene throughout the various parts of a plant continuously during plant development, although the gene may not be expressed at the same level in all cell types. Examples of known constitutive promoters include those associated with the cauliflower mosaic virus 35S transcript (Odell J T, Nagy F, Chua N H. (1985). Identification of DNA sequences required for activity of the cauliflower mosaic virus 35S promoter. Nature. 313 810-2), the rice actin 1 gene (Zhang W, McElroy D, Wu R. (1991). Analysis of rice Act1 5' region activity in transgenic rice plants. Plant Cell 3 1155-65) and the maize ubiquitin 1 gene (Cornejo M J, Luth D, Blankenship K M, Anderson O D, Blechl A E. (1993). Activity of a maize ubiquitin promoter in transgenic rice. Plant Molec. Biol. 23 567-81). Constitutive promoters such as the Carnation Etched Ring Virus (CERV) promoter (Hull R, Sadler J, Longstaff M (1986) The sequence of carnation etched ring virus DNA: comparison with cauliflower mosaic virus and retroviruses. *EMBO Journal,* 5(2):3083-3090).

The constitutive promoter may be selected from a: a carnation etched ring virus (CERV) promoter, a cauliflower mosaic virus (CaMV 35S promoter), a promoter from the rice actin 1 gene or the maize ubiquitin 1 gene.

Suitably the promoter may be a CERV promoter.

In one embodiment the promoter may be a senescence-specific promoter.

A "senescence-specific promoter" (SAG) can be a promoter which is associated with controlling the expression of a senescence-associated gene. Hence, the promoter can restrict expression of a coding sequence (i.e. a gene) to which it is operably linked substantially exclusively in senescing tissue. Therefore, a senescence-specific promoter can be a promoter capable of preferentially promoting gene expression in a plant tissue in a developmentally-regulated manner such that expression of a 3' protein-coding region occurs substantially only when the plant tissue is undergoing senescence. It will be appreciated that senescence tends to occur in the older parts of the plant, such as the older leaves, and not in the younger parts of the plants, such as the seeds.

One example of a plant which is known to express numerous senescence-associated genes is *Arabidopsis*. Hence, a senescence-specific promoter may be isolated from a senescence-associated gene in *Arabidopsis*. Gepstein et al. (The Plant Journal, 2003, 36, 629-642) conducted a detailed study of SAGs and their promoters using *Arabidopsis* as a model. The genetic construct may comprise a promoter from any of the SAGs disclosed in this paper. For example, a suitable promoter may be selected from a group consisting of SAG12, SAG13, SAG101, SAG21 and SAG18, or a functional variant or a functional fragment thereof.

In one embodiment the promoter may be a SAG12 promoter, which will be known to the skilled technician, or a functional variant or a fragment thereof (Gan & Amasino, 1997, Plant Physiology, 113: 313-319).

Suitable promoters and sequences thereof may be found in WO2010/097623 which is incorporated herein by reference.

In another embodiment the promoter may be a tissue-specific promoter.

A tissue-specific promoter is one which directs the expression of a gene in one (or a few) parts of a plant, usually throughout the lifetime of those plant parts. The category of tissue-specific promoter commonly also includes promoters whose specificity is not absolute, i.e. they may also direct expression at a lower level in tissues other than the preferred tissue.

A number of tissue-specific promoters are known in the art and include those associated with the patatin gene expressed in potato tuber and the high molecular weight glutenin gene expressed in wheat, barley or maize endosperm. Any of these promoters may be used in the present invention.

Suitably the tissue-specific promoter may be a leaf-specific promoter. Suitable leaf-specific promoters may include ASYMMETRIC LEAVES 1 (AS1).

In another embodiment the promoter may be a developmentally-regulated promoter.

A developmentally-regulated promoter directs a change in the expression of a gene in one or more parts of a plant at a specific time during plant development. The gene may be expressed in that plant part at other times at a different (usually lower) level, and may also be expressed in other plant parts.

In one embodiment the promoter may be an inducible promoter.

An inducible promoter is capable of directing the expression of a gene in response to an inducer. In the absence of the inducer the gene will not be expressed. The inducer may act directly upon the promoter sequence, or may act by counteracting the effect of a repressor molecule. The inducer may be a chemical agent such as a metabolite, a protein, a growth regulator, or a toxic element, a physiological stress such as heat, wounding, or osmotic pressure, or an indirect consequence of the action of a pathogen or pest. A developmentally-regulated promoter might be described as a specific type of inducible promoter responding to an endogenous inducer produced by the plant or to an environmental stimulus at a particular point in the life cycle of the plant. Examples of known inducible promoters include those associated with wound response, such as described by Warner S A, Scott R, Draper J. (1993) (Isolation of an asparagus intracellular PR gene (AoPR1) wound-responsive promoter by the inverse polymerase chain reaction and its characterization in transgenic tobacco. Plant J. 3 191-201), temperature response as disclosed by Benfey & Chua (1989) (Benfey, P. N., and Chua, N-H. (1989) Regulated genes in transgenic plants. Science 244 174-181), and chemically induced, as described by Gatz (1995) (Gatz, C. (1995) Novel inducible/repressible gene expression systems. Methods in Cell Biol. 50 411-424).

Thus in one embodiment the promoter may be selected from the group consisting of: the CERV promoter, the cauliflower mosaic virus 35S promoter (full or truncated), the rubisco promoter, the pea plastocyanin promoter, the nopaline synthase promoter, the chlorophyll r/b binding promoter, the high molecular weight glutenin promoter, the α,β-gliadin promoter, the hordein promoter and the patatin promoter.

The invention further provides a construct or vector comprising a nucleic acid encoding a LBD nitrogen-responsive transcription factor operably linked with a leaf-specific promoter.

The invention also provides a construct or vector comprising a nucleic acid encoding a LBD nitrogen-responsive transcription factor operably linked with a senescence-specific promoter.

The construct may be comprised in a vector. Suitably the vector may be a plasmid.

Tobacco Plants

The present invention provides methods, uses directed to tobacco plants as well as a tobacco cell, a tobacco plant and a plant propagation material.

The term "tobacco plant" as used herein refers to a plant in the genus *Nicotiana* that is used in the production of tobacco products. Non-limiting examples of suitable tobacco plants include *N. tabacum* and *N. rustica* (for example, LA B21, LN KY171, TI 1406, Basma, Galpao, Perique, Beinhart 1000-1, and Petico). It is not intended that the term "tobacco" extends to *Nicotiana* species that are not useful for the production of tobacco products.

Thus, in one embodiment a tobacco plant does include *Nicotiana plumbaginifolia*.

The tobacco material can be derived from varieties of *Nicotiana tabacum* species, commonly known as Burley varieties, flue or bright varieties, dark varieties and oriental/Turkish varieties. In some embodiments, the tobacco material is derived from a Burley, Va., flue-cured, air-cured, fire-cured, Oriental, or a dark tobacco plant. The tobacco plant may be selected from Maryland tobacco, rare tobacco, speciality tobacco, expanded tobacco or the like.

The use of tobacco cultivars and elite tobacco cultivars is also contemplated herein. The tobacco plant for use herein may therefore be a tobacco variety or elite tobacco cultivar.

Particularly useful *Nicotiana tabacum* varieties include Burley type, dark type, flue-cured type, and Oriental type tobaccos.

In some embodiments, the tobacco plant may be, for example, selected from one or more of the following varieties: *N. tabacum* AA 37-1, *N. tabacum* B 13P, *N. tabacum* Xanthi (Mitchell-Mor), *N. tabacum* KT D#3 Hybrid 107, *N. tabacum* Bel-W3, *N. tabacum* 79-615, *N. tabacum* Samsun Holmes N N, F4 from cross *N. tabacum* BU21×*N. tabacum* Hoja Parado, line 97, *N. tabacum* KTRDC#2 Hybrid 49, *N. tabacum* KTRDC#4 Hybrid 1 10, *N. tabacum* Burley 21, *N. tabacum* PM016, *N. tabacum* KTRDC#5 KY 160 SI, *N. tabacum* KTRDC#7 FCA, *N. tabacum* KTRDC#6 TN 86 SI, *N. tabacum* PM021, *N. tabacum* K 149, *N. tabacum* K 326, *N. tabacum* K 346, *N. tabacum* K 358, *N. tabacum* K 394, *N. tabacum* K 399, *N. tabacum* K 730, *N. tabacum* KY 10, *N. tabacum* KY 14, *N. tabacum* KY 160, *N. tabacum* KY 17, *N. tabacum* KY 8959, *N. tabacum* KY 9, *N. tabacum* KY 907, *N. tabacum* MD 609, *N. tabacum* McNair 373, *N. tabacum* NC 2000, *N. tabacum* PG 01, *N. tabacum* PG 04, *N. tabacum* P01, *N. tabacum* P02, *N. tabacum* P03, *N. tabacum* RG 11, *N. tabacum* RG 17, *N. tabacum* RG 8, *N. tabacum* Speight G-28, *N. tabacum* TN 86, *N. tabacum* TN 90, *N. tabacum* VA 509, *N. tabacum* AS44, *N. tabacum* Banket A1, *N. tabacum* Basma Drama B84/31, *N. tabacum* Basma I Zichna ZP4/B, *N. tabacum* Basma Xanthi BX 2A, *N. tabacum* Batek, *N. tabacum* Besuki Jember, *N. tabacum* C104, *N. tabacum* Coker 319, *N. tabacum* Coker 347, *N. tabacum* Criollo Misionero, *N. tabacum* PM092, *N. tabacum* Delcrest, *N. tabacum* Djebel 81, *N. tabacum* DVH 405, *N. tabacum* Galpao Comum, *N. tabacum* HB04P, *N. tabacum* Hicks Broadleaf, *N. tabacum* Kabakulak Elassona, *N. tabacum* PM102, *N. tabacum* Kutsage E1, *N. tabacum* KY 14xL8, *N. tabacum* KY 171, *N. tabacum* LA BU 21, *N. tabacum* McNair 944, *N. tabacum* NC 2326, *N. tabacum* NC 71, *N. tabacum* NC 297, *N. tabacum* NC 3, *N. tabacum* PVH 03, *N. tabacum* PVH 09, *N. tabacum* PVH 19, *N. tabacum* PVH 21 10, *N. tabacum* Red Russian, *N. tabacum* Samsun, *N. tabacum* Saplak, *N. tabacum* Simmaba, *N. tabacum* Talgar 28, *N. tabacum* PM132, *N. tabacum* Wislica, *N. tabacum* Yayaldag, *N. tabacum* NC 4, *N. tabacum* TR Madole, *N. tabacum* Prilep HC-72, *N. tabacum* Prilep P23, *N. tabacum* Prilep PB 156/1, *N. tabacum* Prilep P12-2/1, *N. tabacum* Yaka JK-48, *N. tabacum* Yaka JB 125/3, *N. tabacum* T1-1068, *N. tabacum* KDH-960, *N. tabacum* TI-1070, *N. tabacum* TW136, *N. tabacum* PM204, *N. tabacum* PM205, *N. tabacum* Basma, *N. tabacum* TKF 4028, *N. tabacum* L8, *N. tabacum* TKF 2002, *N. tabacum* TN90, *N. tabacum* GR141, *N. tabacum* Basma xanthi, *N. tabacum* GR149, *N. tabacum* GR153, and *N. tabacum* Petit Havana.

Non-limiting examples of varieties or cultivars are: BD 64, CC 101, CC 200, CC 27, CC 301, CC 400, CC 500, CC 600, CC 700, CC 800, CC 900, Coker 176, Coker 319, Coker 371 Gold, Coker 48, CD 263, DF911, DT 538 LC Galpao tobacco, GL 26H, GL 350, GL 600, GL 737, GL 939, GL 973, HB 04P, HB 04P LC, HB3307PLC, Hybrid 403LC, Hybrid 404LC, Hybrid 501 LC, K 149, K 326, K 346, K 358, K394, K 399, K 730, KDH 959, KT 200, KT204LC, KY10, KY14, KY 160, KY 17, KY 171, KY 907, KY907LC, KTY14xL8 LC, Little Crittenden, McNair 373, McNair 944, msKY 14xL8, Narrow Leaf Madole, Narrow Leaf Madole LC, NBH 98, N-126, N-777LC, N-7371 LC, NC 100, NC 102, NC 2000, NC 291, NC 297, NC 299, NC 3, NC 4, NC 5, NC 6, NC7, NC 606, NC 71, NC 72, NC 810, NC BH 129, NC 2002, Neal Smith Madole, OXFORD 207, PD 7302 LC, PD 7309 LC, PD 7312 LC 'Periq'e' tobacco, PVH03, PVH09, PVH19, PVH50, PVH51, R 610, R 630, R 7-11, R 7-12, RG 17, RG 81, RG H51, RGH 4, RGH 51, RS 1410, Speight 168, Speight 172, Speight 179, Speight 210, Speight 220, Speight 225, Speight 227, Speight 234, Speight G-28, Speight G-70, Speight H-6, Speight H20, Speight NF3, TI 1406, TI 1269, TN 86, TN86LC, TN 90, TN 97, TN97LC, TN D94, TN D950, TR (Tom Rosson) Madole, Va. 309, VA359, AA 37-1, B 13P, Xanthi (Mitchell-Mor), Bel-W3, 79-615, Samsun Holmes NN, KTRDC number 2 Hybrid 49, Burley 21, KY 8959, KY 9, MD 609, PG 01, PG 04, P01, P02, P03, RG 11, RG 8, VA 509, AS44, Banket A1, Basma Drama B84/31, Basma I Zichna ZP4/B, Basma Xanthi BX 2A, Batek, Besuki Jember, C104, Coker 347, Criollo Misionero, Delcrest, Djebel 81, DVH 405, Galpao Comum, HB04P, Hicks Broadleaf, Kabakulak Elassona, Kutsage E1, LA BU 21, NC 2326, NC 297, PVH 21 10, Red Russian, Samsun, Saplak, Simmaba, Talgar 28, Wislica, Yayaldag, Prilep HC-72, Prilep P23, Prilep PB 156/1, Prilep P12-2/1, Yaka JK-48, Yaka JB 125/3, TI-1068, KDH-960, TI-1070, TW136, Basma, TKF 4028, L8, TKF 2002, GR141, Basma xanthi, GR149, GR153, Petit Havana. Low converter subvarieties of the above, even if not specifically identified herein, are also contemplated.

In one embodiment the tobacco plant is a Burley type tobacco plant, suitably a Burley PH2517.

In one embodiment the plant propagation material may be obtainable from a tobacco plant of the invention.

A "plant propagation material" as used herein refers to any plant matter taken from a plant from which further plants may be produced.

Suitably the plant propagation material may be a seed.

In one embodiment the tobacco cell, tobacco plant and/or plant propagation material of the invention may comprise an exogenous LBD nitrogen-responsive transcription factor. In another embodiment the tobacco cell, tobacco plant and/or plant propagation material may comprise a construct or vector according to the invention. In another embodiment the tobacco cell, tobacco plant and/or plant propagation material may be obtainable (e.g. obtained) by a method according to the invention.

Suitably a tobacco plant according to the present invention may comprise a reduced amount of at least one tobacco-specific nitrosamine(s) when compared to an unmodified tobacco plant, wherein the modification is an increase in activity or expression of a LBD nitrogen-responsive transcription factor in said modified plant.

In one embodiment the tobacco plant in accordance with the present invention comprises a tobacco cell of the invention.

In another embodiment the plant propagation material may be obtainable (e.g. obtained) from a tobacco plant of the invention.

In another embodiment the tobacco cell, tobacco plant and/or plant propagation material may comprise:
i) a polynucleotide sequence shown herein as SEQ ID No. 1, SEQ ID No. 3 or SEQ ID No. 5, or
ii) a fragment of the polynucleotide sequence shown in i) which functional fragment encodes a nitrate reductase decoupled from regulation by one or more post-translational regulatory mechanism(s) to which a nitrate reductase in tobacco is typically subjected, or
iii) a polynucleotide which encodes a polypeptide comprising the amino acid sequence shown herein as SEQ ID No. 2, SEQ ID No. 4 or SEQ ID No. 6, or
iv) a polynucleotide sequence which can hybridize to the polynucleotide taught in i), ii) or iii) above under high stringency conditions, or
v) a polynucleotide sequence which has at least 70% (preferably 85%, more preferably 90%) identity with the polynucleotide shown in i), ii) or iii) above, or
vi) a polynucleotide sequence which differs from polynucleotide shown in i), ii) or iii) due to degeneracy of the genetic code.

In one embodiment the polynucleotide sequence may have at least 80% identity with SEQ ID No. 1, SEQ ID No. 3 or SEQ ID No. 5.

Suitably the polynucleotide sequence may have at least 90% identity with SEQ ID No. 1, SEQ ID No. 3 or SEQ ID No. 5.

Suitably the polynucleotide sequence may have at least 95% identity (more suitably at least 99% identity) with SEQ ID No. 1, SEQ ID No. 3 or SEQ ID No. 5.

In another embodiment the tobacco cell, tobacco plant and/or plant propagation material may comprise a LBD nitrogen-responsive transcription factor comprising a polypeptide sequence shown herein as SEQ ID No. 2, SEQ ID No. 4 or SEQ ID No. 6 or a polypeptide sequence which comprises SEQ ID No. 2, SEQ ID No. 4 or SEQ ID No. 6 with a conservative substitution of at least one of the amino acids, or a polypeptide having at least 70% identity with SEQ ID No. 2, SEQ ID No. 4 or SEQ ID No. 6.

Suitably the polypeptide may have at least 80% identity with SEQ ID No. 2, SEQ ID No. 4 or SEQ ID No. 6. More suitably the polypeptide may have at least 90% identity with SEQ ID No. 2, SEQ ID No. 4 or SEQ ID No. 6. In particular the polypeptide may have at least 95% identity with SEQ ID No. 2, SEQ ID No. 4 or SEQ ID No. 6.

Most suitably the polypeptide may have at least 99% identity with SEQ ID No. 2, SEQ ID No. 4 or SEQ ID No. 6.

In one embodiment there is provided the use of a tobacco cell as provided for in the foregoing embodiments for production of a tobacco product.

Additionally there is provided the use of a tobacco plant as described herein to breed a tobacco plant.

The present invention also provides in another embodiment the use of a tobacco plant of the foregoing embodiments for the production of a tobacco product.

In another embodiment there is provided the use of a tobacco plant of the invention to grow a crop.

Amino Acids

In one embodiment the modification of a plant to increase the activity or expression of a LBD nitrogen-responsive transcription factor according to the present invention may result in an alteration in the concentration of amino acids in a plant when compared to an unmodified plant.

In one embodiment the modification of a plant to increase the activity or expression of a LBD nitrogen-responsive transcription factor may result in an alteration in the concentration of one or more amino acid(s) selected from the group consisting of: histidine, aspartate, asparagine, glutamate, glutamine, threonine and proline.

Suitably the modification of a plant to increase the activity or expression of a LBD nitrogen-responsive transcription factor may result in a reduction in the concentration of one or more amino acid(s) selected from the group consisting of: histidine, asparagine, glutamine and threonine.

Suitably the modification of a plant to increase the activity or expression of a LBD nitrogen-responsive transcription factor may result in an increase in the concentration of one or more amino acid(s) selected from the group consisting of: aspartate, glutamate and proline.

Products

The present invention also provides for products obtainable or obtained from tobacco according to the present invention.

In one embodiment there is provided the use of a tobacco plant of the invention to produce a tobacco leaf.

Suitably the tobacco leaf may be subjected to downstream applications such as processing. Thus in one embodiment the use of the foregoing embodiment may provide a processed tobacco leaf. Suitably the tobacco leaf may be subjected to curing, fermenting, pasteurising or combinations thereof.

In another embodiment the tobacco leaf may be cut. In some embodiments the tobacco leaf may be cut before or after being subjected to curing, fermenting, pasteurising or combinations thereof.

In one embodiment the present invention provides a harvested leaf of a tobacco plant of the invention.

In a further embodiment the harvested leaf may be obtainable (e.g. obtained) from a tobacco plant propagated from a propagation material of the present invention.

In another embodiment there is provided a harvest leaf obtainable from a method or use of the present invention.

Suitably the harvested leaf may be a cut harvested leaf.

In some embodiments the harvested leaf may comprise viable tobacco cells. In other embodiments the harvested leaf may be subjected to further processing.

There is also provided a processed tobacco leaf.

The processed tobacco leaf may be obtainable from a tobacco plant of the invention.

Suitably the processed tobacco leaf may be obtainable from a tobacco plant obtained in accordance with any of the methods and/or uses of the present invention.

In another embodiment the processed tobacco leaf may be obtainable from a tobacco plant propagated form a tobacco plant propagation material according to the present invention.

The processed tobacco leaf of the present invention may be obtainable by processing a harvested leaf of the invention.

The term "processed tobacco leaf" as used herein refers to a tobacco leaf that has undergone one or more processing steps to which tobacco is subjected to in the art. A "processed tobacco leaf" comprises no or substantially no viable cells.

The term "viable cells" refers to cells which are able to grow and/or are metabolically active. Thus, if a cell is said to not be viable, also referred to as "non-viable" then a cell does not display the characteristics of a viable cell.

The term "substantially no viable cells" means that less than about 5% of the total cells are viable. Preferably, less than about 3%, more preferably less than about 1%, even more preferably less than about 0.1% of the total cells are viable.

In one embodiment the processed tobacco leaf may be processed by one or more of: curing, fermenting and/or pasteurising.

Suitably the processed tobacco leaf may be processed by curing.

Tobacco leaf may be cured by any method known in the art. In one embodiment tobacco leaf may be cured by one or more of the curing methods selected from the group consisting of: air curing, fire curing, flue curing and sun curing.

Suitably the tobacco leaf may be air cured.

Typically air curing is achieved by hanging tobacco leaf in well-ventilated barns and allowing to dry. This is usually carried out over a period of four to eight weeks. Air curing is especially suitable for burley tobacco.

Suitably the tobacco leaf may be fire cured. Fire curing is typically achieved by hanging tobacco leaf in large barns where fires of hardwoods are kept on continuous or intermittent low smoulder and usually takes between three days and ten weeks, depending on the process and the tobacco.

In another embodiment the tobacco leaf may be flue cured. Flue curing may comprise stringing tobacco leaves onto tobacco sticks and hanging them from tier-poles in curing barns. The barns usually have a flue which runs from externally fed fire boxes. Typically this results in tobacco that has been heat-cured without being exposed to smoke. Usually the temperature will be raised slowly over the course of the curing with the whole process taking approximately 1 week.

Suitably the tobacco leaf may be sun cured. This method typically involves exposure of uncovered tobacco to the sun.

Suitably the processed tobacco leaf may be processed by fermenting.

Fermentation can be carried out in any manner known in the art. Typically during fermentation, the tobacco leaves are piled into stacks (a bulk) of cured tobacco covered in e.g. burlap to retain moisture. The combination of the remaining water inside the leaf and the weight of the tobacco generates a natural heat which ripens the tobacco. The temperature in the centre of the bulk is monitored daily. In some methods every week, the entire bulk is opened. The leaves are then removed to be shaken and moistened and the bulk is rotated so that the inside leaves go outside and the bottom leaves are placed on the top of the bulk. This ensures even fermentation throughout the bulk. The additional moisture on the leaves, plus the actual rotation of the leaves themselves, generates heat, releasing the tobacco's natural ammonia and reducing nicotine, while also deepening the colour and improving the tobacco's aroma. Typically the fermentation process continues for up to 6 months, depending on the variety of tobacco, stalk position on the leaf, thickness and intended use of leaf.

Suitably the processed tobacco leaf may be processed by pasteurising. Pasteurising may be particularly preferred when the tobacco leaf will be used to make a smokeless tobacco product, most preferably snus.

Tobacco leaf pasteurisation may be carried out by any method known in the art. For example pasteurisation may be carried out as detailed in J Foulds, L Ramstrom, M Burke, K Fagerstrom. Effect of smokeless tobacco (snus) on smoking and public health in Sweden. Tobacco Control (2003) 12: 349-359, the teaching of which is incorporated herein by reference.

During the production of snus pasteurisation is typically carried out by a process in which the tobacco is heat treated with steam for 24-36 hours (reaching temperatures of approximately 100° C.). This results in an almost sterile product and without wishing to be bound by theory one of the consequences of this is believed to be a limitation of further TSNA formation.

In one embodiment the pasteurisation may be steam pasteurisation.

In some embodiments the processed tobacco leaf may be cut. The processed tobacco leaf may be cut before or after processing. Suitably, the processed tobacco leaf may be cut after processing.

In some embodiments the tobacco plant, harvested leaf of a tobacco plant and/or processed tobacco leaf may be used to extract nicotine. The extraction of nicotine can be achieved using any method known in the art. For example a method for extracting nicotine from tobacco is taught in U.S. Pat. No. 2,162,738 which is incorporated herein by reference.

In another aspect the present invention provides a tobacco product.

In one embodiment the tobacco product may be prepared from a tobacco plant of the invention or a part thereof.

Suitably the tobacco plant or part thereof may be propagated from a tobacco plant propagation material according to the present invention.

The term "part thereof" as used herein in the context of a tobacco plant refers to a portion of the tobacco plant. Preferably the "part thereof" is a leaf of a tobacco plant.

In another embodiment the tobacco product may be prepared from a harvested leaf of the invention.

In a further embodiment the tobacco product may be prepared from a processed tobacco leaf of the invention.

Suitably the tobacco product may be prepared from a tobacco leaf processed by one or more of: curing, fermenting and/or pasteurising.

Suitably the tobacco product may comprise a cut tobacco leaf, optionally processed as per the foregoing embodiment.

In one embodiment the tobacco product may be a smoking article.

As used herein, the term "smoking article" can include smokeable products, such as rolling tobacco, cigarettes, cigars and cigarillos whether based on tobacco, tobacco derivatives, expanded tobacco, reconstituted tobacco or tobacco substitutes.

In another embodiment the tobacco product may be a smokeless tobacco product.

The term "smokeless tobacco product" as used herein refers to a tobacco product that is not intended to be smoked and/or subjected to combustion. In one embodiment a smokeless tobacco product may include snus, snuff, chewing tobacco or the like.

In a further embodiment the tobacco product may be a tobacco heating device.

Typically in heated smoking articles, an aerosol is generated by the transfer of heat from a heat source to a physically separate aerosol-forming substrate or material, which may be located within, around or downstream of the heat source. During smoking, volatile compounds are released from the aerosol-forming substrate by heat transfer from the heat source and entrained in air drawn through the smoking article. As the released compounds cool, they condense to form an aerosol that is inhaled by the user.

Aerosol-generating articles and devices for consuming or smoking tobacco heating devices are known in the art. They can include, for example, electrically heated aerosol-generating devices in which an aerosol is generated by the transfer of heat from one or more electrical heating elements of the aerosol-generating device to the aerosol-forming substrate of a tobacco heating device.

Suitably the tobacco heating device may be an aerosol-generating device.

Preferably the tobacco heating device may be a heat-not-burn device. Heat-not-burn devices are known in the art and release compounds by heating, but not burning, tobacco.

An example of a suitable, heat-not-burn device may be one taught in WO2013/034459 or GB2515502 which are incorporated herein by reference.

In one embodiment the aerosol-forming substrate of a tobacco heating device may be a tobacco product in accordance with the present invention.

Polynucleotides/Polypeptides/Constructs/Methods

In certain embodiments of the present invention, chimeric genes encoding a protein of interest (e.g. a LBD nitrogen-responsive transcription factor) may be transformed into plant cells leading to controlled expression of the protein of interest under the direction of a promoter. The promoters may be obtained from different sources including animals, plants, fungi, bacteria, and viruses. Promoters may also be constructed synthetically.

Exogenous genes may be introduced into plants according to the present invention by means of suitable vector, e.g. plant transformation vectors. A plant transformation vector may comprise an expression cassette comprising 5'-3' in the direction of transcription, a promoter sequence, a gene of interest (e.g. a deregulated nitrate reductase) coding sequence, optionally including introns, and, optionally a 3' untranslated, terminator sequence including a stop signal for RNA polymerase and a polyadenylation signal for polyadenylase. The promoter sequence may be present in one or more copies, and such copies may be identical or variants of a promoter sequence as described above. The terminator sequence may be obtained from plant, bacterial or viral genes. Suitable terminator sequences are the pea rbcS E9 terminator sequence, the nos terminator sequence derived from the nopaline synthase gene of *Agrobacterium tumefaciens* and the 35S terminator sequence from cauliflower mosaic virus, for example. A person skilled in the art will be readily aware of other suitable terminator sequences.

The expression cassette may also comprise a gene expression enhancing mechanism to increase the strength of the promoter. An example of such an enhancer element is one derived from a portion of the promoter of the pea plastocyanin gene, and which is the subject of International patent Application No. WO 97/20056. Suitable enhancer elements may be the nos enhancer element derived from the nopaline synthase gene of *Agrobacterium tumefaciens* and the 35S enhancer element from cauliflower mosaic virus, for example. These regulatory regions may be derived from the same gene as the promoter DNA sequence or may be derived from different genes, from *Nicotiana tabacum* or other organisms, for example from a plant of the family Solanaceae, or from the subfamily Cestroideae. All of the regulatory regions should be capable of operating in cells of the tissue to be transformed.

The promoter DNA sequence may be derived from the same gene as the gene of interest (e.g. the gene the promoter is going to direct, for instance a gene encoding a the modification of a plant to increase the activity or expression of a LBD nitrogen-responsive transcription factor) coding sequence used in the present invention or may be derived from a different gene, from *Nicotiana tabacum*, or another organism, for example from a plant of the family Solanaceae, or from the subfamily Cestroideae. When referring to a "chimeric gene", it is meant that the nucleic acid sequence encoding a gene of interest (e.g. a gene encoding a deregulated nitrate reductase) is derived from a different origin (e.g. from a different gene, or from a different species) to the promoter sequence which directs its expression.

The expression cassette may be incorporated into a basic plant transformation vector, such as pBIN 19 Plus, pBI 101, or other suitable plant transformation vectors known in the art. In addition to the expression cassette, the plant transformation vector will contain such sequences as are necessary for the transformation process. These may include the *Agrobacterium* vir genes, one or more T-DNA border sequences, and a selectable marker or other means of identifying transgenic plant cells.

The term "plant transformation vector" means a construct capable of in vivo or in vitro expression. Preferably, the expression vector is incorporated in the genome of the organism. The term "incorporated" preferably covers stable incorporation into the genome.

Techniques for transforming plants are well known within the art and include *Agrobacterium*-mediated transformation, for example. The basic principle in the construction of genetically modified plants is to insert genetic information in the plant genome so as to obtain a stable maintenance of the inserted genetic material. A review of the general techniques may be found in articles by Potrykus (*Annu Rev Plant*

*Physiol Plant Mol Biol* [1991] 42:205-225) and Christon (AgroFood-Industry Hi-Tech Mar./Apr. 1994 17-27).

Typically, in *Agrobacterium*-mediated transformation a binary vector carrying a foreign DNA of interest, i.e. a chimeric gene, is transferred from an appropriate *Agrobacterium* strain to a target plant by the co-cultivation of the *Agrobacterium* with explants from the target plant. Transformed plant tissue is then regenerated on selection media, which selection media comprises a selectable marker and plant growth hormones. An alternative is the floral dip method (Clough & Bent, 1998) whereby floral buds of an intact plant are brought into contact with a suspension of the *Agrobacterium* strain containing the chimeric gene, and following seed set, transformed individuals are germinated and identified by growth on selective media. Direct infection of plant tissues by *Agrobacterium* is a simple technique which has been widely employed and which is described in Butcher D. N. et al., (1980), *Tissue Culture Methods for Plant Pathologists*, eds.: D. S. Ingrams and J. P. Helgeson, 203-208.

Further suitable transformation methods include direct gene transfer into protoplasts using polyethylene glycol or electroporation techniques, particle bombardment, microinjection and the use of silicon carbide fibres for example.

Transforming plants using ballistic transformation, including the silicon carbide whisker technique are taught in Frame B R, Drayton P R, Bagnaall S V, Lewnau C J, Bullock W P, Wilson H M, Dunwell J M, Thompson J A & Wang K (1994). Production of fertile transgenic maize plants by silicon carbide whisker-mediated transformation is taught in *The Plant Journal* 6: 941-948) and viral transformation techniques is taught in for example Meyer P, Heidmmm I & Niedenhof 1 (1992). The use of cassava mosaic virus as a vector system for plants is taught in *Gene* 110: 213-217. Further teachings on plant transformation may be found in EP-A-0449375.

In a further aspect, the present invention relates to a vector system which carries a nucleotide sequence encoding a gene of interest (e.g. a gene encoding a deregulated nitrate reductase) and introducing it into the genome of an organism, such as a plant. The vector system may comprise one vector, but it may comprise two vectors. In the case of two vectors, the vector system is normally referred to as a binary vector system. Binary vector systems are described in further detail in Gynheung Anetal, (1980), Binary Vectors, *Plant Molecular Biology Manual* A3, 1-19.

One extensively employed system for transformation of plant cells uses the Ti plasmid from *Agrobacterium tumefaciens* or a Ri plasmid from *Agrobacterium rhizogenes* Anetal., (1986), Plant Physiol. 81, 301-305 and Butcher D. N. et al., (1980), *Tissue Culture Methods for Plant Pathologists*, eds.: D. S. Ingrams and J. P. Helgeson, 203-208. After each introduction method of the desired exogenous gene according to the present invention in the plants, the presence and/or insertion of further DNA sequences may be necessary. The use of T-DNA for the transformation of plant cells has been intensively studied and is described in EP-A-120516; Hoekema, in: The Binary Plant Vector System Offset-drukkerij Kanters B. B., Amsterdam, 1985, Chapter V; Fraley, et al., *Crit. Rev. Plant Sci.*, 4:1-46; and Anetal., *EMBO J* (1985) 4:277-284.

Plant cells transformed with an exogenous gene encoding a protein of interest (e.g. a LBD nitrogen-responsive transcription factor) may be grown and maintained in accordance with well-known tissue culturing methods such as by culturing the cells in a suitable culture medium supplied with the necessary growth factors such as amino acids, plant hormones, vitamins, etc.

The term "transgenic plant" in relation to the present invention includes any plant that comprises an exogenous gene encoding a gene of interest, e.g. a gene encoding a LBD nitrogen-responsive transcription factor, according to the present invention. Preferably the exogenous gene is incorporated in the genome of the plant.

The terms "transgenic plant" and "chimeric gene" do not cover native nucleotide coding sequences in their natural environment when they are under the control of their native promoter which is also in its natural environment.

In one aspect, a nucleic acid sequence, chimeric gene, plant transformation vector or plant cell according to the present invention is in an isolated form. The term "isolated" means that the sequence is at least substantially free from at least one other component with which the sequence is naturally associated in nature and as found in nature.

In one aspect, a nucleic acid sequence, chimeric gene, plant transformation vector or plant cell according to the invention is in a purified form. The term "purified" means in a relatively pure state, e.g. at least about 90% pure, or at least about 95% pure or at least about 98% pure.

The term "nucleotide sequence" as used herein refers to an oligonucleotide sequence or polynucleotide sequence, and variant, homologues, fragments and derivatives thereof (such as portions thereof). The nucleotide sequence may be of genomic or synthetic or recombinant origin, which may be double-stranded or single-stranded whether representing the sense or anti-sense strand.

The term "nucleotide sequence" in relation to the present invention includes genomic DNA, cDNA, synthetic DNA, and RNA. Preferably it means DNA, more preferably cDNA sequence coding for the present invention.

In a preferred embodiment, the nucleotide sequence when relating to and when encompassed by the per se scope of the present invention does not include the native nucleotide sequence according to the present invention when in its natural environment and when it is linked to its naturally associated sequence(s) that is/are also in its/their natural environment. For ease of reference, we shall call this preferred embodiment the "non-native nucleotide sequence". In this regard, the term "native nucleotide sequence" means an entire nucleotide sequence that is in its native environment and when operatively linked to an entire promoter with which it is naturally associated, which promoter is also in its native environment. However, the amino acid sequence encompassed by scope the present invention can be isolated and/or purified post expression of a nucleotide sequence in its native organism. Preferably, however, the amino acid sequence encompassed by scope of the present invention may be expressed by a nucleotide sequence in its native organism but wherein the nucleotide sequence is not under the control of the promoter with which it is naturally associated within that organism.

Typically, the nucleotide sequence encompassed by the scope of the present invention is prepared using recombinant DNA techniques (i.e. recombinant DNA). However, in an alternative embodiment of the invention, the nucleotide sequence could be synthesised, in whole or in part, using chemical methods well known in the art (see Caruthers M H et al., (1980) *Nuc Acids Res Symp Ser* 215-23 and Horn T et al., (1980) *Nuc Acids Res Symp Ser* 225-232).

A nucleotide sequence encoding either a protein which has the specific properties as defined herein or a protein which is suitable for modification may be identified and/or isolated and/or purified from any cell or organism producing said protein. Various methods are well known within the art for the identification and/or isolation and/or purification of nucleotide sequences. By way of example, PCR amplification techniques to prepare more of a sequence may be used once a suitable sequence has been identified and/or isolated and/or purified.

By way of further example, a genomic DNA and/or cDNA library may be constructed using chromosomal DNA or messenger RNA from the organism producing the enzyme. If the amino acid sequence of the enzyme is known, labelled oligonucleotide probes may be synthesised and used to identify enzyme-encoding clones from the genomic library prepared from the organism. Alternatively, a labelled oligonucleotide probe containing sequences homologous to another known enzyme gene could be used to identify enzyme-encoding clones. In the latter case, hybridisation and washing conditions of lower stringency are used.

In a yet further alternative, the nucleotide sequence encoding the enzyme may be prepared synthetically by established standard methods, e.g. the phosphoroamidite method described by Beucage S. L. et al., (1981) *Tetrahedron Letters* 22, p 1859-1869, or the method described by Matthes et al., (1984) *EMBO J.* 3, p 801-805. In the phosphoroamidite method, oligonucleotides are synthesised, e.g. in an automatic DNA synthesiser, purified, annealed, ligated and cloned in appropriate vectors.

The nucleotide sequence may be of mixed genomic and synthetic origin, mixed synthetic and cDNA origin, or mixed genomic and cDNA origin, prepared by ligating fragments of synthetic, genomic or cDNA origin (as appropriate) in accordance with standard techniques. Each ligated fragment corresponds to various parts of the entire nucleotide sequence. The DNA sequence may also be prepared by polymerase chain reaction (PCR) using specific primers, for instance as described in U.S. Pat. No. 4,683,202 or in Saiki R K et al., (*Science* (1988) 239, pp 487-491).

The scope of the present invention also encompasses amino acid sequences of enzymes having the specific properties as defined herein.

As used herein, the term "amino acid sequence" is synonymous with the term "polypeptide" and/or the term "protein". In some instances, the term "amino acid sequence" is synonymous with the term "peptide". In some instances, the term "amino acid sequence" is synonymous with the term "enzyme".

The amino acid sequence may be prepared and/or isolated from a suitable source, or it may be made synthetically or it may be prepared by use of recombinant DNA techniques.

Preferably the amino acid sequence when relating to and when encompassed by the per se scope of the present invention is not a native enzyme. In this regard, the term "native enzyme" means an entire enzyme that is in its native environment and when it has been expressed by its native nucleotide sequence.

The present invention also encompasses the use of sequences having a degree of sequence identity or sequence homology with amino acid sequence(s) of a polypeptide having the specific properties defined herein or of any nucleotide sequence encoding such a polypeptide (hereinafter referred to as a "homologous sequence(s)"). Here, the term "homologue" means an entity having a certain homology with the subject amino acid sequences and the subject nucleotide sequences. Here, the term "homology" can be equated with "identity".

The homologous amino acid sequence and/or nucleotide sequence and/or fragments should provide and/or encode a polypeptide which retains the functional activity and/or enhances the activity of the enzyme.

Typically, the homologous sequences will comprise the same active sites etc. as the subject amino acid sequence for instance or will encode the same active sites. Although homology can also be considered in terms of similarity (i.e. amino acid residues having similar chemical properties/functions), in the context of the present invention it is preferred to express homology in terms of sequence identity.

In one embodiment, a homologous sequence is taken to include an amino acid sequence or nucleotide sequence which has one or several additions, deletions and/or substitutions compared with the subject sequence.

In one embodiment the present invention relates to a protein whose amino acid sequence is represented herein or a protein derived from this (parent) protein by substitution, deletion or addition of one or several amino acids, such as 2, 3, 4, 5, 6, 7, 8, 9 amino acids, or more amino acids, such as 10 or more than 10 amino acids in the amino acid sequence of the parent protein and having the activity of the parent protein.

In one embodiment the present invention relates to a nucleic acid sequence (or gene) encoding a protein whose amino acid sequence is represented herein or encoding a protein derived from this (parent) protein by substitution, deletion or addition of one or several amino acids, such as 2, 3, 4, 5, 6, 7, 8, 9 amino acids, or more amino acids, such as 10 or more than 10 amino acids in the amino acid sequence of the parent protein and having the activity of the parent protein.

Homology or identity comparisons can be conducted by eye, or more usually, with the aid of readily available sequence comparison programs. These commercially available computer programs can calculate % homology between two or more sequences.

% homology or % identity may be calculated over contiguous sequences, i.e. one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified.

However, it is preferred to use the default values when using such software for sequence comparisons.

Calculation of maximum % homology therefore firstly requires the production of an optimal alignment, taking into consideration gap penalties. A suitable computer program for carrying out such an alignment is the Vector NTI (Invitrogen Corp.). Examples of software that can perform sequence comparisons include, but are not limited to, the BLAST package (see Ausubel et al 1999 Short Protocols in Molecular Biology, 4th Ed—Chapter 18), BLAST 2 (see FEMS Microbiol Lett 1999 174(2): 247-50; FEMS Microbiol Lett 1999 177(1): 187-8 and tatiana(ncbi.nlm.nih.gov), FASTA (Altschul et al 1990 J. Mol. Biol. 403-410) and AlignX for example. At least BLAST, BLAST 2 and FASTA are available for offline and online searching (see Ausubel et al 1999, pages 7-58 to 7-60).

Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. Vector NTI programs generally use either the public default values or a custom symbol comparison table if supplied (see user manual for further details). For some applications, it is preferred to use the default values for the Vector NTI package.

Alternatively, percentage homologies may be calculated using the multiple alignment feature in Vector NTI (Invitrogen Corp.), based on an algorithm, analogous to CLUSTAL (Higgins D G & Sharp P M (1988), Gene 73(1), 237-244).

Once the software has produced an optimal alignment, it is possible to calculate % homology, preferably % sequence identity. The software typically does this as part of the sequence comparison and generates a numerical result.

Should Gap Penalties be used when determining sequence identity, then preferably the following parameters are used for pairwise alignment:

| FOR BLAST | | | |
|---|---|---|---|
| GAP OPEN | | 0 | |
| GAP EXTENSION | | 0 | |
| FOR CLUSTAL | DNA | PROTEIN | |
| WORD SIZE | 2 | 1 | K triple |
| GAP PENALTY | 15 | 10 | |
| GAP EXTENSION | 6.66 | 0.1 | |

In one embodiment, CLUSTAL may be used with the gap penalty and gap extension set as defined above.

In some embodiments the gap penalties used for BLAST or CLUSTAL alignment may be different to those detailed above. The skilled person will appreciate that the standard parameters for performing BLAST and CLUSTAL alignments may change periodically and will be able to select appropriate parameters based on the standard parameters detailed for BLAST or CLUSTAL alignment algorithms at the time.

Suitably, the degree of identity with regard to a nucleotide sequence is determined over at least 20 contiguous nucleotides, preferably over at least 30 contiguous nucleotides, preferably over at least 40 contiguous nucleotides, preferably over at least 50 contiguous nucleotides, preferably over at least 60 contiguous nucleotides, preferably over at least 100 contiguous nucleotides.

Suitably, the degree of identity with regard to a nucleotide sequence may be determined over the whole sequence.

The sequences may also have deletions, insertions or substitutions of amino acid residues which produce a silent change and result in a functionally equivalent substance. Deliberate amino acid substitutions may be made on the basis of similarity in polarity, charge, solubility, hydrophobicity, hydrophilicity, and/or the amphipathic nature of the residues as long as the secondary binding activity of the substance is retained. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine.

Conservative substitutions may be made, for example according to the Table below. Amino acids in the same block in the second column and preferably in the same line in the third column may be substituted for each other:

| ALIPHATIC | Non-polar | G A P |
| | | I L V |
| | Polar - uncharged | C S T M |
| | | N Q |
| | Polar - charged | D E |
| | | K R |
| AROMATIC | | H F W Y |

The present invention also encompasses homologous substitution (substitution and replacement are both used herein to mean the interchange of an existing amino acid residue, with an alternative residue) that may occur i.e. like-for-like substitution such as basic for basic, acidic for acidic, polar for polar etc. Non-homologous substitution may also occur i.e. from one class of residue to another or alternatively involving the inclusion of unnatural amino acids such as ornithine (hereinafter referred to as Z), diaminobutyric acid ornithine (hereinafter referred to as B), norleucine ornithine (hereinafter referred to as O), pyriylalanine, thienylalanine, naphthylalanine and phenylglycine.

Replacements may also be made by unnatural amino acids include; alpha* and alpha-disubstituted* amino acids, N-alkyl amino acids*, lactic acid*, halide derivatives of natural amino acids such as trifluorotyrosine*, p-Cl-phenylalanine*, p-Br-phenylalanine*, p-I-phenylalanine*, L-allylglycine*, β-alanine*, L-α-amino butyric acid*, L-γ-amino butyric acid*, L-α-amino isobutyric acid*, L-ε-amino caproic acid#, 7-amino heptanoic acid*, L-methionine sulfone#*, L-norleucine*, L-norvaline*, p-nitro-L-phenylalanine*, L-hydroxyproline#, L-thioproline*, methyl derivatives of phenylalanine (Phe) such as 4-methyl-Phe*, pentamethyl-Phe*, L-Phe (4-amino)#, L-Tyr (methyl)*, L-Phe (4-isopropyl)*, L-Tic (1,2,3,4-tetrahydroisoquinoline-3-carboxyl acid)*, L-diaminopropionic acid # and L-Phe (4-benzyl)*. The notation * has been utilised for the purpose of the discussion above (relating to homologous or non-homologous substitution), to indicate the hydrophobic nature of the derivative whereas # has been utilised to indicate the hydrophilic nature of the derivative, #* indicates amphipathic characteristics.

Variant amino acid sequences may include suitable spacer groups that may be inserted between any two amino acid residues of the sequence including alkyl groups such as methyl, ethyl or propyl groups in addition to amino acid spacers such as glycine or β-alanine residues. A further form of variation, involves the presence of one or more amino acid residues in peptoid form, will be well understood by those skilled in the art. For the avoidance of doubt, "the peptoid form" is used to refer to variant amino acid residues wherein the α-carbon substituent group is on the residue's nitrogen atom rather than the α-carbon. Processes for preparing peptides in the peptoid form are known in the art, for example Simon R J et al., *PNAS* (1992) 89(20), 9367-9371 and Horwell D C, *Trends Biotechnol*. (1995) 13(4), 132-134.

The nucleotide sequences for use in the present invention may include within them synthetic or modified nucleotides. A number of different types of modification to oligonucleotides are known in the art. These include methylphosphonate and phosphorothioate backbones and/or the addition of acridine or polylysine chains at the 3' and/or 5' ends of the molecule. For the purposes of the present invention, it is to be understood that the nucleotide sequences described herein may be modified by any method available in the art. Such modifications may be carried out in order to enhance the in vivo activity or life span of nucleotide sequences of the present invention.

The present invention also encompasses sequences that are complementary to the nucleic acid sequences of the present invention or sequences that are capable of hybridising either to the sequences of the present invention or to sequences that are complementary thereto.

The term "hybridisation" as used herein shall include "the process by which a strand of nucleic acid joins with a complementary strand through base pairing" as well as the process of amplification as carried out in polymerase chain reaction (PCR) technologies.

The present invention also relates to nucleotide sequences that can hybridise to the nucleotide sequences of the present invention (including complementary sequences of those presented herein).

Preferably, hybridisation is determined under stringent conditions (e.g. 50° C. and 0.2×SSC {1×SSC=0.15 M NaCl, 0.015 M Na$_3$citrate pH 7.0}).

More preferably, hybridisation is determined under high stringent conditions (e.g. 65° C. and 0.1×SSC {1×SSC=0.15 M NaCl, 0.015 M Na$_3$citrate pH 7.0}).

In one aspect the sequence for use in the present invention is a synthetic sequence—i.e. a sequence that has been prepared by in vitro chemical or enzymatic synthesis. It includes, but is not limited to, sequences made with optimal codon usage for host organisms.

The term "expression vector" means a construct capable of in vivo or in vitro expression.

Preferably, the expression vector is incorporated into the genome of a suitable host organism. The term "incorporated" preferably covers stable incorporation into the genome.

The nucleotide sequence of the present invention may be present in a vector in which the nucleotide sequence is operably linked to regulatory sequences capable of providing for the expression of the nucleotide sequence by a suitable host organism.

The vectors for use in the present invention may be transformed into a suitable host cell as described herein to provide for expression of a polypeptide of the present invention.

The choice of vector e.g. a plasmid, cosmid, or phage vector will often depend on the host cell into which it is to be introduced.

Vectors may be used in vitro, for example for the production of RNA or used to transfect, transform, transduce or infect a host cell.

Thus, in a further embodiment, the invention provides a method of making nucleotide sequences of the present invention by introducing a nucleotide sequence of the present invention into a replicable vector, introducing the vector into a compatible host cell, and growing the host cell under conditions which bring about replication of the vector.

The vector may further comprise a nucleotide sequence enabling the vector to replicate in the host cell in question. Examples of such sequences are the origins of replication of plasmids pUC19, pACYC177, pUB110, pE194, pAMB1 and pIJ702.

In some applications, the nucleotide sequence for use in the present invention is operably linked to a regulatory sequence which is capable of providing for the expression of the nucleotide sequence, such as by the chosen host cell. By way of example, the present invention covers a vector comprising the nucleotide sequence of the present invention operably linked to such a regulatory sequence, i.e. the vector is an expression vector.

The term "operably linked" refers to a juxtaposition wherein the components described are in a relationship permitting them to function in their intended manner. A regulatory sequence "operably linked" to a coding sequence is ligated in such a way that expression of the coding sequence is achieved under condition compatible with the control sequences.

The term "regulatory sequences" includes promoters and enhancers and other expression regulation signals.

The term "promoter" is used in the normal sense of the art, e.g. an RNA polymerase binding site.

Enhanced expression of the nucleotide sequence encoding the enzyme of the present invention may also be achieved by the selection of heterologous regulatory regions, e.g. promoter, secretion leader and terminator regions.

Preferably, the nucleotide sequence according to the present invention is operably linked to at least a promoter.

The term "construct"—which is synonymous with terms such as "conjugate", "cassette" and "hybrid"—includes a nucleotide sequence for use according to the present invention directly or indirectly attached to a promoter.

An example of an indirect attachment is the provision of a suitable spacer group such as an intron sequence, such as the Sh1-intron or the ADH intron, intermediate the promoter and the nucleotide sequence of the present invention. The same is true for the term "fused" in relation to the present invention which includes direct or indirect attachment. In some cases, the terms do not cover the natural combination of the nucleotide sequence coding for the protein ordinarily associated with the wild type gene promoter and when they are both in their natural environment.

The construct may even contain or express a marker, which allows for the selection of the genetic construct.

A review of the general techniques used for transforming plants may be found in articles by Potrykus (*Annu Rev Plant Physiol Plant Mol Biol* [1991] 42:205-225) and Christou (Agro-Food-Industry Hi-Tech Mar./Apr. 1994 17-27). Further teachings on plant transformation may be found in EP-A-0449375.

Unless defined otherwise, all technical and scientific terms used herein have the same meaning as commonly understood by one of ordinary skill in the art to which this disclosure belongs. Singleton, et al., DICTIONARY OF MICROBIOLOGY AND MOLECULAR BIOLOGY, 20 ED., John Wiley and Sons, New York (1994), and Hale &

Marham, THE HARPER COLLINS DICTIONARY OF BIOLOGY, Harper Perennial, N.Y. (1991) provide one of skill with a general dictionary of many of the terms used in this disclosure.

This disclosure is not limited by the exemplary methods and materials disclosed herein, and any methods and materials similar or equivalent to those described herein can be used in the practice or testing of embodiments of this disclosure. Numeric ranges are inclusive of the numbers defining the range. Unless otherwise indicated, any nucleic acid sequences are written left to right in 5' to 3' orientation; amino acid sequences are written left to right in amino to carboxy orientation, respectively.

The headings provided herein are not limitations of the various aspects or embodiments of this disclosure which can be had by reference to the specification as a whole. Accordingly, the terms defined immediately below are more fully defined by reference to the specification as a whole.

Amino acids are referred to herein using the name of the amino acid, the three letter abbreviation or the single letter abbreviation.

The term "protein", as used herein, includes proteins, polypeptides, and peptides.

As used herein, the term "amino acid sequence" is synonymous with the term "polypeptide" and/or the term "protein". In some instances, the term "amino acid sequence" is synonymous with the term "peptide". In some instances, the term "amino acid sequence" is synonymous with the term "enzyme".

The terms "protein" and "polypeptide" are used interchangeably herein. In the present disclosure and claims, the conventional one-letter and three-letter codes for amino acid residues may be used. The 3-letter code for amino acids as defined in conformity with the IUPACIUB Joint Commission on Biochemical Nomenclature (JCBN). It is also understood that a polypeptide may be coded for by more than one nucleotide sequence due to the degeneracy of the genetic code.

Other definitions of terms may appear throughout the specification. Before the exemplary embodiments are described in more detail, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within this disclosure. The upper and lower limits of these smaller ranges may independently be included or excluded in the range, and each range where either, neither or both limits are included in the smaller ranges is also encompassed within this disclosure, subject to any specifically excluded limit in the stated range. Where the stated range includes one or both of the limits, ranges excluding either or both of those included limits are also included in this disclosure.

It must be noted that as used herein and in the appended claims, the singular forms "a", "an", and "the" include plural referents unless the context clearly dictates otherwise. Thus, for example, reference to "an enzyme" or "a nitrate reductase" includes a plurality of such candidate agents and equivalents thereof known to those skilled in the art, and so forth.

The publications discussed herein are provided solely for their disclosure prior to the filing date of the present application. Nothing herein is to be construed as an admission that such publications constitute prior art to the claims appended hereto.

Advantages

The key advantage associated with the present invention is a reduction of tobacco-specific nitrosamine concentration (e.g. NNK) in a tobacco product prepared from a tobacco plant which has not been modified to increase the activity or expression of a LBD nitrogen-responsive transcription factor.

The invention will now be described, by way of example only, with reference to the following Figures and Examples.

EXAMPLES

Example 1

LBD Cloning

The LBD genes LBD37 (At5g67420.1), LBD38 (At3g49940.1) and LBD39 (At4g37540.1) were isolated from *A. thaliana* cDNA. They were preliminarily cloned into a TOPO® shuttle vector (available from Life Technologies) then subsequently transformed into a pBNP binary vector containing the constitutive carnation etched ring virus (CERV) promoter, a SAG12 senescence-specific promoter and a nopaline synthase (nos) terminator. Once all sequence analysis had deemed the construct correct it was subsequently transformed into the *Agrobacterium* LBA4404 (available from Clontech Laboratories, Inc.) and transformed into burley PH2517.

Example 2

Transformation of Tobacco

Burley PH2517 plants were transformed using the method of leaf disk co-cultivation, as described by Horsch et al. (Science 227: 1229-1231, 1985).

An overnight culture of the transformed *Agrobacterium* was set up in 50 ml of LB broth plus 1 g/L glucose with relevant antibiotics. This was grown at 27° C. until an $OD_{600}$ of between 0.6 and 0.99 was reached.

The youngest two fully expanded leaves were taken from 7-week old tobacco plants and surface-sterilised in 8% Domestos™ for 10 minutes and washed 4 times with sterile distilled water. Leaf disks were then cut using an 11 mm cork-borer and inoculated in the *Agrobacterium* suspension for two minutes. The discs were then blotted between sheets of sterile filter paper and 10 disks/plate were placed on MS 3% sucrose+2.2 µM BAP+0.27 µM NAA plates. The plates were then incubated for 2 days. Discs were then transferred to plates of the same MS BN media supplemented with 500 g/l Cefotaxime and 100 g/l kanamycin. The discs were transferred onto fresh plates of the above medium every 2 weeks until shoots started to form. Shoots were excised as they appeared and transferred to plates containing LS media+3% sucrose+0.5 µM BAP supplemented with 500 mg/l Cefotaxime and 100 mg/l kanamycin. Once large enough (~2 weeks) these were transferred to jars of LS media+3% sucrose+0.5 µM BAP supplemented with 500 mg/l Cefotaxime. The shoots were transferred, in jars, to LS media+3% sucrose+250 mg/l Cefotaxime after approximately 3 weeks. After a further 3-4 weeks, the plants were finally transferred to LS media+3% sucrose (no antibiotics) and allowed to produce roots. Once the plants were rooted they were transferred to soil in the greenhouse. Growth conditions in tissue culture are 24° C.+/−1° C., 16 hour daylight.

Example 3

TSNA Levels Determination

The TSNA analysis was subcontracted to Labstat® International ULC (62 Manitou Drive, Kitchener, Ontario, N2C 1L3). The method used by Labstat is based on the following literature:

Wu, W.; Ashley, D. L.; Watson, C. H. Anal. Chem. (2003) 75: 4827-4832.

Wagner, K. A.; Finkel, N. H.; Fossett, J. E.; Gillman, I. G. Anal. Chem. (2005) 77: 1001-1006.

Lee, J-M.; Shin J-W.; Oh, I H.; Lee U-C.; Rhee M-S. (2004) Coresta Congress Kyoto. Paper SS20; See http://www.coresta.org/Past_abstracts/Kyoto2004-SmokeTech.pdf Chwojdak, C. A.; Self, D. A.; Wheeler, H. R. A collaborative, Harmonized LC-MS/MS Method for the determination of Tobacco Specific Nitrosamines (TSNA) in Tobacco and Tobacco Related Materials. 61$^{st}$ *Tobacco Science Research Conference,* Charlotte, N.C. USA. Sep. 24, 2007.

Method Synopsis:

A minimum sample size of 100 g of cured tobacco was required for the testing. Tobacco product was ground and sieved to ensure <4 mm particle size, with analysis being initiated as soon as possible following the preparation of the laboratory composite.

A certain amount of an internal standard solution containing four deuterium labelled TSNA analogues (i.e., NNN-$d_4$, NAT-$d_4$, NAB-$d_4$, NNK-$d_4$) was spiked onto a tobacco product (0.75 g) and then the TSNA compounds were extracted into an aqueous ammonium acetate solution on a wrist action shaker. The extract was then filtered and subject to LC-MSMS analysis using positive electrospray ionization (ESI). Two mass transition pairs for each analyte can be used to assist analyte confirmation and quantification. The most intensive pairs were used for quantification; the less intense transition pairs were used as qualifiers for further compound confirmation.

Figure 3:
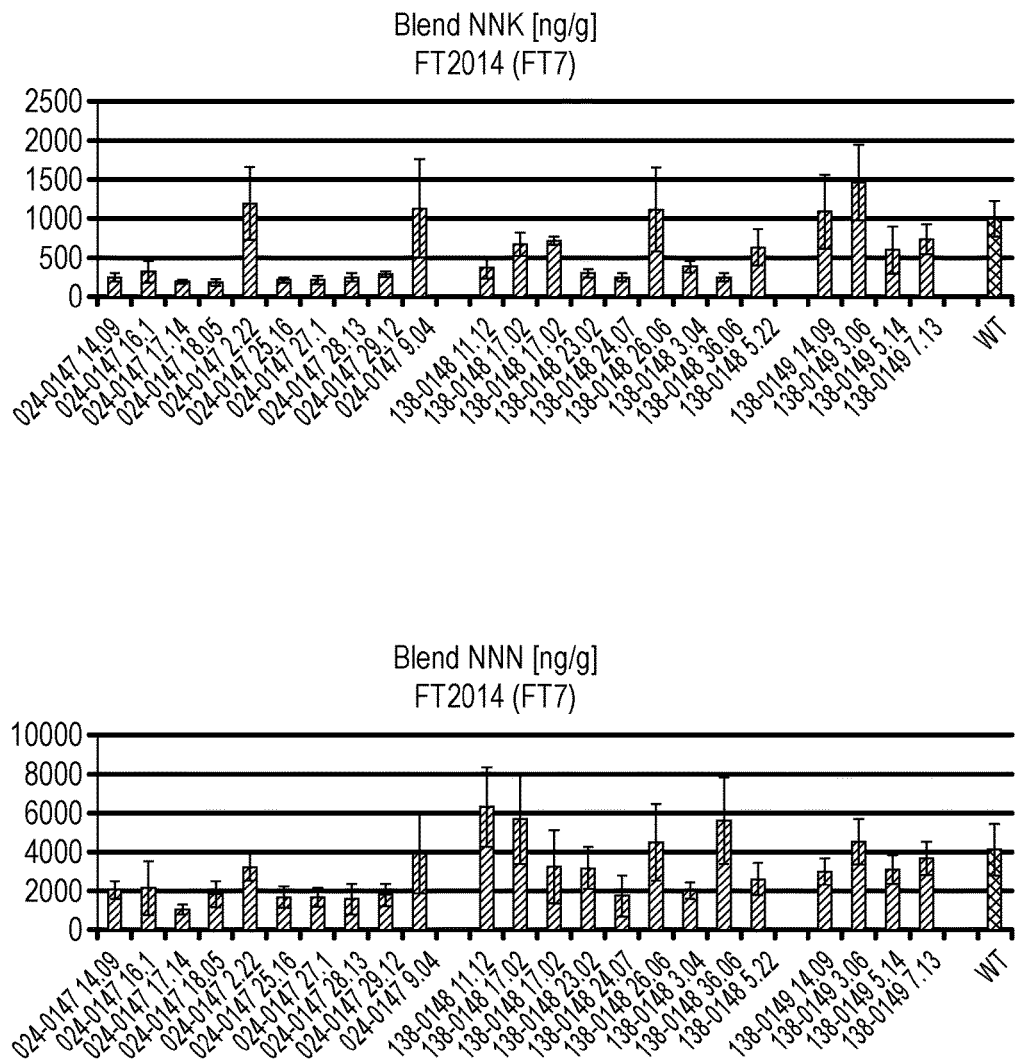
FIG. 3 shows the NNK and NNN levels in cured tobacco produced from plants transformed with the 024-0147 (LBD37 on constitutive promoter), 0138-0148 (LBD38 on senescence-specific promoter) and 0138-0149 (LBD39 on senescence-specific promoter) constructs.

Results:

FIG. 3 shows that NNK and NNN levels in cured tobacco produced from plants expressing a construct of LBD37 on a constitutive promoter (024-0147) are significantly reduced in comparison to wild type plants. Cured tobacco produced from plants expressing a construct of LBD38 on a senescence-specific promoter (138-0148) also showed a noticeable reduction in NNK.

As the overexpression of LBD38 and 39 implied a fitness cost to the plant, LBD38 and 39 were expressed under the control of a senescence promoter. However, the effect of the transgene being lessened, so is the effect on the reduction of TSNA.

The extent of the decrease in NNK content in the transgenic compared to the control is clearly lower for the gene expressed with a senescence promoter (0138-0148 and 0138-0149) compared to the constitutive promoter (024-0147). However, the effect produced by LBD37 on NNK levels is striking for 80% of the lines, showing an averaged decrease of 3- to 6-fold. The decrease in NNN is also statistically significant for the plants carrying the LBD37 gene. A decrease of 2 to 4 times less NNN was observed compared to the wild type control.

Example 4

Analysis of Tobacco Leaf Amino Acid Content (T1)

The amino acid content of wild-type and transgenic Burley PH2517 plants was determined using the EZ: Faast LC/MS kit supplied by Phenomenex. All the reagents and the supplies, including the HPLC column, are components of the kit. All the steps of the procedure are provided in the User's manuals KH0-7338 which are used as a protocol.

The method involves solid phase extraction of the samples to be analysed, followed by a derivatization and a liquid/liquid extraction. The derivatized samples were analyzed quickly by liquid chromatography-mass spectrometry (LC-MS).

The solid phase extraction was performed via a sorbent packed tip that binds amino acids while allowing interfering compounds to flow through. Amino acids which were bound to the sorbent were then extruded into the sample vial and quickly derivatized with reagent at room temperature in aqueous solution. Derivatized amino acids concomitantly migrated to the organic layer for additional separation from interfering compounds. The organic layer was then removed, evaporated and re-dissolved in aqueous mobile phase and analyzed on a LC-MS system.

4 independent plants from each constructs were grown in the greenhouse. The plants were grown for 14 weeks when the leaf number 10 (middle position) was sampled and flash frozen in liquid nitrogen. Results presented below are obtained from the average of the main amino acid content. 12 wild type plants were grown in the same conditions and the results presented for the control represent the average amino acids content for the 12 middle leaves.

Results and Discussion

It is well known that TSNA content in cured tobacco leaves is related to the nitrogenous species present in the leaf at harvest time. Nitrogen assimilation, nitrogen transport, central nitrogen metabolism and recycling at senescence are all events involved in the nitrogen status of a plant. Although very complex, it is also recognized that the amino acids content is a reflection of the nitrogen status of the plant and potentially an indication of the TSNAs precursor levels.

Figure 2:
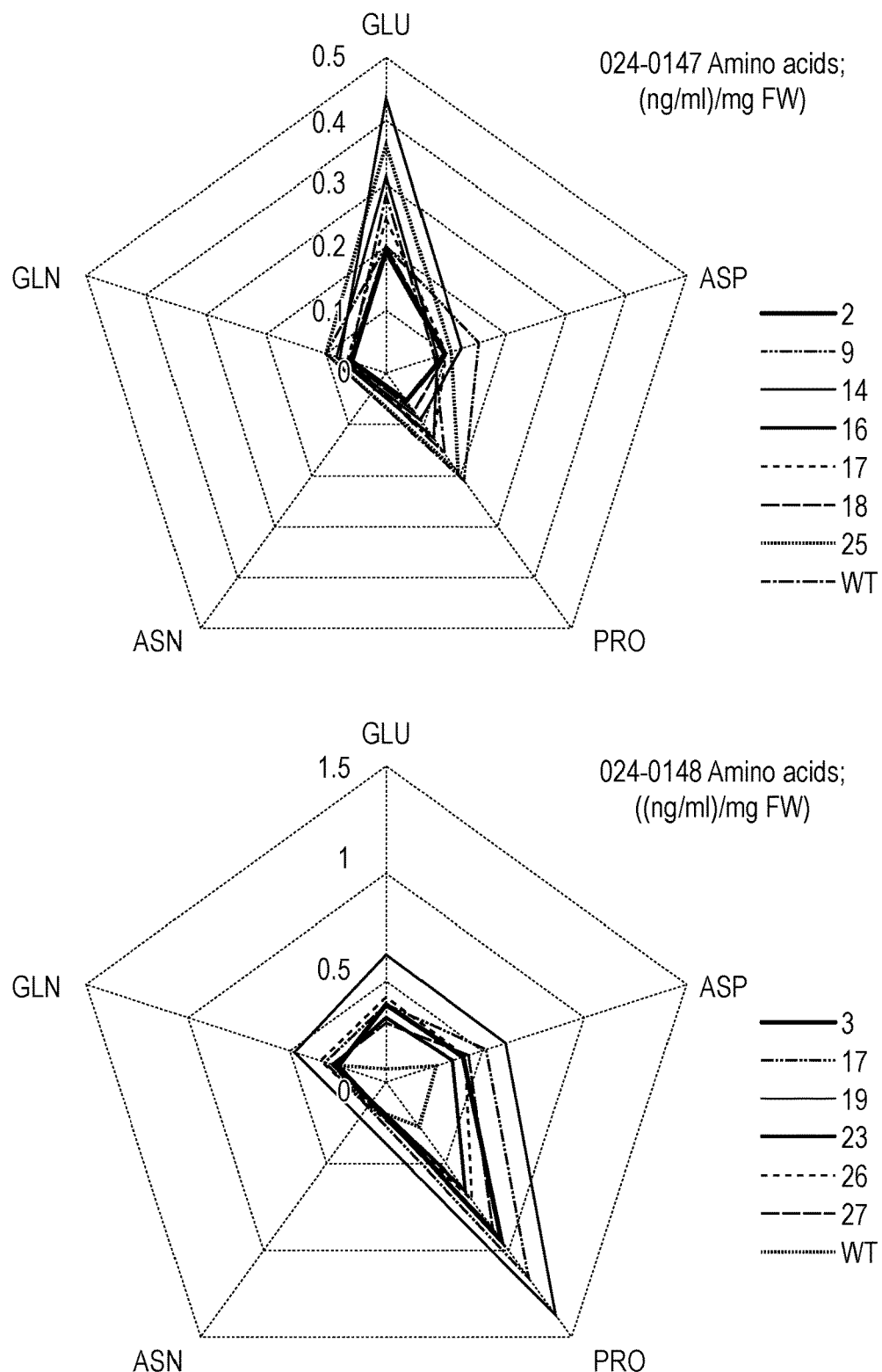
FIG. 2 shows the amino acids levels of the 024-0147 construct (LBD37, constitutive promoter), the 024-0148 construct (LBD38, constitutive promoter), the 0138-0148 construct (LBD38, senescence-specific promoter) and the 024-0149 construct (LBD39, constitutive promoter).

The results presented in FIG. 2 show that the amino acid distribution, and therefore the nitrogen status of plants is affected by the construct. Glutamate, Glutamine and Asparagine are clearly the 3 most abundant amino acids in both the wild type and the transgenics plants. However, for many transgenic lines carrying the genes LBD37, 38 or 39, the abundance of total amino acids is increased compared to the wild type. Also, the proportion of glutamate and Proline to the total quantity of amino acids is shown to be increased compared to other amino acids in the transgenics. This demonstrates the modification of the nitrogen species distribution in the plants carrying an overexpression of the 3 LBD genes.

Example 5

Analysis of Tobacco Nicotine Levels

The Nicotine analysis was subcontracted to Labstat. The method used by Labstat is based on the following literature:

Imperial Tobacco Canada Limited, Procedures analytical Services, Procedure 11; "Simultaneous Determination of Sugars and Total Alkaloids in Tobacco".

Bran & Luebbe, Auto Analyser 3 (AA3) Reference Manual.

Method Synopsis:

Ground tobacco was extracted with Type 1 water then filtered. The extract was then analysed on a Bran & Luebbe Auto Analyser 3 (AA3). Each sample underwent an on-line dilution with a buffered sodium hydroxide solution and dialyzed into a stream of sulfanilic acid. The eluent was reacted with cyanogen chloride to form a yellowish-green dye and the absorbance was read in the colorimeter at 460 nm.

Figure 4:
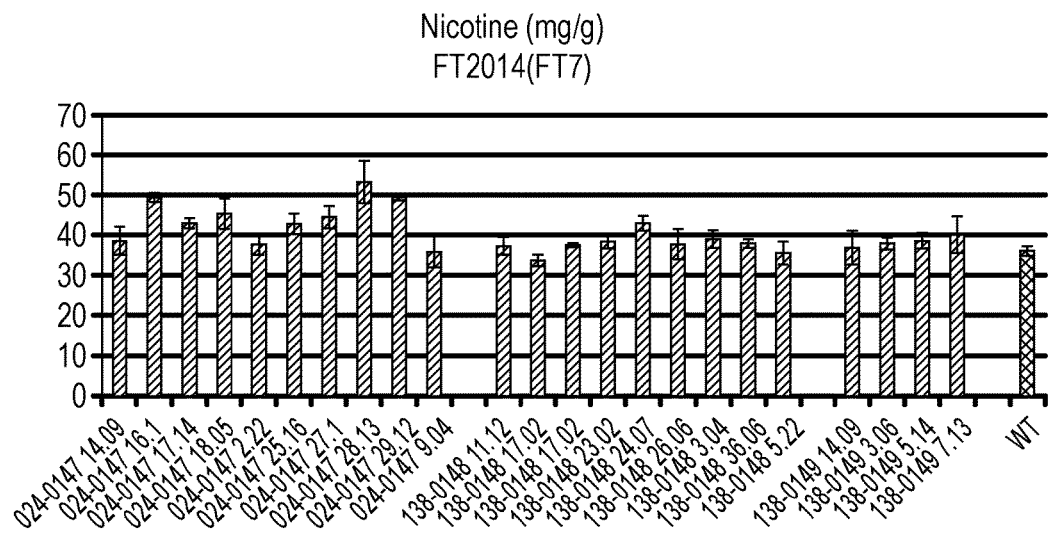
FIG. 4 shows the nicotine levels in ground tobacco produced from plants transformed with the 024-0147 (LBD37 on constitutive promoter), 0138-0148 (LBD38 on senescence-specific promoter) and 0138-0149 (LBD39 on senescence-specific promoter) constructs.
Figure 5:
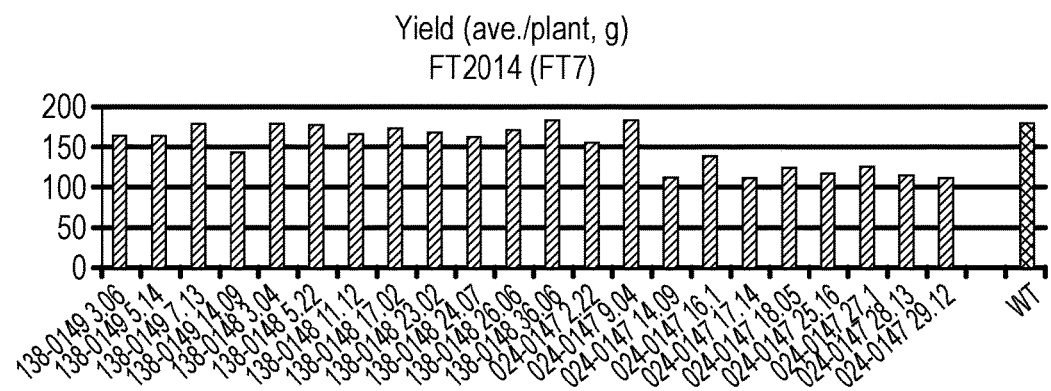
FIG. 5 shows the yield of tobacco plants transformed with the 0138-0149 (LBD39 on senescence-specific promoter), 0138-0148 (LBD38 on senescence-specific promoter) and 024-0147 (LBD37 on constitutive promoter) constructs.

Results:

The results of the nicotine level analysis presented in FIG. 4 show that expression of the LBD37, LBD38 and LBD39 genes in the plants resulted in a slight increase in nicotine content of the resulting tobacco compared to wild type. Since nicotine is a nitrogen-rich metabolite, this result is another indication of the modification of the nitrogen distribution/metabolism in the transgenic plants. FIG. 5 shows that the yield was essentially the same as wild type for the plants expressing LBD38 and LBD39 under a senescence promoter (0138-0148 and 0138-0149) but was slightly reduced for the plants expressing LBD37 with a constitutive promoter (024-0147).

All publications mentioned in the above specification are herein incorporated by reference. Various modifications and variations of the described methods and system of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in biochemistry and biotechnology or related fields are intended to be within the scope of the following claims.

What is claimed is:

1. A method of reducing at least one tobacco-specific nitrosamine (TSNA) or a precursor thereto in a tobacco plant, comprising modifying the plant by increasing the activity or expression of a LBD (lateral organ bound domain) nitrogen-responsive transcription factor in said tobacco plant, wherein the LBD nitrogen-responsive transcription factor is LBD37, LBD38 or LBD39, wherein the LBD nitrogen-responsive transcription factor comprises a polypeptide sequence shown herein as SEQ ID NO: 2, SEQ ID NO: 4 or SEQ ID NO: 6, or a polypeptide having at least 90% identity with SEQ ID NO: 2, SEQ ID NO: 4 or SEQ ID NO: 6, and wherein the concentration or total content of at least one TSNA or a precursor thereto is reduced in a tobacco leaf, a harvested leaf, or a processed tobacco leaf, when compared to a tobacco plant which has not been modified to increase the activity or expression of a LBD nitrogen-responsive transcription factor.

2. The method according to claim 1 wherein the concentration or total content of at least one TSNA, which is nicotine-derived nitrosamine ketone (NNK), nitrosonornicotine (NNN), nitrosoanatabine (NAT) or N-nitrosoanabasine (NAB), is reduced.

3. The method according to claim 1 comprising expressing within the plant a polynucleotide comprising a nucleic acid sequence encoding the LBD nitrogen-responsive transcription factor.

4. The method according to claim 3 wherein said polynucleotide comprises the nucleic acid sequence encoding the LBD nitrogen-responsive transcription factor operably linked with a heterologous promoter for directing transcription of said nucleic acid sequence in said plant.

5. The method according to claim 4 wherein said promoter is a leaf-specific promoter.

6. The method according to claim 4 wherein said promoter is a constitutive or senescence-specific promoter.

7. The method according to claim 1, wherein the LBD nitrogen-responsive transcription factor polypeptide sequence comprises one or more of the following motifs:

i)
CX2CX6CX3C (SEQ ID NO: 10)

ii)
MSCNGCRXLRKGCX (SEQ ID NO: 7)

iii)
QXXATXFXAKFXGR (SEQ ID NO: 8)

iv)
FXSLLXEAXG; (SEQ ID NO: 9)

wherein X is any naturally occurring amino acid.

8. The method according to claim 1, wherein said LBD nitrogen-responsive transcription factor is encoded by a nucleic acid sequence comprising:

i) a polynucleotide sequence shown herein as SEQ ID NO: 1, SEQ ID NO: 3 or SEQ ID NO: 5, or ii) a polynucleotide which encodes a polypeptide comprising the amino acid sequence shown herein as SEQ ID NO 2, SEQ ID NO: 4 or SEQ ID NO: 6 or a polypeptide having at least 90% identity with SEQ ID NO: 2, SEQ ID NO: 4 or SEQ ID NO: 6, or iii) a polynucleotide sequence which differs from a polynucleotide shown in i) or ii) due to degeneracy of the genetic code.

9. A method for producing a tobacco plant, a tobacco plant propagation material, a tobacco leaf, a cut harvested tobacco leaf, a processed tobacco leaf or a cut and processed tobacco leaf which has a reduction in at least one TSNA or a precursor thereto, the method comprising modifying said tobacco plant to increase the activity or expression of a LBD nitrogen-responsive transcription factor, wherein the LBD nitrogen-responsive transcription factor is LBD37, LBD38 or LBD39, wherein the LBD nitrogen-responsive transcription factor comprises a polypeptide sequence shown herein as SEQ ID NO: 2, SEQ ID NO: 4 or SEQ ID NO: 6, or a polypeptide having at least 90% identity with SEQ ID NO: 2, SEQ ID NO: 4 or SEQ ID NO: 6, and wherein the concentration or total content of at least one TSNA or a precursor thereto is reduced in a tobacco leaf, a harvested leaf, or a processed tobacco leaf, when compared to a tobacco plant which has not been modified to increase the activity or expression of a LBD nitrogen-responsive transcription factor.

10. The method according to claim 9 wherein the concentration or total content of at least one TSNA, which is nicotine-derived nitrosamine ketone (NNK), nitrosonornicotine (NNN), nitrosoanatabine (NAT) or N-nitrosoanabasine (NAB), is reduced.

11. The method according to claim 9 comprising expressing within the plant a polynucleotide comprising a nucleic acid sequence encoding the LBD nitrogen-responsive transcription factor.

12. The method according to claim 9 wherein said polynucleotide comprises the nucleic acid sequence encoding the LBD nitrogen-responsive transcription factor operably linked with a heterologous promoter for directing transcription of said nucleic acid sequence in said plant.

13. The method according to claim 12 wherein said promoter is a leaf-specific promoter.

14. The method according to claim 12 wherein said promoter is a constitutive or senescence-specific promoter.

15. The method according to claim 9, wherein the LBD nitrogen-responsive transcription factor polypeptide sequence comprises one or more of the following motifs:

i)
CX2CX6CX3C (SEQ ID NO: 10)

ii)
MSCNGCRXLRKGCX (SEQ ID NO: 7)

iii)
QXXATXFXAKFXGR (SEQ ID NO: 8)

iv)
FXSLLXEAXG; (SEQ ID NO: 9)

wherein X is any naturally occurring amino acid.

16. The method according to claim 9, wherein said LBD nitrogen-responsive transcription factor is encoded by a nucleic acid sequence comprising:
   i) a polynucleotide sequence shown herein as SEQ ID NO: 1, SEQ ID NO: 3 or SEQ ID NO: 5, or
   ii) a polynucleotide which encodes a polypeptide comprising the amino acid sequence shown herein as SEQ ID NO 2, SEQ ID NO: 4 or SEQ ID NO: 6 or a polypeptide having at least 90% identity with SEQ ID NO: 2, SEQ ID NO: 4 or SEQ ID NO: 6, or
   iii) a polynucleotide sequence which differs from a polynucleotide shown in i) or ii) due to degeneracy of the genetic code.

17. A tobacco plant cell:
   i) comprising an exogenous LBD nitrogen-responsive transcription factor, wherein the LBD nitrogen-responsive transcription factor is LBD37, LBD38 or LBD39 and wherein the LBD nitrogen-responsive transcription factor comprises a polypeptide sequence shown herein as SEQ ID NO: 2, SEQ ID NO: 4 or SEQ ID NO: 6, or a polypeptide having at least 90% identity with SEQ ID NO: 2, SEQ ID NO: 4 or SEQ ID NO: 6: or
   ii) comprising a construct or vector comprising a nucleic acid encoding a LBD nitrogen-responsive transcription factor operably linked with a leaf-specific promoter, a leaf-preferred promoter or a senescence-specific promoter, wherein the LBD nitrogen-responsive transcription factor is LBD37, LBD38 or LBD39, and wherein the LBD nitrogen-responsive transcription factor comprises a polypeptide sequence shown herein as SEQ ID NO: 2, SEQ ID NO: 4 or SEQ ID NO: 6, or a polypeptide having at least 90% identity with SEQ ID NO: 2, SEQ ID NO: 4 or SEQ ID NO: 6.

18. The tobacco plant cell according to claim 17, wherein the LBD nitrogen-responsive transcription factor polypeptide sequence comprises one or more of the following motifs:

i)
CX2CX6CX3C (SEQ ID NO: 10)

ii)
MSCNGCRXLRKGCX (SEQ ID NO: 7)

iii)
QXXATXFXAKFXGR (SEQ ID NO: 8)

iv)
FXSLLXEAXG; (SEQ ID NO: 9)

wherein X is any naturally occurring amino acid.

19. The tobacco plant cell according to claim 17, wherein the nucleic acid sequence encoding said LBD nitrogen-responsive transcription factor comprises:
   i) a polynucleotide sequence shown herein as SEQ ID NO: 1, SEQ ID NO: 3 or SEQ ID NO: 5, or
   ii) a polynucleotide which encodes a polypeptide comprising the amino acid sequence shown herein as SEQ ID NO 2, SEQ ID NO: 4 or SEQ ID NO: 6, or
   iii) a polynucleotide sequence which differs from a polynucleotide shown in i) or ii) due to degeneracy of the genetic code.

20. A tobacco plant:
   i) which has been modified to achieve a reduction in at least one TSNA or a precursor thereto in comparison to an unmodified plant, wherein the modification is an increase in activity or expression of a LBD nitrogen-responsive transcription factor in said modified plant, wherein the LBD nitrogen-responsive transcription factor is LBD37, LBD38 or LBD39, and wherein the LBD nitrogen-responsive transcription factor comprises a polypeptide sequence shown herein as SEQ ID NO: 2, SEQ ID NO: 4 or SEQ ID NO: 6, or a polypeptide having at least 90% identity with SEQ ID NO: 2, SEQ ID NO: 4 or SEQ ID NO: 6: or
   ii) comprising an exogenous LBD nitrogen-responsive transcription factor, wherein the LBD nitrogen-responsive transcription factor is LBD37, LBD38 or LBD39 and wherein the LBD nitrogen-responsive transcription factor comprises a polypeptide sequence shown herein as SEQ ID NO: 2, SEQ ID NO: 4 or SEQ ID NO: 6, or a polypeptide having at least 90% identity with SEQ ID NO: 2, SEQ ID NO: 4 or SEQ ID NO: 6; or
   iii) comprising a construct or vector comprising a nucleic acid encoding a LBD nitrogen-responsive transcription factor operably linked with a leaf-specific promoter, a leaf-preferred promoter or a senescence-specific promoter, wherein the LBD nitrogen-responsive transcription factor is LBD37, LBD38 or LBD39, and wherein the LBD nitrogen-responsive transcription factor comprises a polypeptide sequence shown herein as SEQ ID NO: 2, SEQ ID NO: 4 or SEQ ID NO: 6, or a polypeptide having at least 90% identity with SEQ ID NO: 2, SEQ ID NO: 4 or SEQ ID NO: 6; or
   iv) comprising a tobacco plant cell according to claim 17.

21. The tobacco plant according to claim 20, wherein the LBD nitrogen-responsive transcription factor polypeptide sequence comprises one or more of the following motifs:

i)
CX2CX6CX3C (SEQ ID NO: 10)

ii)
MSCNGCRXLRKGCX (SEQ ID NO: 7)

iii)
QXXATXFXAKFXGR (SEQ ID NO: 8)

iv)
FXSLLXEAXG; (SEQ ID NO: 9)

wherein X is any naturally occurring amino acid.

22. The tobacco plant according to claim 20, wherein the nucleic acid sequence encoding said LBD nitrogen-responsive transcription factor comprises:

i) a polynucleotide sequence shown herein as SEQ ID NO: 1, SEQ ID NO: 3 or SEQ ID NO: 5, or
ii) a polynucleotide which encodes a polypeptide comprising the amino acid sequence shown herein as SEQ ID NO 2, SEQ ID NO: 4 or SEQ ID NO: 6, or
iii) a polynucleotide sequence which differs from a polynucleotide shown in i) or ii) due to degeneracy of the genetic code.

23. A tobacco plant propagation material of the tobacco plant according to claim 20, wherein the tobacco plant propagation material comprises the increase in activity or expression of the LBD nitrogen-responsive transcription factor, or the nucleic acid encoding said LBD nitrogen-responsive transcription factor.

24. The tobacco plant propagation material according to claim 23, wherein the LBD nitrogen-responsive transcription factor polypeptide sequence comprises one or more of the following motifs:

```
i)                              (SEQ ID NO: 10)
CX2CX6CX3C ii)                             (SEQ ID NO: 7)
MSCNGCRXLRKGCX iii)                            (SEQ ID NO: 8)
QXXATXFXAKFXGR iv)                             (SEQ ID NO: 9)
FXSLLXEAXG;
``` wherein X is any naturally occurring amino acid.

25. The tobacco plant propagation material according to claim 23, wherein the nucleic acid sequence encoding said LBD nitrogen-responsive transcription factor comprises:
i) a polynucleotide sequence shown herein as SEQ ID NO: 1, SEQ ID NO: 3 or SEQ ID NO: 5, or
ii) a polynucleotide which encodes a polypeptide comprising the amino acid sequence shown herein as SEQ ID NO 2, SEQ ID NO: 4 or SEQ ID NO: 6, or
iii) a polynucleotide sequence which differs from a polynucleotide shown in i) or ii) due to degeneracy of the genetic code.

26. The tobacco plant propagation material according to claim 23 wherein the tobacco is *Nicotiana tabacum* or *Nicotiana rustica*.

27. A tobacco product comprising the tobacco cell of claim 17.

28. A tobacco leaf of the tobacco plant according to claim 22, wherein the tobacco leaf comprises the nucleic acid sequence encoding said LBD nitrogen-responsive transcription factor.

29. The tobacco leaf of the tobacco plant according to claim 28, wherein the tobacco leaf is a harvested tobacco leaf.

30. The harvested leaf of a tobacco plant according to claim 29 wherein the harvested leaf is a cut harvested leaf.

31. A processed tobacco leaf comprising a tobacco cell according to claim 17.

32. The processed tobacco leaf according to claim 31 wherein the tobacco is processed by curing, fermenting, pasteurising or a combination thereof.

33. The processed tobacco leaf according to claim 31 wherein the processed tobacco leaf is a cut processed tobacco leaf.

34. A tobacco product comprising a processed tobacco leaf according to claim 31.

35. The tobacco product according to claim 34, wherein the tobacco product is a rolling tobacco, a cigarette, a cigar, or a cigarillo.

36. The tobacco product according to claim 34, wherein the tobacco product is a smokeless tobacco product.

37. The tobacco product according to claim 34, wherein the tobacco product is a tobacco heating device comprising the processed tobacco leaf.

38. A tobacco product according to claim 37, wherein the tobacco product is an aerosol generating device comprising the processed tobacco leaf.

* * * * *